United States Patent
Monia et al.

(10) Patent No.: US 12,115,225 B2
(45) Date of Patent: Oct. 15, 2024

(54) GLP-1 RECEPTOR LIGAND MOIETY CONJUGATED OLIGONUCLEOTIDES AND USES THEREOF

(71) Applicants: AstraZeneca AB, Södertälje (SE); Ionis Pharmaceuticals, Inc., Carlsbad, CA (US)

(72) Inventors: Brett P. Monia, Encinitas, CA (US); Thazha P. Prakash, Carlsbad, CA (US); Garth A. Kinberger, San Diego, CA (US); Richard Lee, Oceanside, CA (US); Punit P. Seth, Carlsbad, CA (US); Shalini Andersson, Södertälje (SE); Eva Carina Ämmälä, Mölndal (SE); Daniel Laurent Knerr, Mölndal (SE); Maria Astrid Ölwegård-Halvarsson, Mölndal (SE); Eric Valeur, Mölndal (SE); William John Drury, III, Mölndal (SE)

(73) Assignees: ASTRAZENECA AB, Södertälje (SE); IONIS PHARMACEUTICALS, INC., Carlsbad, CA (US)

( * ) Notice: Subject to any disclaimer, the term of this patent is extended or adjusted under 35 U.S.C. 154(b) by 46 days.

(21) Appl. No.: 17/231,409

(22) Filed: Apr. 15, 2021

(65) Prior Publication Data
US 2021/0346509 A1 Nov. 11, 2021

Related U.S. Application Data

(63) Continuation of application No. 16/098,971, filed as application No. PCT/US2017/031010 on May 4, 2017, now abandoned.

(60) Provisional application No. 62/333,080, filed on May 6, 2016.

(51) Int. Cl.
| | |
|---|---|
| C07H 21/04 | (2006.01) |
| A61K 31/7125 | (2006.01) |
| A61K 31/713 | (2006.01) |
| A61K 38/17 | (2006.01) |
| A61K 47/54 | (2017.01) |
| A61K 47/64 | (2017.01) |
| A61K 47/65 | (2017.01) |
| C12N 15/11 | (2006.01) |
| A61P 35/00 | (2006.01) |

(52) U.S. Cl.
CPC ...... *A61K 47/6425* (2017.08); *A61K 31/7125* (2013.01); *A61K 31/713* (2013.01); *A61K 38/1796* (2013.01); *A61K 47/549* (2017.08); *A61K 47/65* (2017.08); *C12N 15/111* (2013.01); *A61P 35/00* (2018.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/3513* (2013.01); *C12N 2310/3521* (2013.01); *C12N 2310/3525* (2013.01); *C12N 2310/3533* (2013.01); *C12N 2320/32* (2013.01)

(58) Field of Classification Search
CPC .................................................. C12N 15/113
See application file for complete search history.

(56) References Cited

U.S. PATENT DOCUMENTS

| | | |
|---|---|---|
| 2011/0046071 A1 | 2/2011 | Karasik et al. |
| 2011/0059478 A1 | 3/2011 | Kliewer et al. |
| 2012/0295958 A1 | 11/2012 | Freier et al. |
| 2012/0329708 A1 | 12/2012 | Dimarchi et al. |
| 2013/0143793 A1 | 6/2013 | Neerup et al. |
| 2015/0259416 A1 | 9/2015 | Berggren et al. |
| 2015/0320871 A1 | 11/2015 | DiMarchi et al. |
| 2015/0353930 A1 | 12/2015 | Narain et al. |
| 2016/0003808 A1 | 1/2016 | Aarbiou et al. |
| 2017/0189441 A1 | 7/2017 | Aaronson et al. |
| 2017/0202979 A1 | 7/2017 | Chakraborty et al. |
| 2017/0204422 A1 | 7/2017 | Rhoden-Smith et al. |
| 2019/0134214 A1 | 5/2019 | Monia et al. |

FOREIGN PATENT DOCUMENTS

| | | | |
|---|---|---|---|
| CN | 103857408 A | 6/2014 | |
| CN | 104884618 A | 9/2015 | |
| JP | 2014524908 A | 9/2014 | |
| JP | 2014525901 A | 10/2014 | |
| WO | 8706941 A1 | 11/1987 | |
| WO | 2008/050329 A2 | 5/2008 | |
| WO | 2009089186 A2 | 7/2009 | |
| WO | WO 2011/143209 A1 * | 11/2011 | ........... C12N 15/113 |
| WO | 2012177443 A2 | 12/2012 | |
| WO | 2012177444 A2 | 12/2012 | |
| WO | 2014140113 A1 | 9/2014 | |
| WO | 2014203518 A1 | 12/2014 | |
| WO | 2015/010135 A2 | 1/2015 | |
| WO | 2016/022753 A1 | 2/2016 | |

(Continued)

OTHER PUBLICATIONS

Hayes M.R., et al., "Comparative Effects of the Long-acting Glp-1 Receptor Ligands, Liraglutide and Exendin-4, on Food Intake and Body Weight Suppression in Rats," Obesity (Silver Spring), Jul. 2011, vol. 19, No. 7, pp. 1342-1349.

Juliano R.L., et al., "Receptors, Endocytosis, and Trafficking: The Biological Basis of Targeted Delivery of Antisense and siRNA Oligonucleotides," Journal of Drug Target, Jan. 2013, vol. 21, No. 1, pp. 27-43.

St-Pierre G., et al., "Synthesis and Biological Evaluation of Sialyl-oligonucleotide Conjugates Targeting Leukocyte Btrans-Membranal Receptor Cd22 as Delivery Agents for Nucleic Acid Drugs," Bioorganic Medicinal Chemistry, Elsevier, Amsterdam, NL, Mar. 29, 2016, vol. 24, No. 11, DOI: 10.1016/J.BMC.2016.03. 047, ISSN 0968-0896, pp. 2397-2409, XP029527554.

(Continued)

*Primary Examiner* — Amy H Bowman

(57) ABSTRACT

The present embodiments provide compounds and methods for targeting cells expressing GLP-1 receptor.

12 Claims, 3 Drawing Sheets

Specification includes a Sequence Listing.

(56) References Cited

FOREIGN PATENT DOCUMENTS

| WO | 2017053995 A1 | 3/2017 |
|---|---|---|
| WO | 2017192820 A1 | 11/2017 |

OTHER PUBLICATIONS

Ammala, et al. "Targeted delivery of antisense oligonucleotides to pancreatic cells," Sci. Adv. URL:https://www.ncbi.nlm.nih.gov/pmc/articles/PMC6192685/pdf/aat3386.pdf (Oct. 17, 2018).

Brom et al. "Radiolabelled GLP-1 analogues for in vivo targeting of insulinomas," Contrast Media & Molecular Imaging, 7(2): 160-166 (Mar. 1, 2012).

Finan et al., "Targeted estrogen delivery reverses the metabolic syndrome," Nature Medicine, 18(12): 1847-1856 (Dec. 1, 2012).

Hung et al. "Characterization of Target mRNA Reduction Through in situ Hybridization in Multiple Organ Systems Following Systemic Antisense Treatment in Animals," Nucleic Acid Therapeutics, 23(6): 369-378 (Dec. 1, 2013).

International Search Report in PCT/IB18/058752, mailed May 17, 2019.

Liang Zhang et al. "Quantitative Impact of Plasma Clearance and Down-regulation on GLP-1 Receptor Molecular Imaging," Molecular Imaging & Biology, 18(1): 79-89 ( Feb. 2016).

Ming et al. "Intracellular delivery of an antisense oligonucleotide via endocytosis of a G-protein-coupled receptor," Nucleic Acids Research Advance Access, 38(19): 6567-6576 (Jun. 5, 2010).

Samuel et al., "Targeting FOX01 in Mice Using Antisense Oligonucleotide Improves Hepatic and Peripheral Insulin Action," Diabetes, 55(7): 2042-2050 (Jul. 1, 2006).

Sloop et al., "Hepatic and glucagon-like peptide-1-mediated reversal of diabetes by glucagon receptor antisense oligonucleotide inhibitors." The Journal of Clinical Investigation, 113(11): 1571-1581 (Jun. 2004).

Wang et al. "GLP-1 Targeting Magnetic Nanoparticles for Pancreatic Islet Imaging," Diabetes, 63(5): 1465-1474 (Jan. 23, 2014).

Koerner, et al., "GLP-1 Receptor Expression in Human Tumors and Human Normal Tissues: Potential for In Vivo Targeting". The Journal of Nuclear Medicine, May 2007, vol. 48, No. 5, pp. 736-743.

Willard, et al., "Small Molecule Drug Discovery at the Glucagon-Like Peptide-1 Receptor", Exp. Diabetes Res., Feb. 2012, vol. 2012, pp. 1-9.

International Search Report for International Application No. PCT/US2017/031010, dated Jul. 26, 2017.

"Crosslinking Technical Handbook", Thermo Scientific, Aug. 20, 2015, 57 Pages.

Extended European Search Report for European Application No. 17793322.3, mailed Dec. 11, 2019, 12 Pages.

Fontaine S.D., et al., "Long-Term Stabilization of Maleimide-Thiol Conjugates", Bioconjugate Chemistry, 2015, vol. 26, pp. 145-152.

Henke E., et al., "Peptide-Conjugated Antisense Oligonucleotides for Targeted Inhibition of a Transcriptional Regulator in Vivo", Nature Biotechnology, Jan. 2008, vol. 26, No. 1, pp. 91-100.

Ihara T., et al., "Cooperative DNA Probing using a Beta-Cyclodextrin-DNA Conjugate and a Nucleobase-Specific Fluorescent Ligand", Journal of the American Chemical Society, 2009, vol. 131, pp. 1386-1387.

International Preliminary Report on Patentability for International Application No. PCT/US2017/031010, mailed Nov. 15, 2018, 7 Pages.

Juliano R.L., et al., "The Chemistry and Biology of Oligonucleotide Conjugates", Accounts of Chemical Research, 2012, vol. 45, No. 7, pp. 1067-1076.

Koonin E.V. et al., "Chapter 2 Evolutionary Concept in Genetics and Genomics, Sequence—Evolution—Function: Computational Approaches in Comparative Genomics", Boston, Kluwer Academic, NCBI Bookshelf, 2003, 25 pages.

Kuzuya A., et al., "Efficient Guest Inclusion by β-Cyclodextrin Attached to the Ends of DNA Oligomers upon Hybridization to Various DNA Conjugates", Bioconjugate Chemistry, 2009, vol. 20, pp. 1643-1649.

Rost B., "Twilight Zone of Protein Sequence Alignments", Protein Engineering, 1999, vol. 12, No. 2, pp. 85-94.

Tumey L.J., et al., "Mild Method for Succinimide Hydrolysis on ADCs: Impact on ADC Potency, Stability, Exposure and Efficacy", Bioconjugate Chemistry, vol. 25, No. 10, 2014, pp. 1871-1880, PMID: 25216346.

Webber C., et al., "Genes and Homology", Current Biology, May 4, 2004, vol. 14, No. 9, pp. R332-R333.

Written Opinion for International Application No. PCT/US2017/031010, mailed Jul. 26, 2017, 5 Pages.

\* cited by examiner

SEQUENCE LISTING

```
<160> NUMBER OF SEQ ID NOS: 79

<210> SEQ ID NO 1
<211> LENGTH: 31
<212> TYPE: PRT
<213> ORGANISM: Artificial sequence
<220> FEATURE:
<223> OTHER INFORMATION: Synthetic peptide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Artificial sequence
<220> FEATURE:
<223> OTHER INFORMATION: Synthetic peptide

<400> SEQUENCE: 2
```

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 27
<212> TYPE: PRT
<213> ORGANISM: Artificial sequence
<220> FEATURE:
<223> OTHER INFORMATION: Synthetic peptide

<400> SEQUENCE: 3

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly
            20                  25

<210> SEQ ID NO 4
<211> LENGTH: 27
<212> TYPE: PRT
<213> ORGANISM: Artificial sequence
<220> FEATURE:
<223> OTHER INFORMATION: Synthetic peptide

<400> SEQUENCE: 4

Glu Gly Thr Phe Thr Ser Asp Val Ser Ser Tyr Leu Glu Glu Gln Ala
1               5                   10                  15

Ala Lys Glu Phe Ile Ala Trp Leu Val Lys Gly
            20                  25

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib

<400> SEQUENCE: 5

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Ala, Val, or Gly
<220> FEATURE:
<221> NAME/KEY: MOD_RES
<222> LOCATION: (16)..(16)
<223> OTHER INFORMATION: Gly, Lys, or Glu
<220> FEATURE:
```

```
<221> NAME/KEY: MOD_RES
<222> LOCATION: (17)..(17)
<223> OTHER INFORMATION: Gln or Lys
<220> FEATURE:
<221> NAME/KEY: MOD_RES
<222> LOCATION: (24)..(24)
<223> OTHER INFORMATION: Ala or Glu
<220> FEATURE:
<221> NAME/KEY: MOD_RES
<222> LOCATION: (27)..(27)
<223> OTHER INFORMATION: Val or Lys
<220> FEATURE:
<221> NAME/KEY: MOD_RES
<222> LOCATION: (28)..(28)
<223> OTHER INFORMATION: Lys, Asn, or Arg
<220> FEATURE:
<221> NAME/KEY: MOD_RES
<222> LOCATION: (30)..(30)
<223> OTHER INFORMATION: Arg or Gly
<220> FEATURE:
<221> NAME/KEY: MOD_RES
<222> LOCATION: (31)..(31)
<223> OTHER INFORMATION: Gly, His, Pro, or not present

<400> SEQUENCE: 6

His Xaa Glu Gly Thr Phe Thr Ser Asp Val Ser Ser Tyr Leu Glu Xaa
1               5                   10                  15

Xaa Ala Ala Lys Glu Phe Ile Xaa Trp Leu Xaa Xaa Gly Xaa Xaa
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic peptide

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic peptide

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic peptide

<400> SEQUENCE: 9

His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30
```

```
<210> SEQ ID NO 10
<211> LENGTH: 31
<212> TYPE: PRT
<213> ORGANISM: Artificial Sequence
<220> FEATURE:
<223> OTHER INFORMATION: Synthetic peptide

<400> SEQUENCE: 10

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic peptide

<400> SEQUENCE: 11

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic peptide

<400> SEQUENCE: 12

His Gly Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic peptide

<400> SEQUENCE: 13

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic peptide

<400> SEQUENCE: 14

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
```

```
<210> SEQ ID NO 15
<211> LENGTH: 31
<212> TYPE: PRT
<213> ORGANISM: Artificial Sequence
<220> FEATURE:
<223> OTHER INFORMATION: Synthetic peptide

<400> SEQUENCE: 15

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Synthetic peptide

<400> SEQUENCE: 16

His Gly Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic peptide

<400> SEQUENCE: 17

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic peptide

<400> SEQUENCE: 18

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic peptide

<400> SEQUENCE: 19

His Val Glu Gly Thr Phe Thr Ser Asp Val Ser Ser Tyr Leu Glu Glu
1               5                   10                  15
```

```
Gln Ala Ala Lys Glu Phe Ile Ala Trp Leu Val Lys Gly Gly
        20                  25                  30
```

<210> SEQ ID NO 20
<211> LENGTH: 30
<212> TYPE: PRT
<213> ORGANISM: Artificial Sequence
<220> FEATURE:
<223> OTHER INFORMATION: Synthetic peptide

<400> SEQUENCE: 20

```
His Val Glu Gly Thr Phe Thr Ser Asp Val Ser Ser Tyr Leu Glu Glu
1               5                   10                  15

Gln Ala Ala Lys Glu Phe Ile Ala Trp Leu Val Asn Gly Gly
        20                  25                  30
```

<210> SEQ ID NO 21
<211> LENGTH: 30
<212> TYPE: PRT
<213> ORGANISM: Artificial Sequence
<220> FEATURE:
<223> OTHER INFORMATION: Synthetic peptide

<400> SEQUENCE: 21

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Asn Gly Gly
        20                  25                  30
```

<210> SEQ ID NO 22
<211> LENGTH: 40
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 22

```
His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
        20                  25                  30

Ser Gly Ala Pro Pro Pro Ser Cys
        35                  40
```

<210> SEQ ID NO 23
<211> LENGTH: 40
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: misc_feature
<222> LOCATION: (40)..(40)
<223> OTHER INFORMATION: Xaa is Penicillamine (Pen)

<400> SEQUENCE: 23

```
His Xaa Glu Gly Thr Phe Thr Ser Asp Val Ser Ser Tyr Leu Glu Glu
1               5                   10                  15
```

Gln Ala Ala Lys Glu Phe Ile Ala Trp Leu Val Lys Gly Gly Pro Ser
            20                  25                  30

Ser Gly Ala Pro Pro Pro Ser Xaa
        35                  40

<210> SEQ ID NO 24
<211> LENGTH: 31
<212> TYPE: PRT
<213> ORGANISM: Artificial sequence
<220> FEATURE:
<223> OTHER INFORMATION: Synthetic peptide

<400> SEQUENCE: 24

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Cys
            20                  25                  30

<210> SEQ ID NO 25
<211> LENGTH: 39
<212> TYPE: PRT
<213> ORGANISM: Artificial sequence
<220> FEATURE:
<223> OTHER INFORMATION: Synthetic peptide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 26
<211> LENGTH: 40
<212> TYPE: PRT
<213> ORGANISM: Artificial sequence
<220> FEATURE:
<223> OTHER INFORMATION: Synthetic peptide

<400> SEQUENCE: 26

Ala Gly Glu Gly Thr Phe Thr Ser Asp Val Ser Ser Tyr Leu Glu Gly
1               5                   10                  15

Gln Ala Ala Lys Glu Ala Ile Ala Trp Leu Val Lys Gly Gly Pro Ser
            20                  25                  30

Ser Gly Ala Pro Pro Pro Ser Cys
        35                  40

<210> SEQ ID NO 27
<211> LENGTH: 40
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (40)..(40)
<223> OTHER INFORMATION: Xaa is Penicillamine (Pen)

<400> SEQUENCE: 27

Ala Gly Glu Gly Thr Phe Thr Ser Asp Val Ser Ser Tyr Leu Glu Gly
1               5                   10                  15

Gln Ala Ala Lys Glu Ala Ile Ala Trp Leu Val Lys Gly Gly Pro Ser
            20                  25                  30

```
Ser Gly Ala Pro Pro Ser Xaa
        35                  40

<210> SEQ ID NO 28
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 28

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val
            20                  25

<210> SEQ ID NO 29
<211> LENGTH: 28
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 29

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys
            20                  25

<210> SEQ ID NO 30
<211> LENGTH: 29
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 30

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly
            20                  25

<210> SEQ ID NO 31
<211> LENGTH: 30
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 31

His Xaa Glu Gly Thr Phe Thr Ser Asp Val Ser Ser Tyr Leu Glu Glu
```

```
                1               5                   10                  15
Gln Ala Ala Lys Glu Phe Ile Ala Trp Leu Val Lys Gly Gly
            20                  25                  30

<210> SEQ ID NO 32
<211> LENGTH: 31
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 32

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 33
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 33

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

<210> SEQ ID NO 34
<211> LENGTH: 33
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 34

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser

<210> SEQ ID NO 35
<211> LENGTH: 34
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
```

```
<400> SEQUENCE: 35

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Gly

<210> SEQ ID NO 36
<211> LENGTH: 35
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 36

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Gly Ala
        35

<210> SEQ ID NO 37
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 37

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Gly Ala Pro
        35

<210> SEQ ID NO 38
<211> LENGTH: 40
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: Xaa is 4-azidonorleucine

<400> SEQUENCE: 38

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40
```

<210> SEQ ID NO 39
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (32)..(32)
<223> OTHER INFORMATION: Xaa is 4-azidonorleucine

<400> SEQUENCE: 39

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Xaa
            20                  25                  30

<210> SEQ ID NO 40
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (21)..(21)
<223> OTHER INFORMATION: Xaa is Lysine (5 azido pentanoic acid amide)

<400> SEQUENCE: 40

His Xaa Glu Gly Thr Phe Thr Ser Asp Val Ser Ser Tyr Leu Glu Gly
1               5                   10                  15

Gln Ala Ala Asn Xaa Glu Phe Ile Ala Trp Leu Val Arg Gly Arg Gly
            20                  25                  30

<210> SEQ ID NO 41
<211> LENGTH: 31
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (31)..(31)
<223> OTHER INFORMATION: Xaa is 4-azidonorleucine

<400> SEQUENCE: 41

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Xaa
            20                  25                  30

<210> SEQ ID NO 42
<211> LENGTH: 31

```
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (31)..(31)
<223> OTHER INFORMATION: Xaa is 4-azidonorleucine

<400> SEQUENCE: 42

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 43
<211> LENGTH: 38
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (38)..(38)
<223> OTHER INFORMATION: Xaa is 4-azidonorleucine

<400> SEQUENCE: 43

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Gly Ala Pro Pro Xaa
            35

<210> SEQ ID NO 44
<211> LENGTH: 34
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (44)..(44)
<223> OTHER INFORMATION: Xaa is 4-azidonorleucine

<400> SEQUENCE: 44

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Xaa

<210> SEQ ID NO 45
<211> LENGTH: 29
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
```

```
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Xaa is 4-azidonorleucine

<400> SEQUENCE: 45

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Xaa
            20                  25

<210> SEQ ID NO 46
<211> LENGTH: 28
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: Xaa is 4-azidonorleucine

<400> SEQUENCE: 46

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Xaa
            20                  25

<210> SEQ ID NO 47
<211> LENGTH: 28
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib

<400> SEQUENCE: 47

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Cys
            20                  25

<210> SEQ ID NO 48
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (27)..(27)
<223> OTHER INFORMATION: Xaa is 4-azidonorleucine

<400> SEQUENCE: 48

His Xaa Glu Gly Thr Phe Thr Ser Asp Val Ser Ser Tyr Leu Glu Glu
1               5                   10                  15
```

Gln Ala Ala Lys Glu Phe Ile Ala Trp Leu Xaa
            20                  25

<210> SEQ ID NO 49
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (26)..(26)
<223> OTHER INFORMATION: Xaa is 4-azidonorleucine

<400> SEQUENCE: 49

His Xaa Glu Gly Thr Phe Thr Ser Asp Val Ser Ser Tyr Leu Glu Glu
1               5                   10                  15

Gln Ala Ala Lys Glu Phe Ile Ala Trp Xaa
            20                  25

<210> SEQ ID NO 50
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Xaa is 4-azidonorleucine

<400> SEQUENCE: 50

His Xaa Glu Gly Thr Phe Thr Ser Asp Val Ser Ser Tyr Leu Glu Glu
1               5                   10                  15

Gln Ala Ala Xaa
            20

<210> SEQ ID NO 51
<211> LENGTH: 30
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (30)..(30)
<223> OTHER INFORMATION: Xaa is 4-azidonorleucine

<400> SEQUENCE: 51

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Xaa
            20                  25                  30

<210> SEQ ID NO 52
<211> LENGTH: 29
<212> TYPE: PRT
<213> ORGANISM: Artificial sequence
<220> FEATURE:
<223> OTHER INFORMATION: Synthetic peptide

```
<220> FEATURE:
<221> NAME/KEY: MOD_RES
<222> LOCATION: (29)..(29)
<223> OTHER INFORMATION: Xaa is 4-azidonorleucine

<400> SEQUENCE: 52

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa
            20                  25

<210> SEQ ID NO 53
<211> LENGTH: 28
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (28)..(28)
<223> OTHER INFORMATION: Xaa is 4-azidonorleucine

<400> SEQUENCE: 53

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa
            20                  25

<210> SEQ ID NO 54
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (27)..(27)
<223> OTHER INFORMATION: Xaa is 4-azidonorleucine

<400> SEQUENCE: 54

His Gly Glu Gly Thr Phe Thr Ser Asp Leu Ser Lys Gln Met Glu Glu
1               5                   10                  15

Glu Ala Val Arg Leu Phe Ile Glu Trp Leu Xaa
            20                  25

<210> SEQ ID NO 55
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (26)..(26)
<223> OTHER INFORMATION: Xaa is 4-azidonorleucine

<400> SEQUENCE: 55

His Gly Glu Gly Thr Phe Thr Ser Asp Leu Ser Lys Gln Met Glu Glu
1               5                   10                  15

Glu Ala Val Arg Leu Phe Ile Glu Trp Xaa
            20                  25

<210> SEQ ID NO 56
<211> LENGTH: 40
<212> TYPE: PRT
<213> ORGANISM: Artificial sequence
<220> FEATURE:
```

<223> OTHER INFORMATION: Synthetic peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (40)..(40)
<223> OTHER INFORMATION: Xaa is 4-azidonorleucine

<400> SEQUENCE: 56

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Gly Ala Pro Pro Pro Ser Xaa
        35                  40

<210> SEQ ID NO 57
<211> LENGTH: 40
<212> TYPE: PRT
<213> ORGANISM: Artificial sequence
<220> FEATURE:
<223> OTHER INFORMATION: Synthetic peptide

<400> SEQUENCE: 57

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Cys
        35                  40

<210> SEQ ID NO 58
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 58
tcagcattct aatagcagc                                                19

<210> SEQ ID NO 59
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 59
tcatcttctt aaaataccc                                                19

<210> SEQ ID NO 60
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 60
tcaggccaat acgccgtca                                                19

<210> SEQ ID NO 61
<211> LENGTH: 23

<212> TYPE: DNA
<213> ORGANISM: Artificial sequence
<220> FEATURE:
<223> OTHER INFORMATION: Synthetic oligonucleotide

<400> SEQUENCE: 61
tcagccaagg tctgaaggtc acc                                          23

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
gctgctatta gaatgc                                                  16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
gcattctaat agcagc                                                  16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
tcttcttaaa ataccc                                                  16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
gcattctaat agcagc                                                  16

<210> SEQ ID NO 66
<211> LENGTH: 24
<212> TYPE: DNA
<213> ORGANISM: Artificial sequence
<220> FEATURE:
<223> OTHER INFORMATION: Primer

<400> SEQUENCE: 66
ccattctatc atcaacgggt acaa                                         24

<210> SEQ ID NO 67
<211> LENGTH: 22
<212> TYPE: DNA
<213> ORGANISM: Artificial sequence
<220> FEATURE:
<223> OTHER INFORMATION: Primer

<400> SEQUENCE: 67
agcaagtggg aaggtgtaat cc					22

<210> SEQ ID NO 68
<211> LENGTH: 20
<212> TYPE: DNA
<213> ORGANISM: Artificial sequence
<220> FEATURE:
<223> OTHER INFORMATION: Primer

<400> SEQUENCE: 68
cagtcacata cggccaatcc					20

<210> SEQ ID NO 69
<211> LENGTH: 24
<212> TYPE: DNA
<213> ORGANISM: Artificial sequence
<220> FEATURE:
<223> OTHER INFORMATION: Primer

<400> SEQUENCE: 69
cgtaacttga tttgctgtcc tgaa					24

<210> SEQ ID NO 70
<211> LENGTH: 25
<212> TYPE: DNA
<213> ORGANISM: Artificial sequence
<220> FEATURE:
<223> OTHER INFORMATION: Probe

<400> SEQUENCE: 70
tgagcccttt gccccagatg cctat					25

<210> SEQ ID NO 71
<211> LENGTH: 24
<212> TYPE: DNA
<213> ORGANISM: Artificial sequence
<220> FEATURE:
<223> OTHER INFORMATION: Primer

<400> SEQUENCE: 71
gaggaatcag atgaggatat ggga					24

<210> SEQ ID NO 72
<211> LENGTH: 20
<212> TYPE: DNA
<213> ORGANISM: Artificial sequence
<220> FEATURE:
<223> OTHER INFORMATION: Primer

<400> SEQUENCE: 72
aagcaggctg acttggttgc					20

<210> SEQ ID NO 73
<211> LENGTH: 26
<212> TYPE: DNA
<213> ORGANISM: Artificial sequence
<220> FEATURE:
<223> OTHER INFORMATION: Probe

<400> SEQUENCE: 73
tcggtctctt cgactaatcc cgccaa					26

<210> SEQ ID NO 74
<211> LENGTH: 20
<212> TYPE: DNA
<213> ORGANISM: Artificial sequence

```
<220> FEATURE:
<223> OTHER INFORMATION: Primer

<400> SEQUENCE: 74
aggcgttgtg cgtagaggat                                              20

<210> SEQ ID NO 75
<211> LENGTH: 29
<212> TYPE: DNA
<213> ORGANISM: Artificial sequence
<220> FEATURE:
<223> OTHER INFORMATION: Primer

<400> SEQUENCE: 75
aaaggttacc ataagtaagt tccagaaaa                                    29

<210> SEQ ID NO 76
<211> LENGTH: 28
<212> TYPE: DNA
<213> ORGANISM: Artificial sequence
<220> FEATURE:
<223> OTHER INFORMATION: Probe

<400> SEQUENCE: 76
agtggttggt aaaaatccgt gaggtcgg                                     28

<210> SEQ ID NO 77
<211> LENGTH: 21
<212> TYPE: DNA
<213> ORGANISM: Artificial sequence
<220> FEATURE:
<223> OTHER INFORMATION: siRNA

<400> SEQUENCE: 77
ttatctataa tgatcaggta a                                            21

<210> SEQ ID NO 78
<211> LENGTH: 19
<212> TYPE: DNA
<213> ORGANISM: Artificial sequence
<220> FEATURE:
<223> OTHER INFORMATION: siRNA

<400> SEQUENCE: 78
acctgatcat tatagataa                                               19

<210> SEQ ID NO 79
<211> LENGTH: 32
<212> TYPE: PRT
<213> ORGANISM: Artificial sequence
<220> FEATURE:
<223> OTHER INFORMATION: Synthetic peptide

<400> SEQUENCE: 79

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Ser Cys
            20                  25                  30
```

GLP-1 RECEPTOR LIGAND MOIETY CONJUGATED OLIGONUCLEOTIDES AND USES THEREOF

SEQUENCE LISTING

The present application is being filed along with a Sequence Listing in electronic format. The Sequence Listing is provided as a file entitled BIOL0303WOSEQ_ST25.txt created Apr. 27, 2017, which is 29 kb in size. The information in the electronic format of the sequence listing is incorporated herein by reference in its entirety.

FIELD

The present embodiments provide compounds and methods for targeting cells expressing GLP-1 receptor.

BACKGROUND

The GLP-1 receptor is a class 2, G protein-coupled receptor that couples to adenylate cyclase via a stimulatory G protein receptor. Intestinal nutrient stimulation leads to release of glucagon like peptide-1 into the circulation. Circulating GLP-1 binds to the GLP-1 receptor on the beta islet cells of the pancreas. This activates the GLP-1 receptor which induces signaling events that result in insulin exocytosis from beta islet cells. Binding between GLP-1 and GLP-1 receptor leads to internalization of the receptor into the cytoplasm and eventual sorting into lysosomes (Kuna et al., 2013 *Am J Physiol Endo Metab* 305:E161-E170).

SUMMARY

Embodiments provided herein are directed to compounds and methods for modulating the expression of a nucleic acid target in cells expressing GLP-1 receptor. In certain embodiments, a compound comprises an oligonucleotide and GLP-1 receptor ligand conjugate moiety. In certain embodiments, a compound comprises an oligonucleotide, conjugate linker, and GLP-1 receptor ligand conjugate moiety. In certain embodiments, contacting a cell expressing GLP-1 receptor, such as a pancreatic beta islet cell, with a compound provided herein modulates expression of a nucleic acid target in the cell. In certain embodiments, a compound comprising a GLP-1 receptor ligand conjugate moiety selectively or preferentially targets a cell expressing GLP-1 receptor compared to a cell not expressing GLP-1 receptor. In certain embodiments, a compound comprising a GLP-1 receptor ligand conjugate moiety selectively or preferentially targets a cell expressing GLP-1 receptor compared to a compound not comprising a GLP-1 receptor ligand conjugate moiety.

DETAILED DESCRIPTION

Figure 1A:
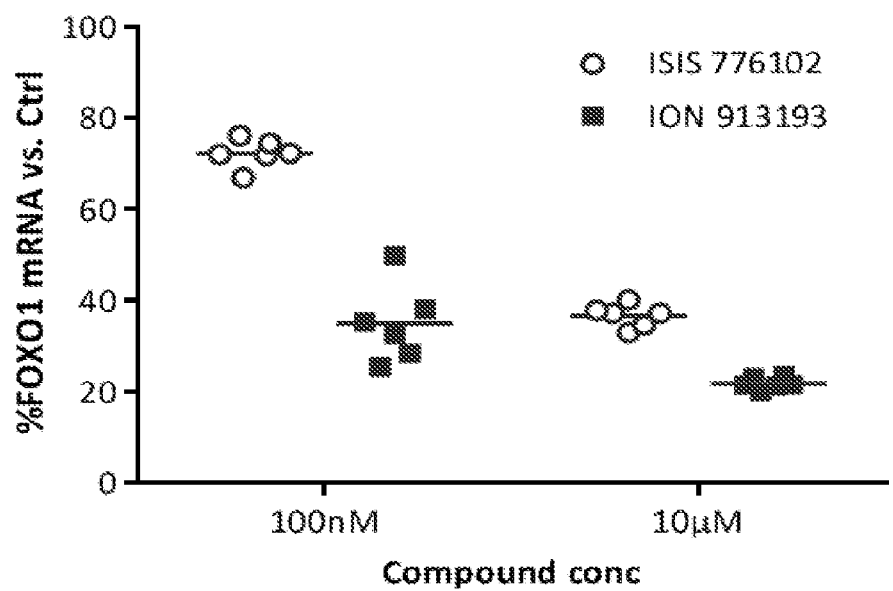
FIG. 1 is a graph showing the percent FOXO1 mRNA (FIG. 1A) and MALAT1 mRNA (FIG. 1B) relative to antisense oligonucleotide (ASO) concentration in HEK293 cells treated with unconjugated parent ASO (ISIS 776102 or ISIS 556089) or GLP1-conjugated ASO (ISIS 913193 or ISIS 816385).

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO of an oligonucleotide in the examples contained herein is independent of any modification to a sugar moiety, an internucleoside linkage, or a nucleobase. As such, oligonucleotides defined by a SEQ ID NO may comprise, independently, one or more modifications to a sugar moiety, an internucleoside linkage, or a nucleobase. Oligonucleotides described by ISIS or ION number (ISIS # or ION #) indicate a combination of nucleobase sequence, chemical modification, and motif.

It is understood that throughout the specification, the first letter in a peptide sequence is the first amino acid of the peptide at the N-terminus and the last letter in a peptide sequence is the last amino acid of the peptide at the C-terminus unless indicated otherwise.

Unless otherwise indicated, the following terms have the following meanings:

"2'-deoxynucleoside" means a nucleoside comprising 2'-H (H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted"

or "2-modified" in reference to a sugar moiety means a sugar moiety comprising at least one 2'-substituent group other than H or OH.

"5-methylcytosine" means a cytosine with a methyl group attached to the 5 position.

"About" means within ±10% of a value. For example, if it is stated, "the compounds affected about 70% inhibition of a target nucleic acid", it is implied that target nucleic acid levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Aminoisobutyric acid" or "Aib" means 2-aminoisobutryic acid having the formula:

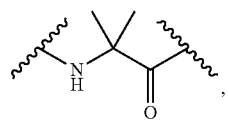 [SMILES: *NC(C)(C)C(*)=O]

unless stated otherwise.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a bicyclic furanosyl sugar moiety comprising a bridge connecting the 4'-carbon and the 2'-carbon, wherein the bridge has the formula: 4'-CH(CH$_3$)—O-2'.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Designing" or "Designed to" refer to the process of designing a compound that specifically hybridizes with a selected nucleic acid molecule.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Double-stranded antisense compound" means an antisense compound comprising two oligomeric compounds that are complementary to each other and form a duplex, and wherein one of the two said oligomeric compounds comprises an oligonucleotide.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating target nucleic acid can mean to increase or decrease the level of target nucleic acid in a cell, tissue, organ or organism. A "modulator" effects the change in the cell, tissue, organ or organism. For example, a compound can be a modulator that decreases the amount of target nucleic acid in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring. "Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified.

"Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Reduce" means to bring down to a smaller extent, size, amount, or number.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Selective" with respect to an effect refers to a greater effect on one thing over another by any quantitative extent or fold-difference. For example, a compound comprising a GLP-1 receptor conjugate ligand moiety that is "selective" for cells expressing GLP-1 receptor or "selectively" targets cells expressing GLP-1 receptor, targets cells expressing GLP-1 receptor to a greater extent than a compound not comprising a GLP-1 receptor conjugate ligand moiety. As another example, a compound comprising a GLP-1 receptor conjugate ligand moiety that is "selective" for cells expressing GLP-1 receptor or "selectively" targets cells expressing GLP-1 receptor, targets cells expressing GLP-1 receptor to a greater extent than cells that do not express or express relatively lower levels of GLP-1 receptor. It will be understood that the term "selective" does not require absolute all-or-none selectivity.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary compounds or nucleic acids.

"Target gene" refers to a gene encoding a target.

"Targeting" with respect to a target nucleic acid means the specific hybridization of an oligonucleotide to said target nucleic acid in order to induce a desired effect. "Targeting" with respect to a GLP-1 receptor means binding of a GLP-1 receptor ligand conjugate moiety to GLP-1 receptor.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

Certain Embodiments

In certain embodiments, a compound comprises an oligonucleotide and GLP-1 receptor ligand conjugate moiety. In certain embodiments, the oligonucleotide is a modified oligonucleotide. In certain embodiments, the compound further comprises a conjugate linker. In certain embodiments, the conjugate linker links the oligonucleotide to the GLP-1 receptor ligand conjugate moiety.

In certain embodiments, the oligonucleotide is 8 to 80 linked nucleosides in length, 10 to 30 linked nucleosides in length, 12 to 30 linked nucleosides in length, or 15 to 30 linked nucleosides in length.

In certain embodiments, the oligonucleotide is a modified oligonucleotide comprising at least one modified internucleoside linkage, at least one modified sugar, or at least one modified nucleobase. In certain embodiments, the modified internucleoside linkage is a phosphorothioate internucleoside linkage. In certain embodiments, each modified internucleoside linkage of the modified oligonucleotide is a phosphorothioate internucleoside linkage.

In creatin embodiments, the modified sugar is a bicyclic sugar, such as 4'-(CH2)-O-2' (LNA); 4'-(CH2)2-O-2' (ENA); or 4'-CH(CH3)-O-2' (cEt). In certain embodiments, the modified sugar is 2'-O-methoxyethyl, 2'-F, or 2'-OMe.

In certain embodiments, the modified nucleobase is a 5-methylcytosine.

In certain embodiments, the modified oligonucleotide comprises:
  a gap segment consisting of linked deoxynucleosides;
  a 5' wing segment consisting of linked nucleosides; and
  a 3' wing segment consisting of linked nucleosides;
wherein the gap segment is positioned immediately adjacent to and between the 5' wing segment and the 3' wing segment and wherein each nucleoside of each wing segment comprises a modified sugar.

In certain embodiments, the oligonucleotide is single-stranded.

In certain embodiments, the oligonucleotide is an antisense oligonucleotide, miRNA antagonist or miRNA mimic.

In certain embodiments, the compound comprises a double-stranded duplex. In certain embodiments, the double-stranded duplex comprises a first strand comprising the modified oligonucleotide and a second strand complementary to the first strand. In certain embodiments, the first strand comprising the modified oligonucleotide is complementary to a RNA transcript. In certain embodiments, the second strand is complementary to a RNA transcript. In certain embodiments, a compound comprises a double-stranded duplex comprising (i) a first strand comprising the modified oligonucleotide, optionally a conjugate linker, and the GLP-1 receptor ligand conjugate moiety and (ii) a second strand complementary to the first strand. In certain embodiments, a compound comprises a double-stranded duplex comprising (i) a first strand comprising the modified oligonucleotide, optionally a conjugate linker, and the GLP-1 receptor ligand conjugate moiety and (ii) a second strand complementary to the first strand; wherein the first strand is complementary to a RNA transcript. In certain embodiments, a compound comprises a double-stranded duplex comprising (i) a first strand comprising the modified oligonucleotide, optionally a conjugate linker, and the GLP-1 receptor ligand conjugate moiety and (ii) a second strand complementary to the first strand; wherein the second strand is complementary to a RNA transcript.

In certain embodiments, the compound is a miRNA mimic.

In certain embodiments, the compound comprises ribonucleotides. In certain embodiments, the compound comprises deoxyribonucleotides.

In certain embodiments, the oligonucleotide is complementary to a RNA transcript in a cell, such as a pancreatic cell or a pancreatic beta-islet cell.

In certain embodiments, the RNA transcript is pre-mRNA, mRNA, non-coding RNA, or miRNA.

In certain embodiments, the GLP-1 receptor ligand conjugate moiety is a peptide conjugate moiety, small molecule conjugate moiety, aptamer conjugate moiety, or antibody conjugate moiety targeted to GLP-1 receptor.

In certain embodiments, the peptide conjugate moiety is a GLP-1 peptide conjugate moiety.

In certain embodiments, the GLP-1 peptide conjugate moiety comprises an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, at least 96%, at least 97%, at least 98%, at least 99%, or 100% homologous to an equal length portion of the amino acid sequence of any of SEQ ID NOs: 1-57.

In certain embodiments, the GLP-1 peptide conjugate moiety comprises an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, at least 96%, at least 97%, at least 98%, at least 99%, or 100% identical to an equal length portion of the amino acid sequence of any of SEQ ID NOs: 1-57.

In certain embodiments, the GLP-1 peptide conjugate moiety is 8 to 50 amino acids in length and is at least 60%, at least 65%, at least 70%, at least 75%, at least 80%, at least 85%, at least 90%, at least 95%, at least 96%, at least 97%, at least 98%, at least 99%, or 100% homologous over its entire length to the amino acid sequence of any of SEQ ID NOs: 1-57.

In certain embodiments, the GLP-1 peptide conjugate moiety is at least 60%, at least 65%, at least 70%, at least 75%, at least 80%, at least 85%, at least 90%, at least 95%, at least 96%, at least 97%, at least 98%, at least 99%, or 100% identical over its entire length to the amino acid sequence of any of SEQ ID NOs: 1-57.

In certain embodiments, the GLP-1 peptide conjugate moiety comprises an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, at least 96%, at least 97%, at least 98%, at least 99%, or 100% homologous to an equal length portion of the amino acid sequence of GLP-1(7-37): HAEGTFTSDVSSYLEGQAAKEFIAWLVKGRG, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 1).

In certain embodiments, the GLP-1 peptide conjugate moiety comprises an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, at least 96%, at least 97%, at least 98%, at least 99%, or 100% identical to an equal length portion of the amino acid sequence of GLP-1(7-37).

In certain embodiments, the GLP-1 peptide conjugate moiety is 8 to 50 amino acids in length and is at least 60%, at least 65%, at least 70%, at least 75%, at least 80%, at least 85%, at least 90%, at least 95%, at least 96%, at least 97%, at least 98%, at least 99%, or 100% homologous over its entire length to the amino acid sequence of GLP-1(7-37) (SEQ ID NO: 1).

In certain embodiments, the GLP-1 peptide conjugate moiety comprises a conservative amino acid substitution, an amino acid analog, or an amino acid derivative.

In certain embodiments, the GLP-1 peptide conjugate moiety is at least 60%, at least 65%, at least 70%, at least 75%, at least 80%, at least 85%, at least 90%, at least 95%, at least 96%, at least 97%, at least 98%, at least 99%, or 100% identical over its entire length to the amino acid sequence of GLP-1(7-37) (SEQ ID NO: 1).

In certain embodiments, the GLP-1 peptide conjugate moiety comprises the amino acid sequence of GLP-1(7-37) (SEQ ID NO: 1).

In certain embodiments, the GLP-1 peptide conjugate moiety consists of the amino acid sequence of GLP-1(7-37) (SEQ ID NO: 1).

In certain embodiments, the GLP-1 peptide conjugate moiety comprises the amino acid sequence of GLP-1(7-36) amide: HAEGTFTSDVSSYLEGQAAKEFIAWLVKGR-NH$_2$, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ (SEQ ID NO: 2).

In certain embodiments, the GLP-1 peptide conjugate moiety consists of the amino acid sequence of GLP-1(7-36) amide: which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ (SEQ ID NO: 2).

In certain embodiments, the GLP-1 peptide conjugate moiety comprises or consists of the amino acid sequence of GLP-1(7-36): HAEGTFTSDVSSYLEGQAAKEFI-AWLVKGR, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQ ID NO: 2).

In certain embodiments, the GLP-1 peptide conjugate moiety comprises the amino acid sequence: EGTFTSDVS-SYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3).

In certain embodiments, the GLP-1 peptide conjugate moiety consists of the amino acid sequence: EGTFTSDVS-SYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3).

In certain embodiments, the GLP-1 peptide conjugate moiety comprises the amino acid sequence: EGTFTSDVS-SYLEEQAAKEFIAWLVKG, which in conventional three-letter code is: Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4).

In certain embodiments, the GLP-1 peptide conjugate moiety consists of the amino acid sequence: EGTFTSDVS-SYLEEQAAKEFIAWLVKG, which in conventional three-letter code is: Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4).

In certain embodiments, the GLP-1 peptide conjugate moiety comprises the amino acid sequence of any of SEQ ID NOs: 1-57.

In certain embodiments, the GLP-1 peptide conjugate moiety consists of the amino acid sequence of any of SEQ ID NOs: 1-57.

In certain embodiments, the GLP-1 peptide conjugate moiety can be a C-terminal amide or acid of any of SEQ ID NOs: 1-57.

In certain embodiments, the GLP-1 peptide conjugate moiety comprises the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Cys (SEQ ID NO: 22), wherein Aib is aminoisobutyric acid.

In certain embodiments, the GLP-1 peptide conjugate moiety consists of the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Cys (SEQ ID NO: 22), wherein Aib is aminoisobutyric acid.

In certain embodiments, the GLP-1 peptide conjugate moiety comprises the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Pen (SEQ ID NO: 23), wherein Aib is aminoisobutyric acid and Pen is penicillamine.

In certain embodiments, the GLP-1 peptide conjugate moiety consists of the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Pen (SEQ ID NO: 23), wherein Aib is aminoisobutyric acid and Pen is penicillamine.

In certain embodiments, the GLP-1 peptide conjugate moiety is capable of binding to GLP-1 receptor.

In certain embodiments, the GLP-1 receptor is expressed on the surface of a cell.

In certain embodiments, the cell is a pancreatic cell, such as a beta-islet cell.

In certain embodiments, the cell is in an animal.

In certain embodiments, the compound comprises at least one, at least two, at least three, at least four, or at least five GLP-1 receptor ligand conjugate moieties.

In certain embodiments, the conjugate linker links the GLP-1 receptor ligand conjugate moiety to the 5' end of the oligonucleotide.

In certain embodiments, the conjugate linker links the GLP-1 receptor ligand conjugate moiety to the 3' end of the oligonucleotide.

In certain embodiments, the conjugate linker is cleavable.

In certain embodiments, the conjugate linker comprises a disulfide linkage.

In certain embodiments, the disulfide linkage links the GLP-1 peptide conjugate moiety to the oligonucleotide.

In certain embodiments, the disulfide linkage links the C-terminus of the GLP-1 peptide conjugate moiety to the 5' end of the oligonucleotide.

In certain embodiments, the conjugate linker comprises 1-5 linker-nucleosides.

In certain embodiments, the conjugate linker comprises 3 linker-nucleosides.

In certain embodiments, the 3 linker-nucleosides have a TCA motif.

In certain embodiments, 1-5 linker-nucleosides do not comprise a TCA motif.

In certain embodiments, the conjugate linker comprises a hexylamino group.

In certain embodiments, the conjugate linker comprises a polyethylene glycol group.

In certain embodiments, the conjugate linker comprises a triethylene glycol group.

In certain embodiments, the conjugate linker comprises a phosphate group.

In certain embodiments, the conjugate linker comprises:

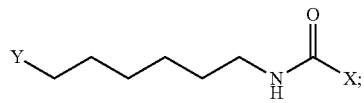

wherein X directly or indirectly attaches to the GLP-1 receptor ligand conjugate moiety; and Y directly or indirectly attaches to the modified oligonucleotide. In certain embodiments, X comprises O. In certain embodiments, Y comprises a phosphate group. In certain embodiments, X attaches to the GLP-1 receptor ligand conjugate moiety by a disulfide linkage.

In certain embodiments, the conjugate linker comprises:

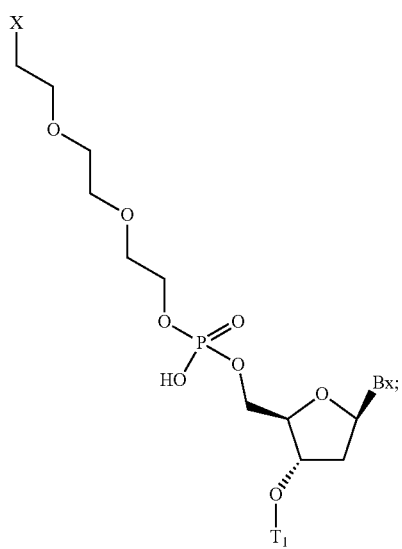

wherein X directly or indirectly attaches to the GLP-1 receptor ligand conjugate moiety; and wherein $T_1$ comprises the modified oligonucleotide; and Bx is a modified or unmodified nucleobase. In certain embodiments, X comprises a disulfide linkage.

In certain embodiments, the conjugate linker comprises:

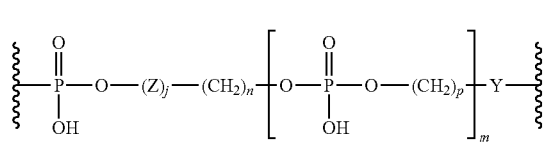

wherein:
the phosphate group is connected to the modified oligonucleotide and Y is connected to the conjugate group;
Y is a phosphodiester or amino (—NH—) group;
Z is a pyrrolidinyl group having the formula:

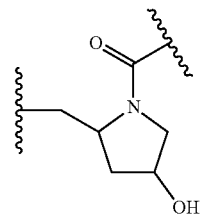 [SMILES: *CC1CC(O)CN1C(*)=O]

j is 0 or 1;
n is from about 1 to about 10;
p is from 1 to about 10;
m is 0 or from 1 to 4; and
when Y is amino then m is 1.

In certain embodiments, Y is amino (—NH—) or phosphodiester group. In certain embodiments, n is 3 and p is 3. In certain embodiments, n is 6 and p is 6. In certain embodiments, n is from 2 to 10 and p is from 2 to 10. In certain embodiments, n and p are different. In certain embodiments, n and p are the same. In certain embodiments, m is 0 or 1. In certain embodiments, j is 0. In certain embodiments, j is 1 and Z has the formula:

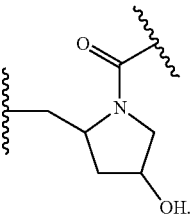 [SMILES: *CC1CC(O)CN1C(*)=O]

In certain embodiments, n is 2 and p is 3. In certain embodiments, n is 5 and p is 6.

In certain embodiments, the conjugate linker comprises:

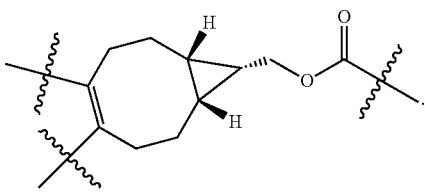 [SMILES: *C(=O)OC[C@@H]1[C@@H]2CC/C(*)=C(/*)CC[C@@H]21]

In certain embodiments, the conjugate linker comprises:

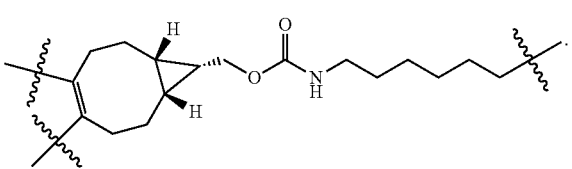 [SMILES: *CCCCCCNC(=O)OC[C@@H]1[C@@H]2CC/C(*)=C(/*)CC[C@@H]21]

In certain embodiments, the compound comprising a conjugate linker comprises:

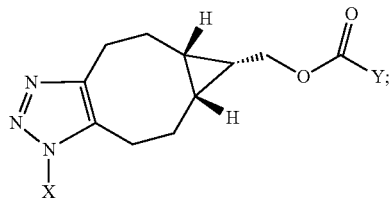

wherein
N—N═N represents an azido group of the GLP-1 receptor ligand conjugate moiety and X directly or indirectly attaches to the remainder of the GLP-1 receptor ligand conjugate moiety; and
Y directly or indirectly attaches to the oligonucleotide.

In certain embodiments, the compound comprising a conjugate linker comprises:

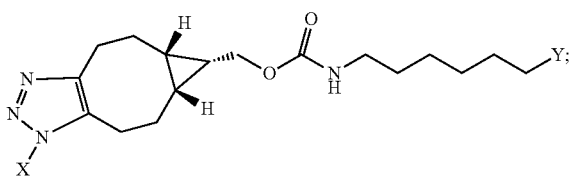

wherein
N—N═N represents an azido group of the GLP-1 receptor ligand conjugate moiety and X directly or indirectly attaches to the remainder of the GLP-1 receptor ligand conjugate moiety; and
Y directly or indirectly attaches to the oligonucleotide.

In certain embodiments, the compound comprising a conjugate linker comprises:

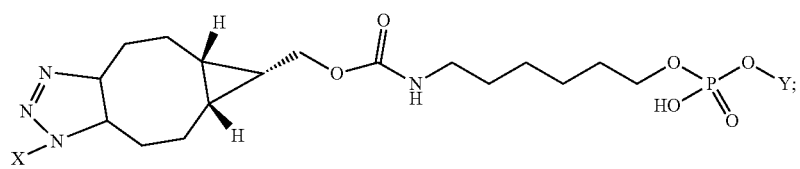

wherein
N—N═N represents an azido group of the GLP-1 receptor ligand conjugate moiety and X directly or indirectly attaches to the remainder of the GLP-1 receptor ligand conjugate moiety; and
Y directly or indirectly attaches to the oligonucleotide.

In certain embodiments, a composition comprises at least one compound described herein. In certain embodiments, a pharmaceutical composition comprises at least one compound described herein and a pharmaceutically acceptable excipient.

In certain embodiments, a method of modulating the expression of a nucleic acid target in a cell comprises contacting the cell with the compound of any of the aforementioned embodiments, thereby modulating expression of the nucleic acid target in the cell. In certain embodiments, the cell expresses GLP-1 receptor on the surface of the cell. In certain embodiments, the cell is a pancreatic cell, such as a beta-islet cell. In certain embodiments, the cell is a pituitary cell, leptomeninges cell, central nervous system (CNS) cell, stomach cell, intestinal cell, duodenum cell, ileum cell, colon cell, breast cell, lung cell, heart cell, thyroid cell, or kidney cell. In certain embodiments, the cell expressing GLP-1 receptor on its surface is a cancer cell. In certain embodiments, the cancer is an endocrine cancer including, but not limited to, pheochromocytoma, paraganglioma, medullary thyroid carcinoma, adrenal cortical adenoma, parathyroid carcinoma, and pituitary adenoma. In certain embodiments, the cancer is a nervous system cancer including, but not limited to, meningioma, astrocytoma, glioblastoma, ependymoma, and schwannoma. In certain embodiments, the cancer is an embroyic cancer including, but not limited to, medulloblastoma, nephroblastoma, and neuroblastoma. In certain embodiments, the cancer includes, but is not limited to, ovarian cancer, prostate cancer, breast cancer, colorectal cancer, gastric cancer, pancreatic cancer, cholangiocellular cancer, liver cancer, lung cancer, and lymphoma. In certain embodiments, contacting the cell with the compound of any of the aforementioned embodiments inhibits expression of the nucleic acid target. In certain embodiments, the nucleic acid target is pre-mRNA, mRNA, non-coding RNA, or miRNA. In certain embodiments, the cell is in an animal.

In certain embodiments, a method of modulating the expression of a nucleic acid target in an animal comprises administering to the animal the compound of any of the aforementioned embodiments, thereby modulating expression of the nucleic acid target in the animal. In certain embodiments, the expression of the nucleic acid target is modulated in a cell of the animal that expresses GLP-1 receptor on the surface of the cell. In certain embodiments, the expression of the nucleic acid target is modulated in a pancreatic cell, such as a beta-islet cell, of the animal. In certain embodiments, the cell is a pancreatic cell, such as a beta-islet cell. In certain embodiments, the cell is a pituitary cell, leptomeninges cell, duodenum cell, ileum cell, colon cell, breast cell, lung cell, or kidney cell. In certain embodiments, the cell expressing GLP-1 receptor on its surface is a cancer cell. In certain embodiments, the cancer is an endocrine cancer including, but not limited to, pheochromocytoma, paraganglioma, medullary thyroid carcinoma, adrenal cortical adenoma, parathyroid carcinoma, and pituitary adenoma. In certain embodiments, the cancer is a nervous system cancer including, but not limited to, meningioma, astrocytoma, glioblastoma, ependymoma, and schwannoma. In certain embodiments, the cancer is an embroyic cancer including, but not limited to, medulloblastoma, nephroblastoma, and neuroblastoma. In certain embodiments, the cancer includes, but is not limited to, ovarian cancer, prostate cancer, breast cancer, colorectal cancer, gastric cancer, pancreatic cancer, cholangiocellular cancer, liver cancer, lung cancer, and lymphoma. In certain embodiments, administering the compound inhibits expression of the nucleic acid target in the animal. In certain embodiments, the nucleic acid target is pre-mRNA, mRNA, non-coding RNA, or miRNA.

Also provided herewith is the use of a compound as described herein for the manufacture of a medicament in the treatment of cancer. Also provided herewith is a compound as described herein for use in the treatment of cancer.

In certain embodiments, a method of preparing a compound comprises reacting:

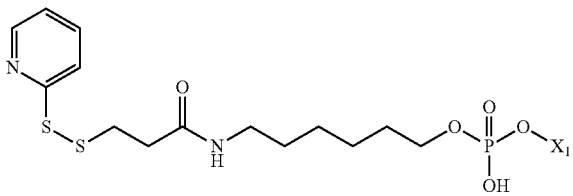

with a GLP-1 peptide; wherein $X_1$ is an oligonucleotide and the compound is a GLP-1 peptide conjugated oligonucleotide.

In certain embodiments, a method of preparing a compound comprises:

reacting an oligonucleotide comprising a hexamethyl linker and a terminal amine at the 5' end of the oligonucleotide with 3-(2-Pyridyldithio propionic acid N-hydroxysuccinimide ester) having the formula:

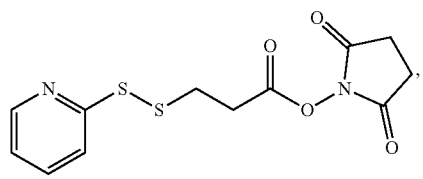 [SMILES: O=C(CCSSc1ccccn1)ON1C(=O)CCC1=O]

thereby yielding Compound 2 having the formula:

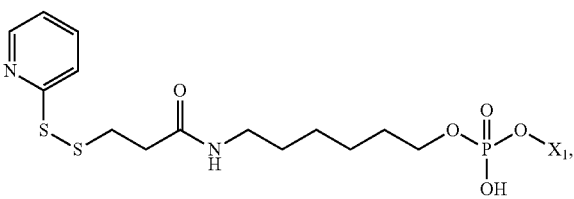

wherein $X_1$ is the oligonucleotide; and
reacting Compound 2 with GLP-1 peptide, thereby yielding the GLP-1 peptide conjugated oligonucleotide having the formula:

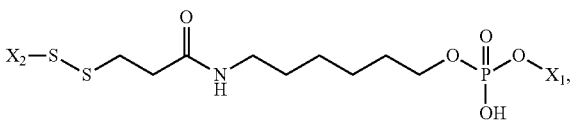

wherein $X_1$ is the oligonucleotide and $X_2$ is the GLP-1 peptide.

In certain embodiments, a method of preparing a GLP-1 peptide conjugated oligonucleotide comprises:

mixing a solution comprising an oligonucleotide comprising a hexamethyl linker and a terminal amine at the 5' end of the oligonucleotide with a solution comprising 3-(2-Pyridyldithio propionic acid N-hydroxysuccinimide ester) having the formula:

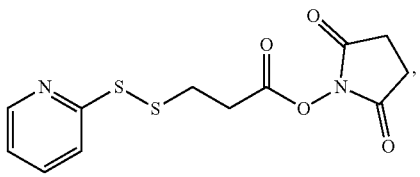 [SMILES: O=C(CCSSc1ccccn1)ON1C(=O)CCC1=O]

thereby yielding Compound 2 having the formula:

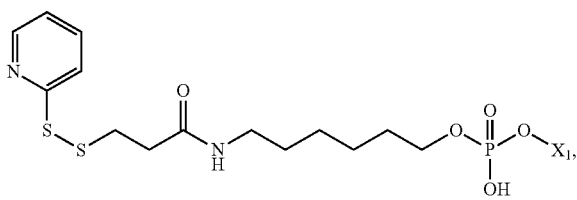

wherein $X_1$ is the oligonucleotide; and
mixing a solution comprising Compound 2 with a solution comprising GLP-1 peptide, thereby yielding the GLP-1 peptide conjugated oligonucleotide having the formula:

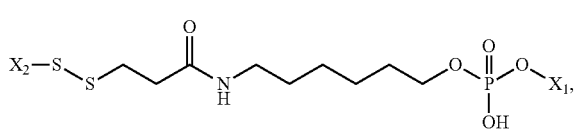

wherein $X_1$ is the oligonucleotide and $X_2$ is the GLP-1 peptide.

In certain embodiments, the solution comprising the oligonucleotide comprises sodium phosphate buffer and the solution comprising 3-(2-Pyridyldithio propionic acid N-hydroxysuccinimide ester) comprises dimethylformamide.

In certain embodiments, the solutions are mixed at room temperature.

In certain embodiments, the solution comprising Compound 2 further comprises acetonitrile and $NaHCO_3$ and has a pH of about 8.0.

In certain embodiments, the solution comprising GLP-1 peptide further comprises dimethylformamide.

In any of the aforementioned methods of preparing a compound or GLP-1 peptide conjugated oligonucleotide, the GLP-1 peptide can comprise an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% homologous to an equal length portion of the amino acid sequence of any of SEQ ID NOs: 1-57.

In any of the aforementioned methods of preparing a compound or GLP-1 peptide conjugated oligonucleotide, the GLP-1 peptide can comprise an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% identical to an equal length portion of the amino acid sequence of any of SEQ ID NOs: 1-57.

In any of the aforementioned methods of preparing a compound or GLP-1 peptide conjugated oligonucleotide, the GLP-1 peptide can be 8 to 50 amino acids in length and is at least 60%, at least 65%, at least 70%, at least 75%, at least 80%, at least 85%, at least 90%, at least 95%, or 100% homologous over its entire length to the amino acid sequence of any of SEQ ID NOs: 1-57.

In any of the aforementioned methods of preparing a compound or GLP-1 peptide conjugated oligonucleotide, the GLP-1 peptide can be at least 60%, at least 65%, at least 70%, at least 75%, at least 80%, at least 85%, at least 90%, at least 95%, or 100% identical over its entire length to the amino acid sequence of any of SEQ ID NOs: 1-57.

In any of the aforementioned methods of preparing a compound or GLP-1 peptide conjugated oligonucleotide, the GLP-1 peptide can comprise an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% homologous to an equal length portion of the amino acid sequence of GLP-1(7-37): HAEGTFTSDVSSYLEGQAAKEFIAWLVKGRG, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 1).

In any of the aforementioned methods of preparing a compound or GLP-1 peptide conjugated oligonucleotide, the GLP-1 peptide can comprise an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% identical to an equal length portion of the amino acid sequence of GLP-1(7-37).

In any of the aforementioned methods of preparing a compound or GLP-1 peptide conjugated oligonucleotide, the GLP-1 peptide can be 8 to 50 amino acids in length and is at least 60%, at least 65%, at least 70%, at least 75%, at least 80%, at least 85%, at least 90%, at least 95%, or 100% homologous over its entire length to the amino acid sequence of GLP-1(7-37) (SEQ ID NO: 1).

In any of the aforementioned methods of preparing a compound or GLP-1 peptide conjugated oligonucleotide, the GLP-1 peptide can be at least 60%, at least 65%, at least 70%, at least 75%, at least 80%, at least 85%, at least 90%, at least 95%, or 100% identical over its entire length to the amino acid sequence of GLP-1(7-37) (SEQ ID NO: 1).

In any of the aforementioned methods of preparing a compound or GLP-1 peptide conjugated oligonucleotide, the GLP-1 peptide can comprise the amino acid sequence of GLP-1(7-37) (SEQ ID NO: 1).

In any of the aforementioned methods of preparing a compound or GLP-1 peptide conjugated oligonucleotide, the GLP-1 peptide can consist of the amino acid sequence of GLP-1(7-37) (SEQ ID NO: 1).

In any of the aforementioned methods of preparing a compound or GLP-1 peptide conjugated oligonucleotide, the GLP-1 peptide can comprise the amino acid sequence of GLP-1(7-36)amide: HAEGTFTSDVSSYLEGQAAKEFI-AWLVKGR-NH$_2$, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ (SEQ ID NO: 2).

In any of the aforementioned methods of preparing a compound or GLP-1 peptide conjugated oligonucleotide, the GLP-1 peptide can consist of the amino acid sequence of GLP-1(7-36)amide (SEQ ID NO: 2).

In any of the aforementioned methods of preparing a compound or GLP-1 peptide conjugated oligonucleotide, the GLP-1 peptide can comprise the amino acid sequence of GLP-1(7-36): HAEGTFTSDVSSYLEGQAAKEFI-AWLVKGR, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQ ID NO: 2).

In any of the aforementioned methods of preparing a compound or GLP-1 peptide conjugated oligonucleotide, the GLP-1 peptide can comprise the amino acid sequence: EGTFTSDVSSYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3).

In any of the aforementioned methods of preparing a compound or GLP-1 peptide conjugated oligonucleotide, the GLP-1 peptide can consist of the amino acid sequence: EGTFTSDVSSYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3).

In any of the aforementioned methods of preparing a compound or GLP-1 peptide conjugated oligonucleotide, the GLP-1 peptide can comprise the amino acid sequence: EGTFTSDVSSYLEEQAAKEFIAWLVKG, Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4).

In any of the aforementioned methods of preparing a compound or GLP-1 peptide conjugated oligonucleotide, the GLP-1 peptide can consist of the amino acid sequence: EGTFTSDVSSYLEEQAAKEFIAWLVKG, Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4).

In any of the aforementioned methods of preparing a compound or GLP-1 peptide conjugated oligonucleotide, the GLP-1 peptide can comprise the amino acid sequence of any of SEQ ID NOs: 1-57.

In any of the aforementioned methods of preparing a compound or GLP-1 peptide conjugated oligonucleotide, the GLP-1 peptide can consist of the amino acid sequence of any of SEQ ID NOs: 1-57.

In any of the aforementioned methods of preparing a compound or GLP-1 peptide conjugated oligonucleotide, the GLP-1 peptide can comprise the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro- Pro-Ser-Cys (SEQ ID NO: 22), wherein Aib is aminoisobutyric acid.

In any of the aforementioned methods of preparing a compound or GLP-1 peptide conjugated oligonucleotide, the GLP-1 peptide can consist of the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro- Pro-Ser-Cys (SEQ ID NO: 22), wherein Aib is aminoisobutyric acid.

In any of the aforementioned methods of preparing a compound or GLP-1 peptide conjugated oligonucleotide, the GLP-1 peptide can comprise the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro- Pro-Ser-Pen (SEQ ID NO: 23), wherein Aib is aminoisobutyric acid and Pen is penicillamine.

In any of the aforementioned methods of preparing a compound or GLP-1 peptide conjugated oligonucleotide, the GLP-1 peptide can consist of the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro- Pro-Ser-Pen (SEQ ID NO: 23), wherein Aib is aminoisobutyric acid and Pen is penicillamine.

In any of the aforementioned methods of preparing a compound or GLP-1 peptide conjugated oligonucleotide, the GLP-1 peptide can comprise a reactive sulfur moiety.

In any of the aforementioned methods of preparing a compound or GLP-1 peptide conjugated oligonucleotide, the GLP-1 peptide can comprise penicillamine.

In any of the aforementioned methods of preparing a compound or GLP-1 peptide conjugated oligonucleotide, the penicillamine can be linked to the C-terminus of the GLP-1 peptide.

Certain Compounds Comprising an Oligonucleotide

In certain embodiments, compounds described herein can be antisense compounds. In certain embodiments, the antisense compound comprises or consists of an oligomeric compound. In certain embodiments, the oligomeric compound comprises a oligonucleotide, such as a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 12-30 linked nucleosides in length and the second modified oligonucleotide is 12-30 linked nucleosides in length. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

In certain embodiments, a compound comprises a double-stranded duplex comprising (i) a first strand comprising a modified oligonucleotide, optionally a conjugate linker, and a GLP-1 receptor ligand conjugate moiety, and (ii) a second strand complementary to the first strand. In certain embodiments, a compound comprises a double-stranded duplex comprising (i) a first strand comprising the modified oligonucleotide, optionally a conjugate linker, and a GLP-1 receptor ligand conjugate moiety, and (ii) a second strand complementary to the first strand; wherein the first strand is complementary to a RNA transcript. In certain embodiments, a compound comprises a double-stranded duplex comprising (i) a first strand comprising a modified oligonucleotide, optionally a conjugate linker, and a GLP-1 receptor ligand conjugate moiety, and (ii) a second strand complementary to the first strand; wherein the second strand is complementary to a RNA transcript.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound described herein comprises an oligonucleotide 14 to 30 linked subunits in length. In certain embodiments, a compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to a nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. (Proc. Natl. Acad. Sci. USA 89:7305-7309, 1992; Gautschi et al. *J Natl. Cancer Inst.* 93:463-471, March 2001; Maher and Dolnick *Nuc. Acid. Res.* 16:3341-3358, 1988). However, seemingly small changes in oligonucleotide sequence, chemistry and motif can make large differences in one or more of the many properties required for clinical development (Seth et al. *J. Med. Chem.* 2009, 52, 10; Egli et al. *J Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the compound that are beneficial for use as a therapeutic or research tool. In certain embodiments, radioactive isotopic substitutions may make the compound suitable for research or diagnostic purposes, such as an imaging assay.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is in a cell expressing GLP-1 receptor. In certain embodiments, the GLP-1 receptor expressing cell is a pancreatic cell, such as a beta islet cell.

Hybridization

In some embodiments, hybridization occurs between a compound disclosed herein and a target nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a target nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a target nucleic acid may be tolerated provided that the compound remains able to specifically hybridize to a target nucleic acid. Moreover, a compound may hybridize over one or more segments of a target nucleic acid such that intervening or adjacent segments are not involved in the hybridization event (e.g., a loop structure, mismatch or hairpin structure).

In certain embodiments, the compounds provided herein, or a specified portion thereof, are, are at least, or are up to 70%, 80%, 85%, 86%, 87%, 88%, 89%, 90%, 91%, 92%, 93%, 94%, 95%, 96%, 97%, 98%, 99%, or 100% complementary to a target nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a target nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a target nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 1, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a target nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a target nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the-compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ISIS or ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, are at least, or are up to 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ISIS or ION number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 1, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearlynon-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE")

and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 91999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

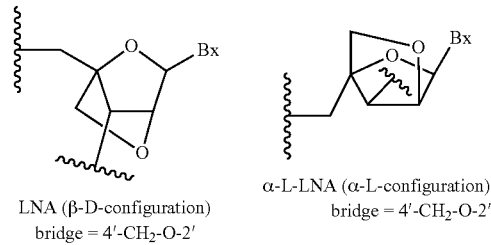

LNA (β-D-configuration)
bridge = 4'-CH$_2$-O-2'

α-L-LNA (α-L-configuration)
bridge = 4'-CH$_2$-O-2'

α-L-methyleneoxy (4'-CH$_2$—O—2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

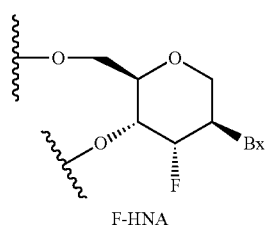

F-HNA ("F-HNA", see e.g., Swayze et al., U.S. Pat. No. 8,088,904; Swayze et al., U.S. Pat. No. 8,440,803; Swayze et al., U.S.; and Swayze et al., U.S. Pat. No. 9,005,906, F-HNA can also be referred to as a F-THP or 3'-fluoro tetrahydropyran), and nucleosides comprising additional modified THP compounds having the formula:

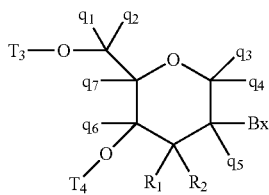

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure

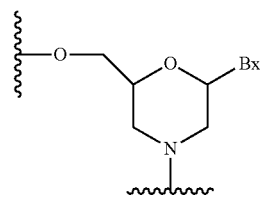

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimi-dines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C=C—$CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Frochler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

In certain embodiments, compounds targeted to a target nucleic acid comprise one or more modified nucleobases. In certain embodiments, the modified nucleobase is 5-methylcytosine. In certain embodiments, each cytosine is a 5-methylcytosine.

3. Modified Internucleoside Linkages

The naturally occurring internucleoside linkage of RNA and DNA is a 3' to 5' phosphodiester linkage In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a target nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N(CH3)-O—CH2-), thiodiester, thionocarbamate (—O—C(=O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(=O)—N(H)-5'), amide-4 (3'-CH2-N(H)—C(=O)-5'), formacetal (3'-O—CH2-O—5'), methoxypropyl, andthioformacetal (3'-S—CH2-O—5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

4. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

5. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

GLP-1 Receptor Ligand Conjugate Moieties

In certain embodiments, a compound comprises an oligonucleotide and GLP-1 receptor ligand conjugate moiety. In certain embodiments, a compound comprises an oligonucleotide, conjugate linker, and GLP-1 receptor ligand conjugate moiety. In certain embodiments, the conjugate linker links the GLP-1 receptor ligand conjugate moiety to the oligonucleotide. In certain embodiments, the oligonucleotide is a modified oligonucleotide. In certain embodiments, the GLP-1 receptor ligand conjugate moiety comprises a small molecule, aptamer, antibody, or peptide.

1. Certain GLP-1 Receptor Small Molecule Conjugate Moieties

In certain embodiments, a compound comprises an oligonucleotide and a small molecule conjugate moiety capable of binding to GLP-1 receptor. In certain embodiments, a compound comprises an oligonucleotide, conjugate linker, and small molecule conjugate moiety capable of binding to GLP-1 receptor. In certain embodiments, the oligonucleotide is a modified oligonucleotide.

Any small molecule conjugate moiety capable of binding to GLP-1 receptor known in the art can be used in several embodiments. For example, in certain embodiments the small molecule conjugate moiety capable of binding to GLP-1 receptor is a small molecule GLP-1 receptor antagonist described in Willard et al., "Small Molecule Drug Discovery at the Glucagon-like Peptide-1 Receptor," *Experimental Diabetes Research* Vol. 2012 pgs. 1-9; Sloop et al., "Novel Small Molecule Glucagon-Like Peptide-1 Receptor Agonist Stimulates Insulin Secretion in Rodents and From Human Islets," Diabetes Vol, 59, 2010 pgs. 3099-3107; Knudsen et al., "Small-molecule agonists for the glucagon-like peptide 1 receptor," *PNAS* 2007 Jan. 16; 104(3):937-42; or Wang et al., "Non-peptidic glucose-like peptide-1 receptor agonists: aftermath of a serendipitous discovery," *Acta Pharmacologica Sinica* (2010) 31: 1026-1030; which are incorporated by reference herein in their entireties.

In certain embodiments, the small molecule conjugate moiety capable of binding to GLP-1 receptor has any of the following formulas:

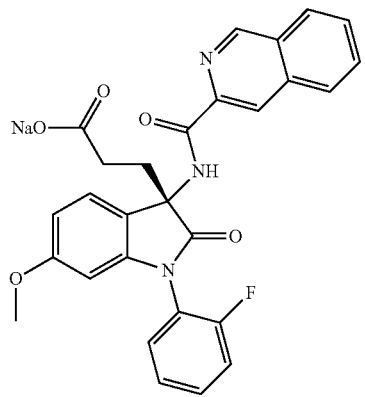
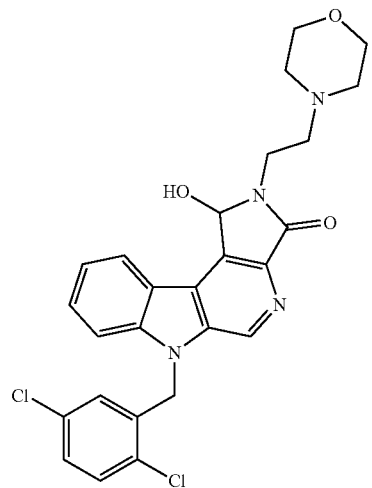
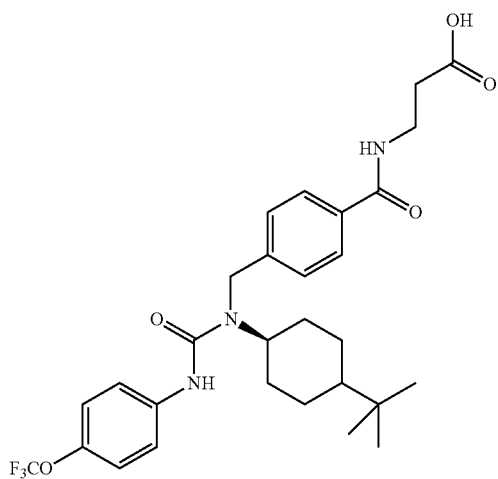
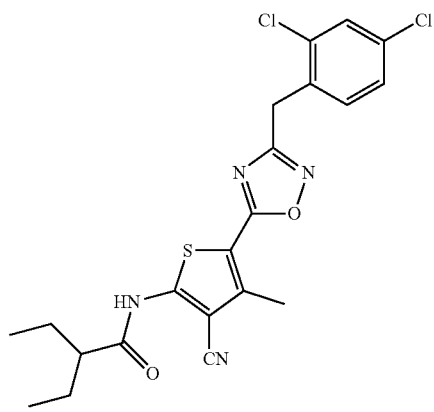

-continued
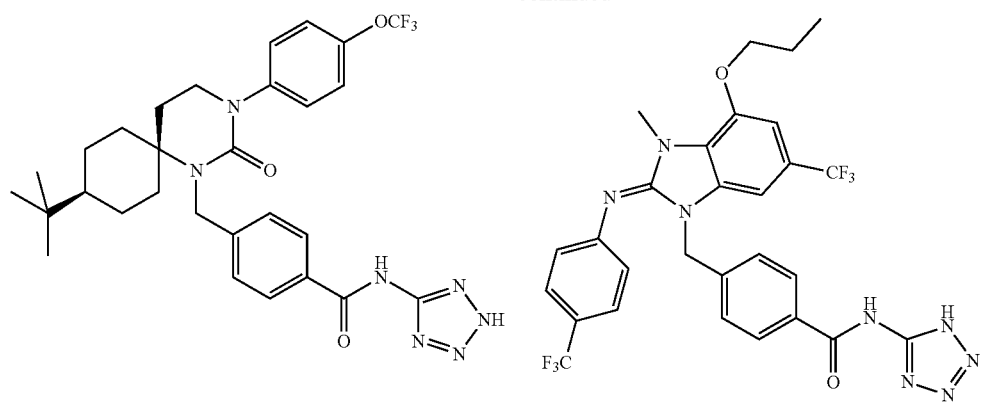
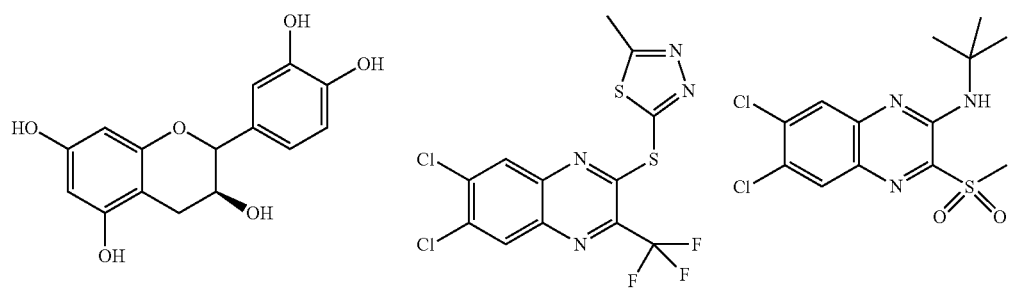
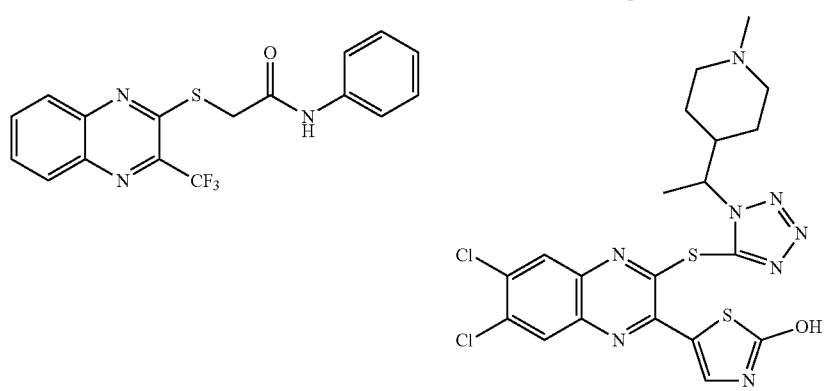
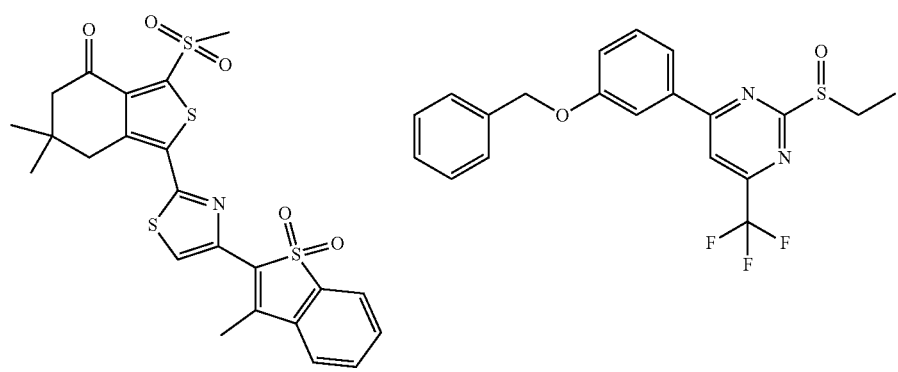

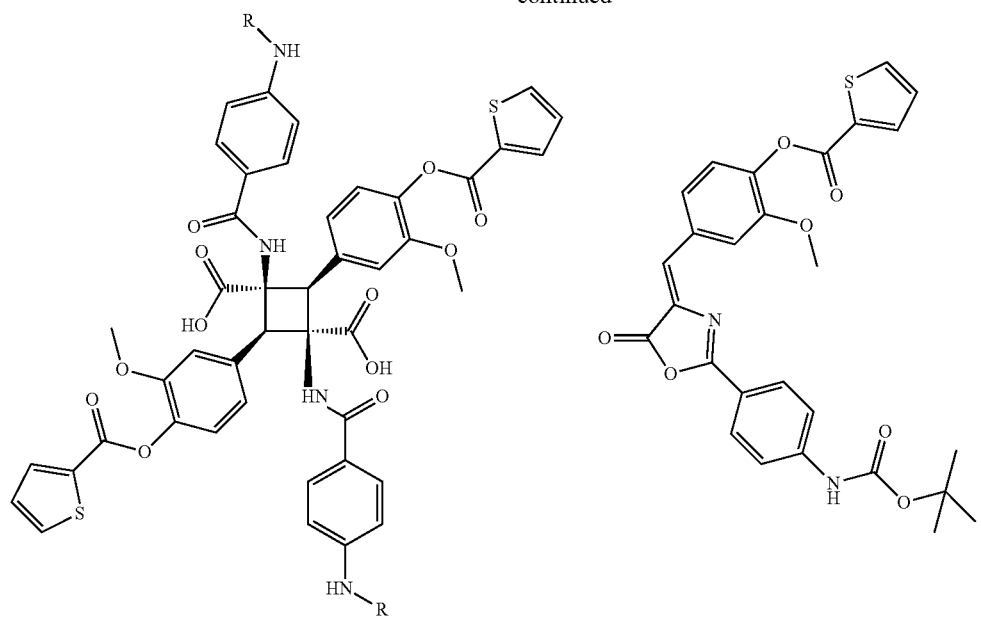
R = Boc (Boc-5)
R = CO-cyclopentyl (S4P)
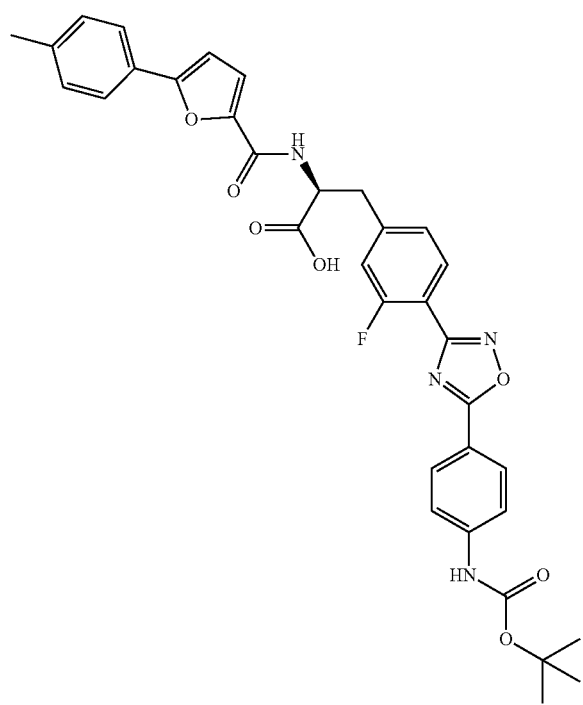

-continued

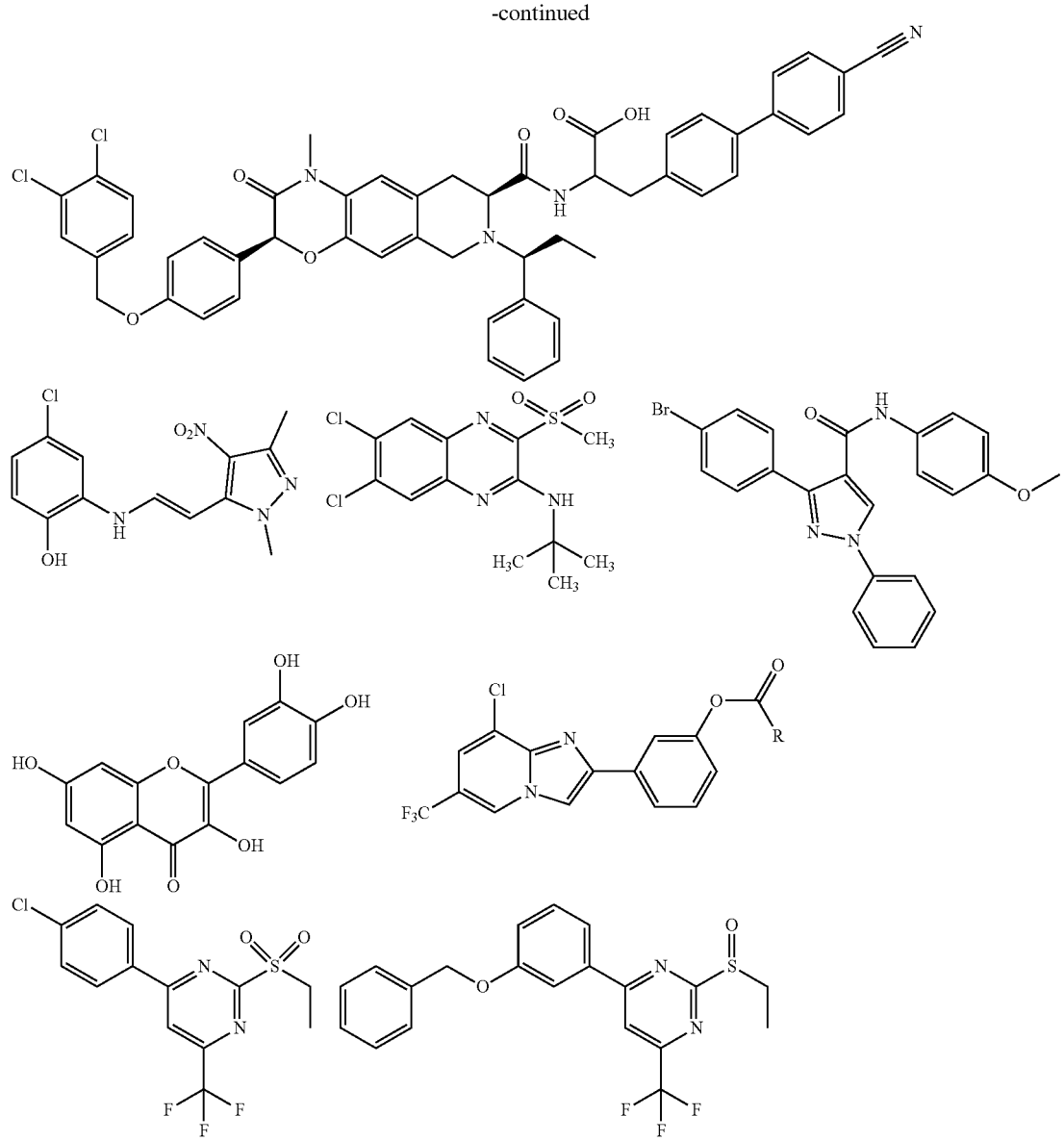

2. Certain GLP-1 Receptor Antibody Conjugate Moieties

In certain embodiments, a compound comprises an oligonucleotide and an antibody or fragment thereof capable of binding to GLP-1 receptor. In certain embodiments, a compound comprises an oligonucleotide, conjugate linker, and an antibody or fragment thereof capable of binding to GLP-1 receptor. In certain embodiments, the oligonucleotide is a modified oligonucleotide. Any antibody or fragment thereof capable of binding to GLP-1 receptor known in the art can be used in several embodiments. In certain embodiments, a compound comprises an oligonucleotide and an antibody or fragment thereof capable of binding to GLP-1 receptor described in WO 2005018536, US 20060275288, U.S. Pat. No. 8,389,689, or WO2011056644, which are incorporated by reference herein in their entireties. In certain embodiments, a compound comprises an oligonucleotide, a conjugate linker, and an antibody or fragment thereof capable of binding to GLP-1 receptor described in WO 2005018536, US 20060275288, U.S. Pat. No. 8,389,689, or WO2011056644, which are incorporated by reference herein in their entireties.

3. Certain GLP-1 Peptide Conjugate Moieties

In certain embodiments, a compound comprises an oligonucleotide and a GLP-1 peptide or fragment or mutant thereof. In certain embodiments, a compound comprises an oligonucleotide, conjugate linker, and GLP-1 peptide or fragment or mutant thereof. In certain embodiments, the oligonucleotide is a modified oligonucleotide. Any GLP-1 peptide or fragment or mutant thereof known in the art can be used in several embodiments. In certain embodiments, a compound comprises an oligonucleotide and a GLP-1 peptide described in US 20140206607; U.S. Pat. Nos. 9,187, 522; 8,329,419; or WO 2007/124461, which are incorporated by reference herein in their entireties. In certain embodiments, a compound comprises an oligonucleotide, conjugate linker, and GLP-1 peptide described in US 20140206607; U.S. Pat. Nos. 9,187,522; 8,329,419; or WO 2007/124461, which are incorporated by reference herein in their entireties.

In certain embodiments, a compound comprises an oligonucleotide and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% homologous to an equal length portion of the amino acid sequence of GLP-1(7-37): HAEGTFTSDVS-SYLEGQAAKEFIAWLVKGRG, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 1). In certain embodiments, a compound comprises an oligonucleotide and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% homologous to an equal length portion of the amino acid sequence of GLP-1(7-37): HAEGTFTSDVS-SYLEGQAAKEFIAWLVKGRG-NH$_2$ (SEQ ID NO: 1), wherein NH$_2$ indicates the C-terminal amide.

In certain embodiments, a compound comprises an oligonucleotide, conjugate linker, and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% homologous to an equal length portion of the amino acid sequence of GLP-1(7-37): HAEGTFTSDVSSYLEGQAAKEFIAWLVKGRG, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 1). In certain embodiments, a compound comprises an oligonucleotide, conjugate linker, and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% homologous to an equal length portion of the amino acid sequence of GLP-1 (7-37): HAEGTFTSDVSSYLEGQAAKEFIAWLVKGRG-NH$_2$ (SEQ ID NO: 1), wherein NH$_2$ indicates the C-terminal amide.

In certain embodiments, a compound comprises an oligonucleotide and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% identical to an equal length portion of the amino acid sequence of GLP-1(7-37). In certain embodiments, a compound comprises an oligonucleotide, conjugate linker, and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% identical to an equal length portion of the amino acid sequence of GLP-1(7-37).

In certain embodiments, a compound comprises an oligonucleotide and a GLP-1 peptide conjugate moiety 8 to 50 amino acids in length that is at least 60%, at least 65%, at least 70%, at least 75%, at least 80%, at least 85%, at least 90%, at least 95%, or 100% homologous over its entire length to the amino acid sequence of GLP-1(7-37) (SEQ ID NO: 1). In certain embodiments, a compound comprises an oligonucleotide, conjugate linker, and a GLP-1 peptide conjugate moiety 8 to 50 amino acids in length that is at least 60%, at least 65%, at least 70%, at least 75%, at least 80%, at least 85%, at least 90%, at least 95%, or 100% homologous over its entire length to the amino acid sequence of GLP-1(7-37) (SEQ ID NO: 1).

In certain embodiments, a compound comprises an oligonucleotide and a GLP-1 peptide conjugate moiety 8 to 50 amino acids in length that is at least 60%, at least 65%, at least 70%, at least 75%, at least 80%, at least 85%, at least 90%, at least 95%, or 100% identical over its entire length to the amino acid sequence of GLP-1(7-37) (SEQ ID NO: 1). In certain embodiments, a compound comprises an oligonucleotide, conjugate linker, and a GLP-1 peptide conjugate moiety 8 to 50 amino acids in length that is at least 60%, at least 65%, at least 70%, at least 75%, at least 80%, at least 85%, at least 90%, at least 95%, or 100% identical over its entire length to the amino acid sequence of GLP-1(7-37) (SEQ ID NO: 1).

In certain embodiments, a compound comprises an oligonucleotide and a GLP-1 peptide conjugate moiety comprising the amino acid sequence of GLP-1(7-37) (SEQ ID NO: 1). In certain embodiments, a compound comprises an oligonucleotide, conjugate linker, and a GLP-1 peptide conjugate moiety comprising the amino acid sequence of GLP-1(7-37) (SEQ ID NO: 1).

In certain embodiments, a compound comprises an oligonucleotide and a GLP-1 peptide conjugate moiety consisting of the amino acid sequence of GLP-1(7-37) (SEQ ID NO: 1). In certain embodiments, a compound comprises an oligonucleotide, conjugate linker, and a GLP-1 peptide conjugate moiety consisting of the amino acid sequence of GLP-1(7-37) (SEQ ID NO: 1).

In certain embodiments, a compound comprises an oligonucleotide and a GLP-1 peptide conjugate moiety comprising the amino acid sequence of GLP-1(7-36)amide: HAEGTFTSDV SSYLEGQAAKEFIAWLVKGR-NH$_2$, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ (SEQ ID NO: 2). In certain embodiments, a compound comprises an oligonucleotide, conjugate linker, and a GLP-1 peptide conjugate moiety comprising the amino acid sequence of GLP-1(7-36)amide: HAEGTFTSDV SSYLEGQAAKEFIAWLVKGR-NH$_2$, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ (SEQ ID NO: 2). In certain embodiments, a compound comprises an oligonucleotide and a GLP-1 peptide conjugate moiety comprising the amino acid sequence of GLP-1(7-36): HAE-GTFTSDV SSYLEGQAAKEFIAWLVKGR, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQ ID NO: 2). In certain embodiments, a compound comprises an oligonucleotide, conjugate linker, and a GLP-1 peptide conjugate moiety comprising the amino acid sequence of GLP-1(7-36): HAEGTFTSDV SSYLEGQAAKEFI-AWLVKGR, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQ ID NO: 2).

In certain embodiments, a compound comprises an oligonucleotide and a GLP-1 peptide conjugate moiety consisting of the amino acid sequence of GLP-1(7-36)amide (SEQ ID NO: 2). In certain embodiments, a compound comprises an oligonucleotide, conjugate linker, and a GLP-1 peptide conjugate moiety consisting of the amino acid sequence of GLP-1(7-36)amide (SEQ ID NO: 2). In certain embodiments, a compound comprises an oligonucleotide and a GLP-1 peptide conjugate moiety consisting of the amino acid sequence of GLP-1(7-36) (SEQ ID NO: 2). In certain embodiments, a compound comprises an oligonucleotide, conjugate linker, and a GLP-1 peptide conjugate moiety consisting of the amino acid sequence of GLP-1(7-36) (SEQ ID NO: 2).

In certain embodiments, a compound comprises an oligonucleotide and a GLP-1 peptide conjugate moiety comprising the amino acid sequence: EGTFTSDVSSYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3). In certain embodiments, a compound comprises an oligonucleotide and a GLP-1 peptide conjugate moiety comprising the amino acid sequence: EGTFTSDVSSYLEGQAAKEFIAWLVKG-NH$_2$ (SEQ ID NO: 3), wherein NH$_2$ indicates the C-terminal amide. In certain embodiments, a compound comprises an oligonucleotide, conjugate linker, and a GLP-1 peptide conjugate moiety comprising the amino acid sequence: EGTFTSDVSSYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3). In certain embodiments, a compound comprises an oligonucleotide, conjugate linker, and a GLP-1 peptide conjugate moiety comprising the amino acid sequence: EGTFTSDVSSYLEGQAAKEFIAWLVKG-NH$_2$ (SEQ ID NO: 3), wherein NH$_2$ indicates the C-terminal amide.

In certain embodiments, a compound comprises an oligonucleotide and a GLP-1 peptide conjugate moiety consisting of the amino acid sequence: EGTFTSDVSSYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3). In certain embodiments, a compound comprises an oligonucleotide and a GLP-1 peptide conjugate moiety consisting of the amino acid sequence: EGTFTSDVSSYLEGQAAKEFIAWLVKG-NH$_2$ (SEQ ID NO: 3), wherein NH$_2$ indicates the C-terminal amide. In certain embodiments, a compound comprises an oligonucleotide, conjugate linker, and a GLP-1 peptide conjugate moiety consisting of the amino acid sequence: EGTFTSDVSSYLEGQAAKEFIAWLVKG, which in conventional three-letter code is: Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 3). In certain embodiments, a compound comprises an oligonucleotide, conjugate linker, and a GLP-1 peptide conjugate moiety consisting of the amino acid sequence: EGTFTSDVSSYLEGQAAKEFIAWLVKG-NH$_2$ (SEQ ID NO: 3), wherein NH$_2$ indicates the C-terminal amide.

In certain embodiments, a compound comprises an oligonucleotide and a GLP-1 peptide conjugate moiety comprising the amino acid sequence: EGTFTSDVSSYLEEQAAKEFIAWLVKG, which in conventional three-letter code is: Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4). In certain embodiments, a compound comprises an oligonucleotide and a GLP-1 peptide conjugate moiety comprising the amino acid sequence: EGTFTSDVSSYLEEQAAKEFIAWLVKG-NH$_2$ (SEQ ID NO: 4), wherein NH$_2$ indicates the C-terminal amide. In certain embodiments, a compound comprises an oligonucleotide, conjugate linker, and a GLP-1 peptide conjugate moiety comprising the amino acid sequence: EGTFTSDVSSYLEEQAAKEFIAWLVKG, which in conventional three-letter code is: Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4). In certain embodiments, a compound comprises an oligonucleotide, conjugate linker, and a GLP-1 peptide conjugate moiety comprising the amino acid sequence: EGTFTSDVSSYLEEQAAKEFIAWLVKG-NH$_2$ (SEQ ID NO: 4), wherein NH$_2$ indicates the C-terminal amide.

In certain embodiments, a compound comprises an oligonucleotide and a GLP-1 peptide conjugate moiety consisting of the amino acid sequence: EGTFTSDVSSYLEEQAAKEFIAWLVKG, which in conventional three-letter code is: Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4). In certain embodiments, a compound comprises an oligonucleotide and a GLP-1 peptide conjugate moiety consisting of the amino acid sequence: EGTFTSDVSSYLEEQAAKEFIAWLVKG-NH$_2$ (SEQ ID NO: 4), wherein NH$_2$ indicates the C-terminal amide. In certain embodiments, a compound comprises an oligonucleotide, conjugate linker, and a GLP-1 peptide conjugate moiety consisting of the amino acid sequence: EGTFTSDVSSYLEEQAAKEFIAWLVKG, which in conventional three-letter code is: Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 4). In certain embodiments, a compound comprises an oligonucleotide, conjugate linker, and a GLP-1 peptide conjugate moiety consisting of the amino acid sequence: EGTFTSDVSSYLEEQAAKEFIAWLVKG-NH$_2$ (SEQ ID NO: 4), wherein NH$_2$ indicates the C-terminal amide.

In certain embodiments, a compound comprises an oligonucleotide, optionally a conjugate linker, and an analog of GLP-1 peptide conjugate moiety including, but not limited to, liraglutide (VICTOZA® from Novo Nordisk); albiglutide (SYNCRIA® from GlaxoSmithKline); taspoglutide (Hoffman La-Roche); LY2189265 (Eli Lilly and Company); LY2428757 (Eli Lilly and Company); desamino-His7,Arg26,Lys34-((nε(γ-Glu(N-α-hexadecanoyl)))-GLP-1(7-37); desamino-His7,Arg26,Lys34(np-octanoyl)-GLP-1(7-37); Arg26,34,Lys38(NF-(Q-carboxypentadecanoyl))-GLP-1(7-38); Arg26,34,Lys36(NF-(γ-Glu(N-α-hexadecanoyl)))-GLP-1(7-36); Aib8.35,Arg26,34, Phe31-GLP-1 (7-36)) (SEQ ID NO: 5); HXaa8EGTFTSDVSSYLEXaa22Xaa23AAKEFIXaa30WLXaa33Xaa34G Xaa36Xaa37; wherein Xaa8 is A, V, or G; Xaa22 is G, K, or E; Xaa23 is Q or K; Xaa30 is A or E; Xaa33 is V or K; Xaa34 is K, N, or R; Xaa36 is R or G; and Xaa37 is G, H, P, or absent (SEQ ID NO: 6); Arg34-GLP-1 (7-37) (SEQ ID NO: 7); Glu30-GLP-1 (7-37) (SEQ ID NO: 8); Lys22-GLP-1 (7-37) (SEQ ID NO: 9); Gly8.36,Glu22-GLP-1 (7-37) (SEQ ID NO: 10); Val8,Glu22,Gly36-GLP-1 (7-37) (SEQ ID NO: 11); Gly8.36,Glu22,Lys33,Asn34-GLP-1(7-37) (SEQ ID NO: 12); Val8,Glu22,Lys33,Asn34, Gly36-GLP-1 (7-37) (SEQ ID NO: 13); Gly8.36,Glu22, Pro37-GLP-1 (7-37) (SEQ ID NO: 14); Val8,Glu22, Gly36Pro37-GLP-1(7-37) (SEQ ID NO: 15); Gly8.36, Glu22,Lys33, Asn34,Pro37-GLP-1 (7-37) (SEQ ID NO: 16); Val8,Glu22,Lys33,Asn34,Gly36Pro37-GLP-1(7-37) (SEQ ID NO: 17); Gly8.36,Glu22-GLP-1(7-36) (SEQ ID NO: 18); Val8,Glu22,Gly36-GLP-1 (7-36) (SEQ ID NO: 19); Val8, Glu22,Asn34,Gly36-GLP-1 (7-36) (SEQ ID NO: 20); Gly8.36,Glu22,Asn34-GLP-1(7-36) (SEQ ID NO: 21). Any of the foregoing analogs may optionally be amidated.

In certain embodiments, a compound comprises an oligonucleotide, optionally a conjugate linker, and an analog of GLP-1 peptide conjugate moiety including, but not limited to, iraglutide, taspoglutide, exenatide, lixisenatide, semaglutide. These analogs are described in Lorenz M et al., "Recent progress and future options in the development of GLP-1 receptor agonists for the treatment of diabesity," *Bioorg Med Chem Lett.* 2013 Jul. 15; 23(14):4011-8, which is incorporated by reference herein in its entirety.

In certain embodiments, a compound comprises an oligonucleotide, optionally a conjugate linker, and a GLP-1 peptide conjugate moiety comprising or consisting of the amino acid sequence: H-AibEGTFTSDVSSYLEEQAAKE-FIAWLVKGGPSSGAPPPSC-NH$_2$ (SEQ ID NO: 22), wherein Aib is aminoisobutyric acid and NH$_2$ indicates the C-terminal amide. In certain embodiments, a compound comprises an oligonucleotide, optionally a conjugate linker, and a GLP-1 peptide conjugate moiety comprising or consisting of the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Cys (SEQ ID NO: 22) wherein Aib is aminoisobutyric acid.

In certain embodiments, a compound comprises an oligonucleotide, optionally a conjugate linker, and a GLP-1 peptide conjugate moiety comprising or consisting of the amino acid sequence: H-AibEGTFTSDVSSYLEEQAAKE-FIAWLVKGGPSSGAPPPSX-NH$_2$ (SEQ ID NO: 23), wherein Aib is aminoisobutyric acid, X is penicillamine, and NH$_2$ indicates the C-terminal amide. In certain embodiments, a compound comprises an oligonucleotide, optionally a conjugate linker, and a GLP-1 peptide conjugate moiety comprising or consisting of the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Pen (SEQ ID NO: 23), wherein Aib is aminoisobutyric acid and Pen is penicillamine.

In certain embodiments, a compound comprises an oligonucleotide, optionally a conjugate linker, and a GLP-1 peptide conjugate moiety comprising or consisting of the amino acid sequence: HAEGTFTSDVSSYLEGQAAKEFI-AWLVKGRC, which in conventional three-letter code is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Cys (SEQ ID NO: 24). In certain embodiments, a compound comprises an oligonucleotide, optionally a conjugate linker, and a GLP-1 peptide conjugate moiety comprising or consisting of the amino acid sequence: HAEGTFTSDVSSYLEGQAAKEFIAWLVKGRC-NH$_2$ (SEQ ID NO: 24), wherein NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNGGPSSGAPPPS (SEQ ID NO: 25). In certain embodiments, a compound comprises an oligonucleotide, optionally a conjugate linker, and a GLP-1 peptide conjugate moiety comprising or consisting of the amino acid sequence: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 25), wherein H indicates the N-terminus and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: AGEGTF TSDVSSYLEGQAAKEA-IAWLVKGGPSSGAPPPSC, which in conventional three-letter code is: Ala-Gly-Glu-Gly-Thr-Phe-Thr-Ser-Asp-Val-Ser-Ser-Tyr-Leu-Glu-Gly-Gln-Ala-Ala-Lys-Glu-Ala-Ile-Ala-Trp-Leu-Val-Lys-Gly-Gly-Pro-Ser-Ser-Gly-Ala-Pro-Pro- Pro-Ser-Cys (SEQ ID NO: 26). In certain embodiments, a compound comprises an oligonucleotide, optionally a conjugate linker, and a GLP-1 peptide conjugate moiety comprising or consisting of the amino acid sequence: AGEGTF TSDVSSYLEGQAAKEA-IAWLVKGGPSSGAPPPSC-NH$_2$ (SEQ ID NO: 26), wherein NH$_2$ indicates the C-terminal amide.

In certain embodiments, a compound comprises an oligonucleotide, optionally a conjugate linker, and a GLP-1 peptide conjugate moiety comprising or consisting of the amino acid sequence: AGEGTF TSDVSSYLEGQAAKEA-IAWLVKGGPSSGAPPPSX, wherein X is penicillamine, which in conventional three-letter code is: Ala-Gly-Glu-Gly-Thr-Phe-Thr-Ser-Asp-Val-Ser-Ser-Tyr-Leu-Glu-Gly-Gln-Ala-Ala-Lys-Glu-Ala-Ile-Ala-Trp-Leu-Val-Lys-Gly-Gly-Pro-Ser-Ser-Gly-Ala-Pro-Pro-Pro-Ser-Pen wherein Pen is penacillamine (SEQ ID NO: 27). In certain embodiments, a compound comprises an oligonucleotide, optionally a conjugate linker, and a GLP-1 peptide conjugate moiety comprising or consisting of the amino acid sequence: AGEGTFTSDVSSYLEGQAAKEA-IAWLVKGGPSSGAPPPSX-NH$_2$ (SEQ ID NO: 27), wherein X is penicillamine and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLV, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val (SEQ ID NO: 28), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKEFIAWLV-NH$_2$ (SEQ ID NO: 28), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVK, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys (SEQ ID NO: 29), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVK-NH$_2$ (SEQ ID NO: 29), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE- FIAWLVKG, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly (SEQ ID NO: 30), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVSSYLE-EQAAKEFIAWLVKG-NH$_2$ (SEQ ID NO: 30), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGG, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly (SEQ ID NO: 31), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVS-SYLEEQAAKEFIAWLVKGG-NH$_2$ (SEQ ID NO: 31), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGP, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro (SEQ ID NO: 32), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVS-SYLEEQAAKEFIAWLVKGGP-NH$_2$, (SEQ ID NO: 32), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPS, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser (SEQ ID NO: 33), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVS-SYLEEQAAKEFIAWLVKGGPS-NH$_2$(SEQ ID NO: 33), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSS, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser (SEQ ID NO: 34), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKEFIAWLVKGGPSS-NH$_2$ (SEQ ID NO: 34), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSG, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly (SEQ ID NO: 35), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKEFIAWLVKGGPSSG-NH$_2$ (SEQ ID NO: 35), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSGA, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala (SEQ ID NO: 36), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKEFIAWLVKGGPSSGA-NH$_2$ (SEQ ID NO: 36), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSGAP, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro (SEQ ID NO: 37), wherein Aib is aminoisobutyric acid. In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKEFI-AWLVKGGPSSGAP-NH$_2$ (SEQ ID NO: 37), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNGGPSSGAPPPSZ, which in conventional three-letter code is: His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-Zaa (SEQ ID NO: 38), wherein Z or Zaa is 4-azidonorleucine comprising:

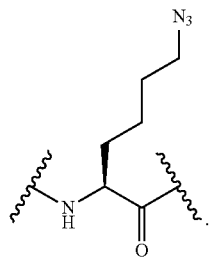 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNGGPSSGAPPPSZ-NH$_2$ (SEQ ID NO: 38), wherein NH$_2$ indicates the C-terminal amide and Z or Zaa is 4-azidonorleucine comprising:

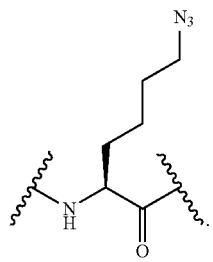 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVSSYLEGQAAKE-FIAWLVRGRGZ, which in conventional three-letter code is: His-Aib-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-Gly-Zaa (SEQ ID NO: 39), wherein Aib is aminoisobutyric acid and Z or Zaa is 4-azidonorleucine comprising:

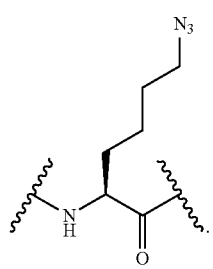 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVSSYLEGQAAKE-FIAWLVRGRGZ-NH$_2$ (SEQ ID NO: 39), wherein Aib is aminoisobutyric acid, NH$_2$ indicates the C-terminal amide, and Z or Zaa is 4-azidonorleucine comprising:

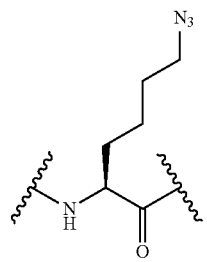

In certain embodiments, a compound comprises an oligonucleotide, optionally a conjugate linker, and a GLP-1 peptide conjugate moiety comprising or consisting of the amino acid sequence: HAibEGTFTSDVS-SYLEGQAANXEFIAWLVRGRG, which in conventional three-letter code is: His-Aib-Glu-Gly-Thr-Phe-Thr-Ser-Asp-Val-Ser-Ser-Tyr-Leu-Glu-Gly-Gln-Ala-Ala-Asn-Xaa-Glu-Phe-Ile-Ala-Trp-Leu-Val-Arg-Gly-Arg-Gly (SEQ ID NO: 40), wherein Aib is aminoisobutyric acid and X or Xaa is Lysine (5 azido pentanoic acid amide) having the formula:

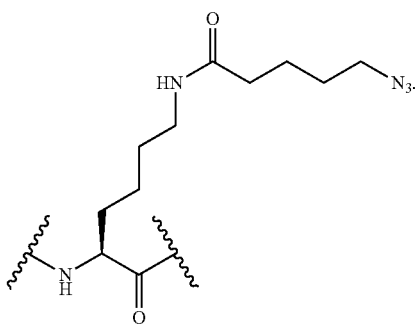 [SMILES: *N[C@@H](CCCCNC(=O)CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVS-SYLEGQAANXEFIAWLVRGRG-NH$_2$ (SEQ ID NO: 40), wherein Aib is aminoisobutyric acid, NH$_2$ indicates the C-terminal amide, and X or Xaa is Lysine (5 azido pentanoic acid amide) having the formula:

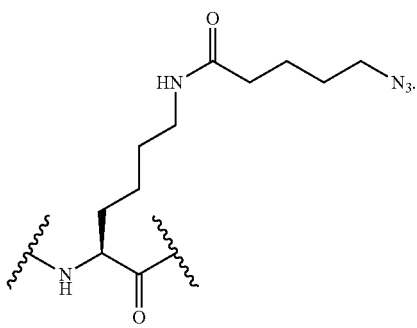 [SMILES: *N[C@@H](CCCCNC(=O)CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVSSYLEGQAAKE-FIAWLVK-AibRZ, which in conventional three-letter code is: His-Aib-Glu-Gly-Thr-Phe-Thr-Ser-Asp-Val-Ser-Ser-Tyr- Leu-Glu-Gly-Gln-Ala-Ala-Lys-Glu-Phe-Ile-Ala-Trp-Leu-Val-Lys-Aib-Arg-Zaa (SEQ ID NO: 41), wherein Aib is aminoisobutyric acid and Z or Zaa is 4-azidonorleucine comprising:

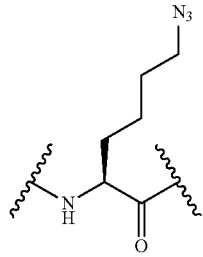

In certain embodiments, a compound comprises an oligonucleotide, optionally a conjugate linker, and a GLP-1 peptide conjugate moiety comprising or consisting of the amino acid sequence: HAibEGTFTSDVSSYLEGQAAKE-FIAWLVK-AibRZ-NH$_2$ (SEQ ID NO: 41), wherein Aib is aminoisobutyric acid, NH$_2$ indicates the C-terminal amide, and Z or Zaa is 4-azidonorleucine comprising:

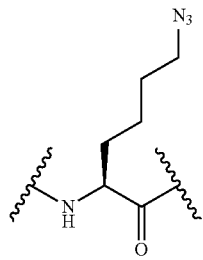

In certain embodiments, a compound comprises an oligonucleotide, optionally a conjugate linker, and a GLP-1 peptide conjugate moiety comprising or consisting of the amino acid sequence: HSEGTFTSDVSSYLEGQAAKEFI-AWLVKGRZ, which in conventional three-letter code is: His-Ser-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Zaa (SEQ ID NO: 42), wherein Z or Zaa is 4-azidonorleucine comprising:

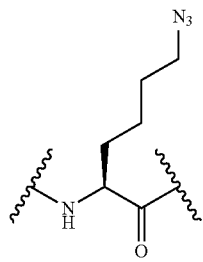

In certain embodiments, a compound comprises an oligonucleotide, optionally a conjugate linker, and a GLP-1 peptide conjugate moiety comprising or consisting of the amino acid sequence: HSEGTFTSDVSSYLEGQAAKEFI-AWLVKGRZ-NH$_2$ (SEQ ID NO: 42), wherein NH$_2$ indicates the C-terminal amide and Z or Zaa is 4-azidonorleucine comprising:

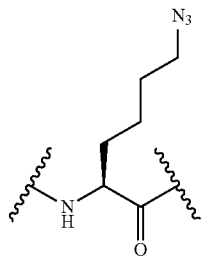

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSGAPPZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Zaa (SEQ ID NO: 43), wherein Aib is aminoisobutyric acid and Z or Zaa is 4-azidonorleucine comprising:

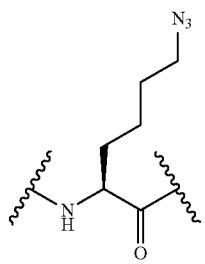

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSGAPPZ-NH$_2$ (SEQ ID NO: 43), wherein Aib is aminoisobutyric acid, NH$_2$ indicates the C-terminal amide, and Z or Zaa is 4-azidonorleucine comprising:

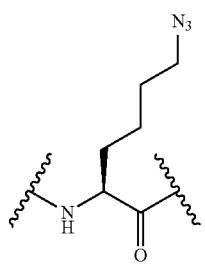

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Zaa (SEQ ID NO: 44), wherein Aib is aminoisobutyric acid and Z or Zaa is 4-azidonorleucine comprising:

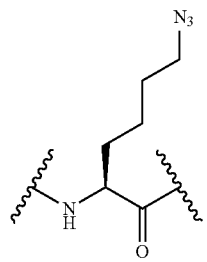

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSZ-NH$_2$ (SEQ ID NO: 44), wherein Aib is aminoisobutyric acid, NH$_2$ indicates the C-terminal amide, and Z or Zaa is 4-azidonorleucine comprising:

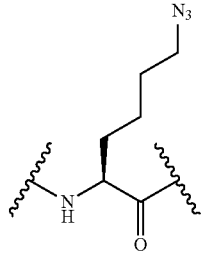

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Zaa (SEQ ID NO: 46), wherein Aib is aminoisobutyric acid and Z or Zaa is 4-azidonorleucine comprising:

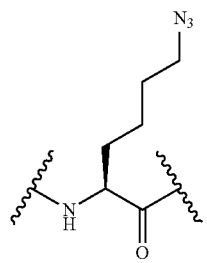

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Zaa (SEQ ID NO: 45), wherein Aib is aminoisobutyric acid and Z or Zaa is 4-azidonorleucine comprising:

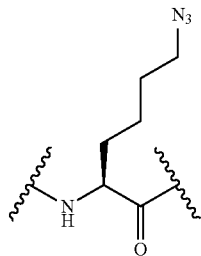

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVZ-NH$_2$ (SEQ ID NO: 46), wherein Aib is aminoisobutyric acid, NH$_2$ indicates the C-terminal amide, and Z or Zaa is 4-azidonorleucine comprising:

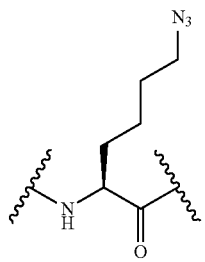

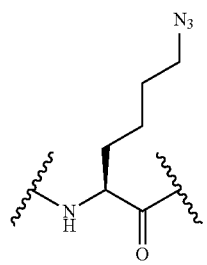

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKZ-NH$_2$ (SEQ ID NO: 45), wherein Aib is aminoisobutyric acid, NH$_2$ indicates the C-terminal amide, and Z or Zaa is 4-azidonorleucine comprising:

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVC, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Cys (SEQ ID NO: 47), wherein Aib is aminoisobutyric acid.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE- FIAWLVC-NH$_2$ (SEQ ID NO: 47), wherein Aib is aminoisobutyric acid and NH$_2$ indicates the C-terminal amide.

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Zaa (SEQ ID NO: 48), wherein Aib is aminoisobutyric acid and Z or Zaa is 4-azidonorleucine comprising:

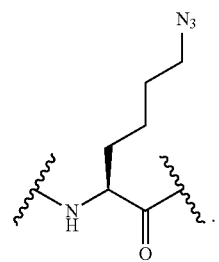 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLZ-NH$_2$ (SEQ ID NO: 48), wherein Aib is aminoisobutyric acid, NH$_2$ indicates the C-terminal amide, and Z or Zaa is 4-azidonorleucine comprising:

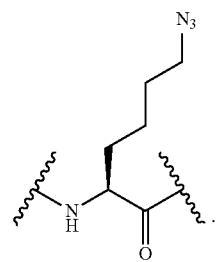 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Zaa (SEQ ID NO: 49), wherein Aib is aminoisobutyric acid and Z or Zaa is 4-azidonorleucine comprising:

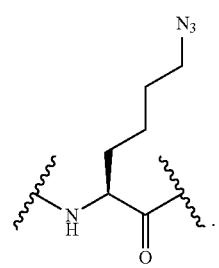 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWZ-NH$_2$ (SEQ ID NO: 49), wherein Aib is aminoisobutyric acid, NH$_2$ indicates the C-terminal amide, and Z or Zaa is 4-azidonorleucine comprising:

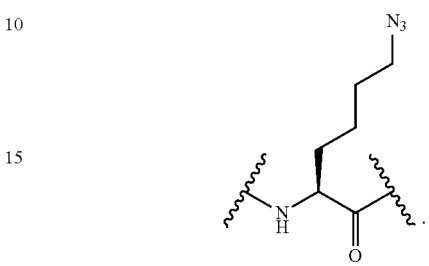

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Zaa (SEQ ID NO: 50), wherein Aib is aminoisobutyric acid and Z or Zaa is 4-azidonorleucine comprising:

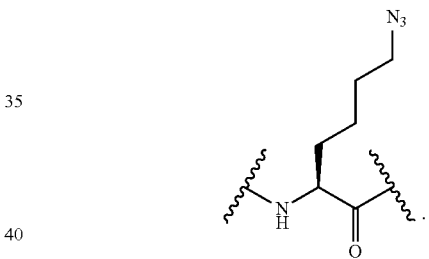

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAZ-NH$_2$ (SEQ ID NO: 50), wherein Aib is aminoisobutyric acid, NH$_2$ indicates the C-terminal amide, and Z or Zaa is 4-azidonorleucine comprising:

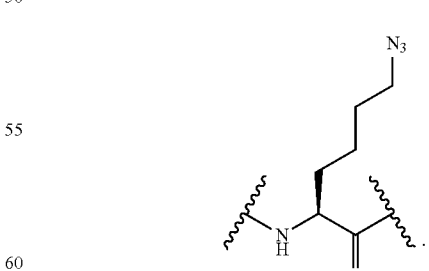

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNGZ, which in conventional three-letter code is: His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Zaa (SEQ ID NO: 51), wherein Z or Zaa is 4-azidonorleucine comprising:

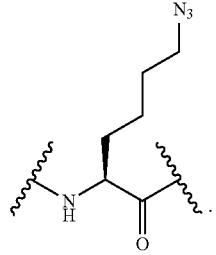

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNGZ-NH$_2$ (SEQ ID NO: 51), wherein NH$_2$ indicates the C-terminal amide, and Z or Zaa is 4-azidonorleucine comprising:

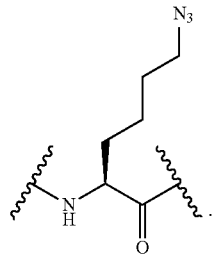 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNZ, which in conventional three-letter code is: His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Zaa (SEQ ID NO: 52), wherein Z or Zaa is 4-azidonorleucine comprising:

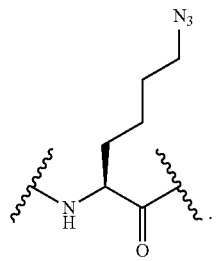 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNZ-NH$_2$ (SEQ ID NO: 52), wherein NH$_2$ indicates the C-terminal amide and Z or Zaa is 4-azidonorleucine comprising:

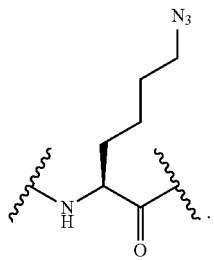 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKZ, which in conventional three-letter code is: His-Gly-Glu-Gly-Thr-Phe-Thr-Ser-Asp-Leu-Ser-Lys-Gln-Met-Glu-Glu-Glu-Ala-Val-Arg-Leu-Phe-Tle-Glu-Trp-Leu-Lys-Zaa (SEQ ID NO: 53), wherein Z or Zaa is 4-azidonorleucine comprising:

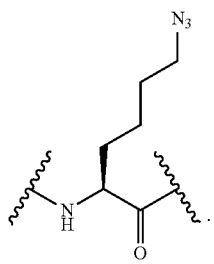 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKZ-NH$_2$ (SEQ ID NO: 53), wherein NH$_2$ indicates the C-terminal amide and Z or Zaa is 4-azidonorleucine comprising:

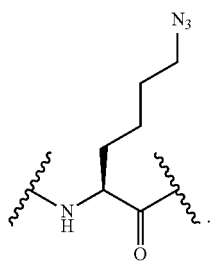 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLZ, which in conventional three-letter code is: His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Zaa (SEQ ID NO: 54), wherein Z or Zaa is 4-azidonorleucine comprising:

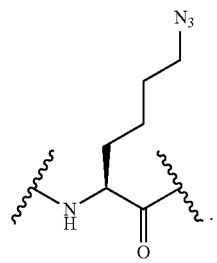 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLZ-NH$_2$ (SEQ ID NO: 54), wherein NH$_2$ indicates the C-terminal amide and Z or Zaa is 4-azidonorleucine comprising:

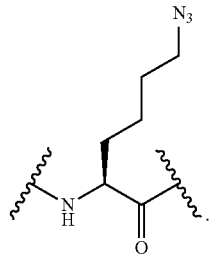 [SMILES: *N[C@@H](CCCCN=[N+]=[N-])C(*)=O]

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSGAPPPSZ, which in conventional three-letter code is: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Zaa (SEQ ID NO: 56), wherein Aib is aminoisobutyric acid and Z or Zaa is 4-azidonorleucine comprising:

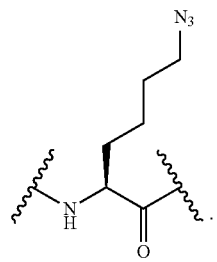 [SMILES: *N[C@@H](CCCCN=[N+]=[N-])C(*)=O]

In certain embodiments, a compound comprises an oligonucleotide and a GLP-1 peptide conjugate moiety comprising or consisting of the amino acid sequence: HGEGTFTSDLSKQMEEEAVRLFIEWZ, which in conventional three-letter code is: His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Zaa (SEQ ID NO: 55), wherein Z or Zaa is 4-azidonorleucine comprising:

In certain embodiments, a compound comprises an oligonucleotide, optionally a conjugate linker, and a GLP-1 peptide conjugate moiety comprising or consisting of the amino acid sequence: HAibEGTFTSDVSSYLEEQAAKE-FIAWLVKGGPSSGAPPPSZ-NH$_2$ (SEQ ID NO: 56), wherein Aib is aminoisobutyric acid, NH$_2$ indicates the C-terminal amide, and Z or Zaa is 4-azidonorleucine comprising:

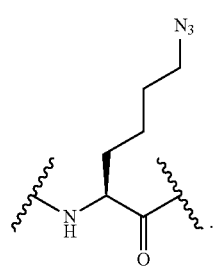

In certain embodiments, a compound comprises an oligonucleotide and a GLP-1 peptide conjugate moiety comprising or consisting of the amino acid sequence: HGEGTFTSDLSKQMEEEAVRLFIEWZ-NH$_2$ (SEQ ID NO: 55), wherein NH$_2$ indicates the C-terminal amide and Z or Zaa is 4-azidonorleucine comprising:

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNGGPSSGAPPPSC, which in conventional three-letter code is: His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-Cys (SEQ ID NO: 57).

In certain embodiments, a compound comprises an oligonucleotide, optionally a conjugate linker, and a GLP-1 peptide conjugate moiety comprising or consisting of the amino acid sequence: HGEGTFTSDLSKQMEEE-AVRLFIEWLKNGGPSSGAPPPSC-NH$_2$ (SEQ ID NO: 57), wherein NH$_2$ indicates the C-terminal amide.

In certain embodiments, a compound comprises an oligonucleotide and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% identical to an equal length portion of the amino acid sequence of any one of SEQ ID NOs: 1-57. In certain embodiments, a compound comprises an oligonucleotide, conjugate linker, and a GLP-1 peptide conjugate moiety comprising an at least 8, 9, 10, 11, 12, 13, 14, 15, 16, 17, 18, 19, 20, 21, 22, 23, 24, 25, 26, 27, 28, 29, 30, or 31 contiguous amino acid portion at least 60%, at least 65%, at least 70%, at least 75%, at least 80%, at least 85%, at least 90%, at least 95%, or 100% identical to an equal length portion of the amino acid sequence of any one of SEQ ID NOs: 1-57.

In certain embodiments, a compound comprises an oligonucleotide and a GLP-1 peptide conjugate moiety 8 to 50 amino acids in length that is at least 60%, at least 65%, at least 70%, at least 75%, at least 80%, at least 85%, at least 90%, at least 95%, or 100% homologous over its entire length to the amino acid sequence of any one of SEQ ID NOs: 1-57. In certain embodiments, a compound comprises an oligonucleotide, conjugate linker, and a GLP-1 peptide conjugate moiety 8 to 50 amino acids in length that is at least 60%, at least 65%, at least 70%, at least 75%, at least 80%, at least 85%, at least 90%, at least 95%, or 100% homologous over its entire length to the amino acid sequence of any one of SEQ ID NOs: 1-57.

In certain embodiments, a compound comprises an oligonucleotide and a GLP-1 peptide conjugate moiety 8 to 50 amino acids in length that is at least 60%, at least 65%, at least 70%, at least 75%, at least 80%, at least 85%, at least 90%, at least 95%, or 100% identical over its entire length to the amino acid sequence of any one of SEQ ID NOs: 1-57. In certain embodiments, a compound comprises an oligonucleotide, conjugate linker, and a GLP-1 peptide conjugate moiety 8 to 50 amino acids in length that is at least 60%, at least 65%, at least 70%, at least 75%, at least 80%, at least 85%, at least 90%, at least 95%, or 100% identical over its entire length to the amino acid sequence of any one of SEQ ID NOs: 1-57.

In certain embodiments, a compound comprises an oligonucleotide and a GLP-1 peptide conjugate moiety comprising an amino acid sequence with 1, 2, 3, 4, 5, 6, 7 or 8 amino acid substitutions, insertions, deletions, or a combination of two or more thereof, when compared to the amino acid sequence of GLP-1(7-37) (SEQ ID NO: 1). In certain embodiments, a compound comprises an oligonucleotide, conjugate linker, and a GLP-1 peptide conjugate moiety comprising an amino acid sequence with 1, 2, 3, 4, 5, 6, 7 or 8 amino acid substitutions, insertions, deletions, or a combination of two or more thereof, when compared to the amino acid sequence of GLP-1(7-37) (SEQ ID NO: 1).

In certain embodiments, a compound comprises an oligonucleotide, optionally a conjugate linker, and a GLP-1 peptide conjugate moiety comprising or consisting of an amino acid sequence of any of SEQ ID NOs: 1-57. In certain embodiments, a compound comprises an oligonucleotide and a GLP-1 peptide conjugate moiety comprising an amino acid sequence with 1, 2, 3, 4, 5, 6, 7 or 8 amino acid substitutions, insertions, deletions, or a combination of two or more thereof, when compared to the amino acid sequence of any of SEQ ID NOs: 1-57. In certain embodiments, a compound comprises an oligonucleotide, conjugate linker, and a GLP-1 peptide conjugate moiety comprising an amino acid sequence with 1, 2, 3, 4, 5, 6, 7 or 8 amino acid substitutions, insertions, deletions, or a combination of two or more thereof, when compared to the amino acid sequence of any of SEQ ID NOs: 1-57.

In any of the embodiments above, the GLP-1 peptide conjugate moiety may comprise a conservative amino acid substitution, an amino acid analog, or an amino acid derivative. In certain embodiments, the conservative amino acid substitution comprises replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof, and the aliphatic residue comprises Alanine, Valine, Leucine, Isoleucine or a synthetic equivalent thereof; the acidic residue comprises Aspartic acid, Glutamic acid or a synthetic equivalent thereof; the residue comprising an amide group comprises Aspartic acid, Glutamic acid or a synthetic equivalent thereof; the basic residue comprises Lysine, Arginine or a synthetic equivalent thereof; or, the aromatic residue comprises Phenylalanine, Tyrosine or a synthetic equivalent thereof.

Additional GLP-1 peptide conjugate moieties or analogs that may be used in embodiments provided herein are described in US 20140206607; U.S. Pat. No. 9,187,522; WO 2007/124461; WO 2014/096179; WO 2009/030738; WO 2016/055610; and U.S. Pat. No. 8,329,419, which are all incorporated by reference herein in their entireties.

Conjugate Linkers

In certain embodiments, a conjugate linker links a GLP-1 receptor ligand conjugate moiety to an oligonucleotide. In certain compounds, a GLP-1 receptor ligand conjugate moiety is attached to an oligonucleotide via a conjugate linker through a single bond. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, a compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

1. Certain Hexylamino Linkers

In certain embodiments, a compound comprises an oligonucleotide linked to a GLP-1 receptor ligand conjugate moiety by a conjugate linker selected from the following structures:

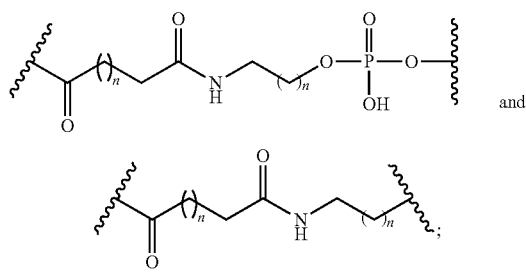

wherein each n is independently selected from 0, 1, 2, 3, 4, 5, 6, or 7.

In certain embodiments, a compound comprises an oligonucleotide linked to a GLP-1 receptor ligand conjugate moiety by a conjugate linker selected from the following structures:

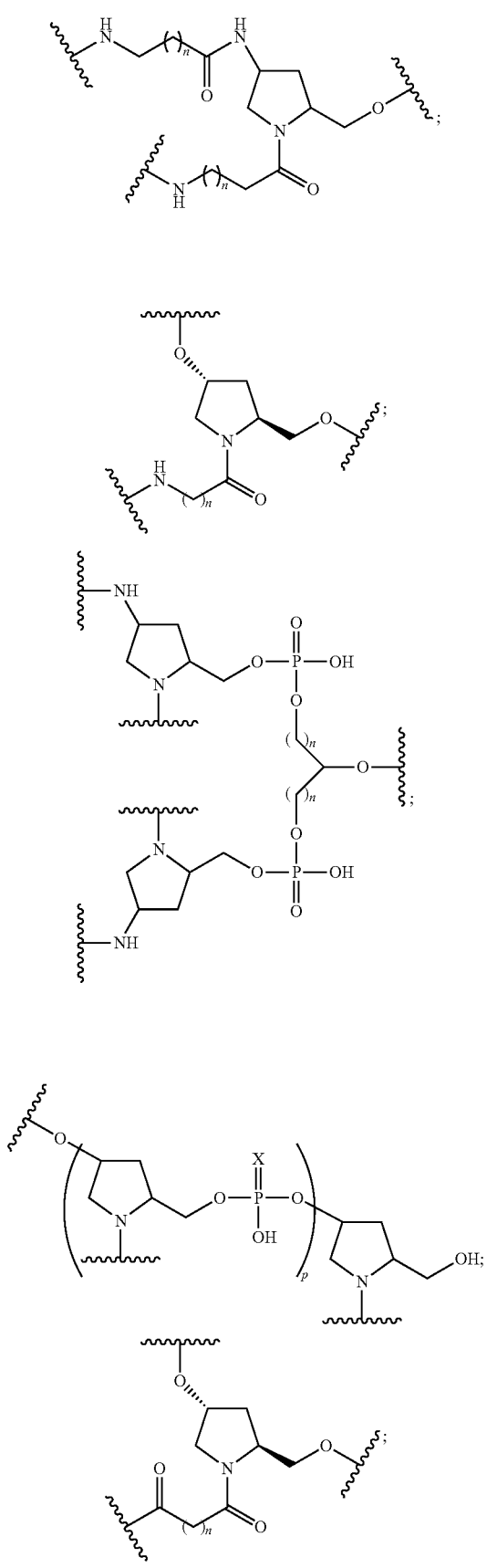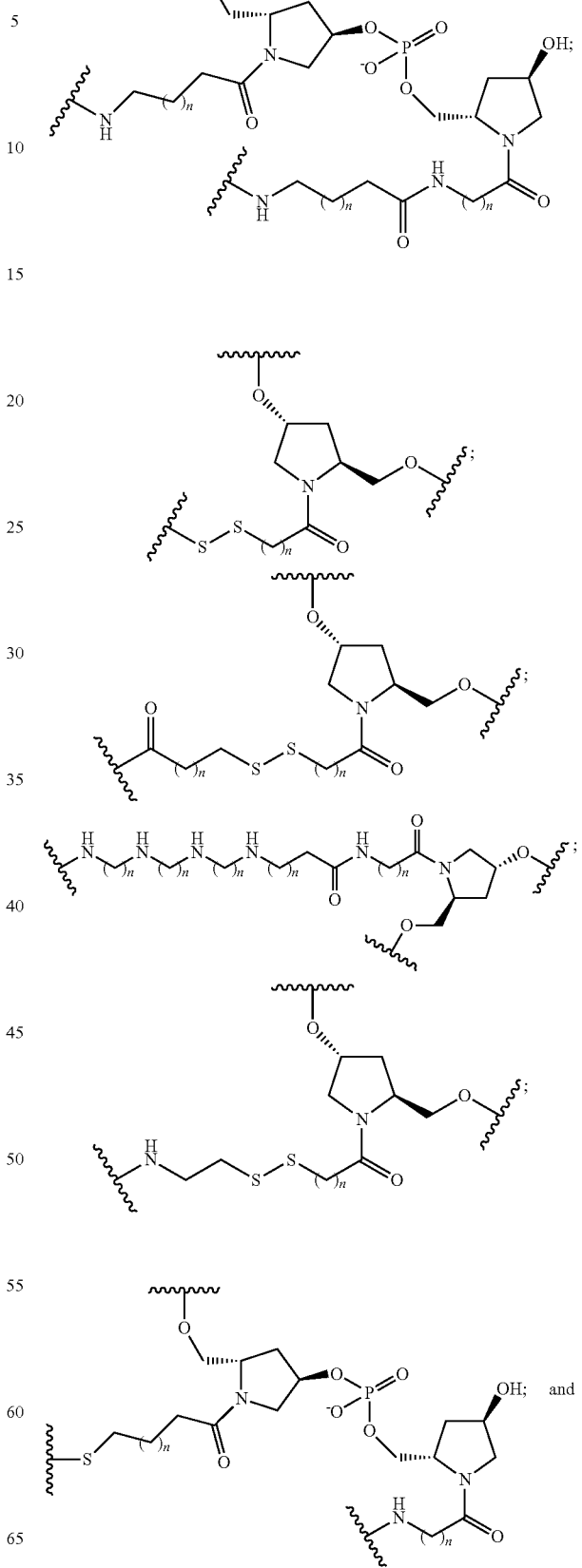

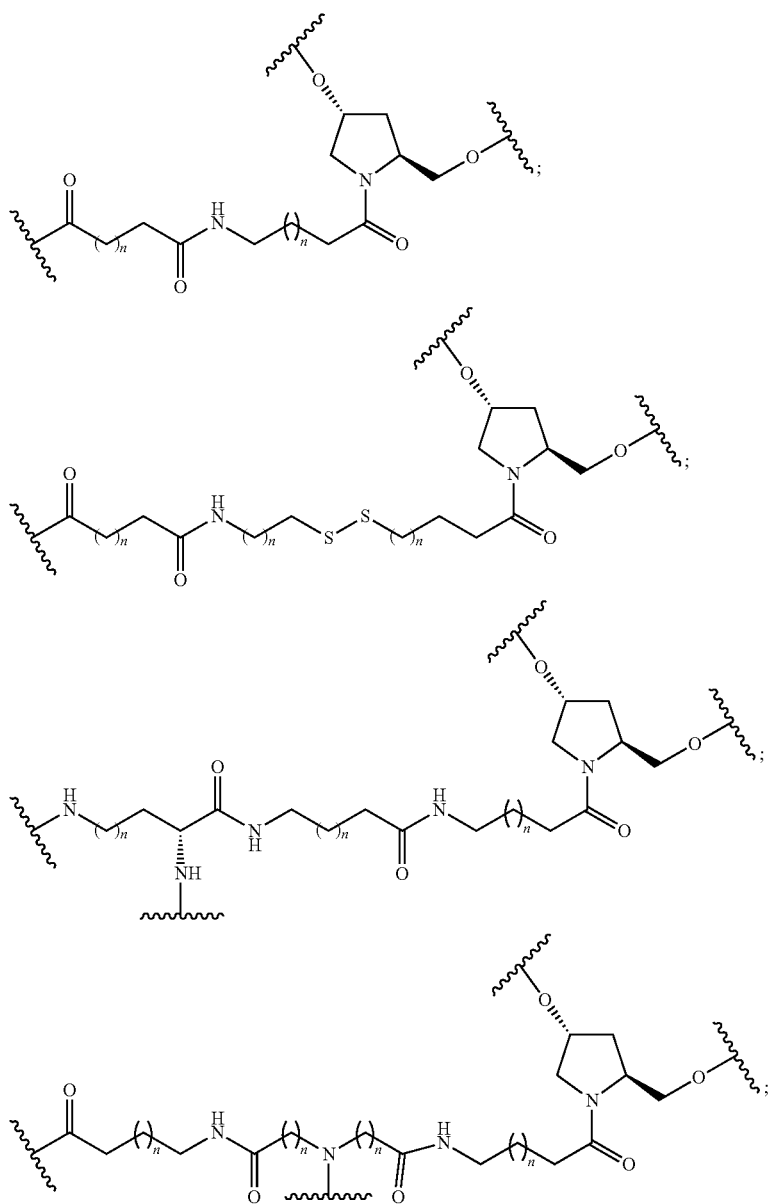
wherein each n is, independently from 1 to 20; and p is from 1 to 6.
In certain embodiments, a compound comprises an oligonucleotide linked to a GLP-1 receptor ligand conjugate moiety by a conjugate linker selected from the following structures:

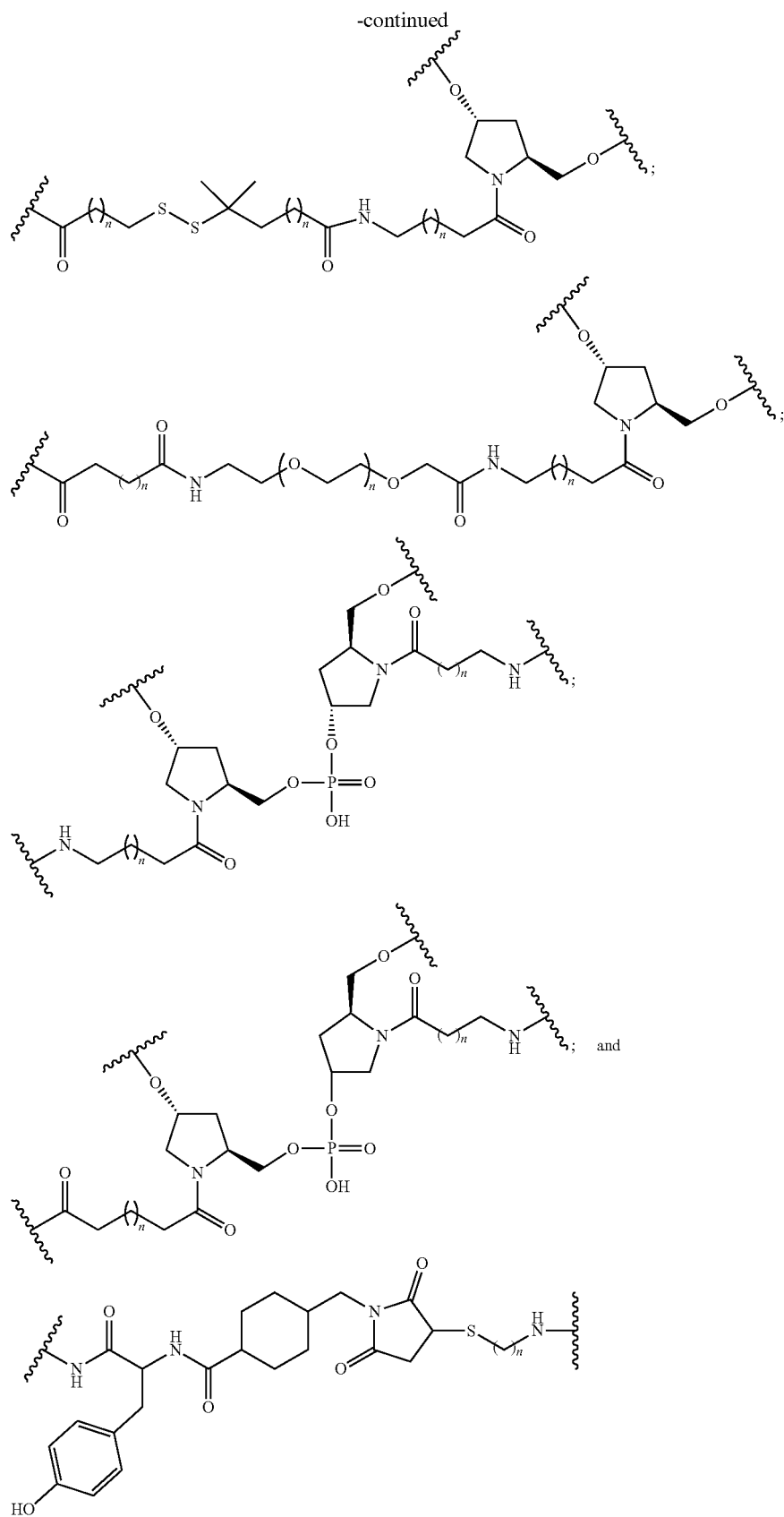
wherein each n is, independently, from 1 to 20.

In certain embodiments, a compound comprises an oligonucleotide linked to a GLP-1 receptor ligand conjugate moiety by a conjugate linker selected from the following structures:

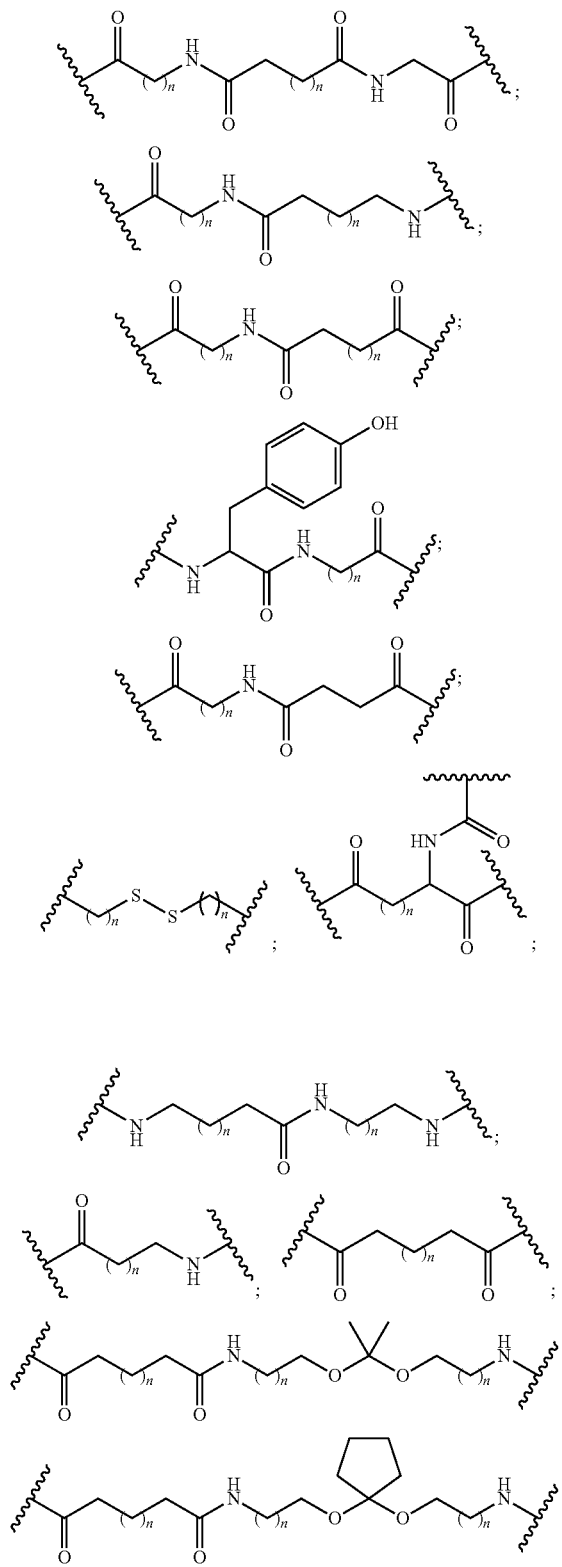

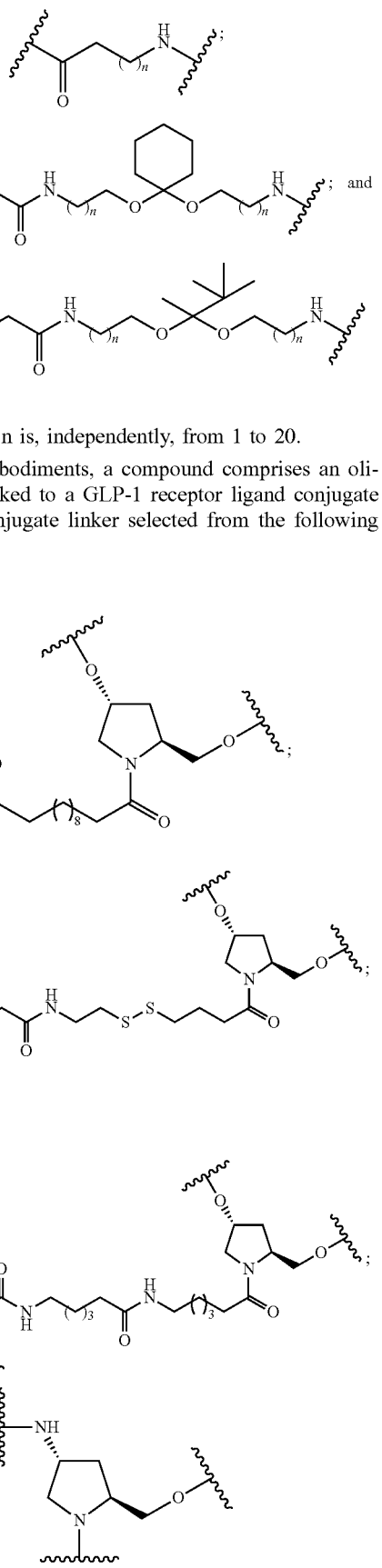

wherein each n is, independently, from 1 to 20.

In certain embodiments, a compound comprises an oligonucleotide linked to a GLP-1 receptor ligand conjugate moiety by a conjugate linker selected from the following structures:

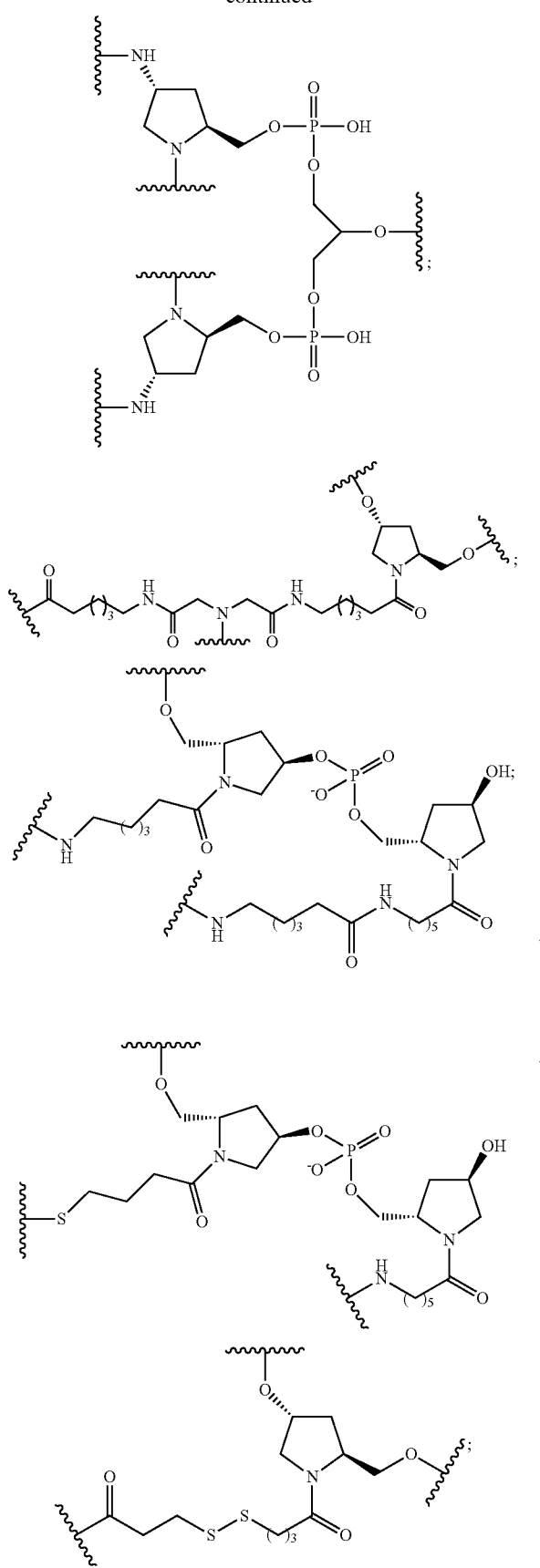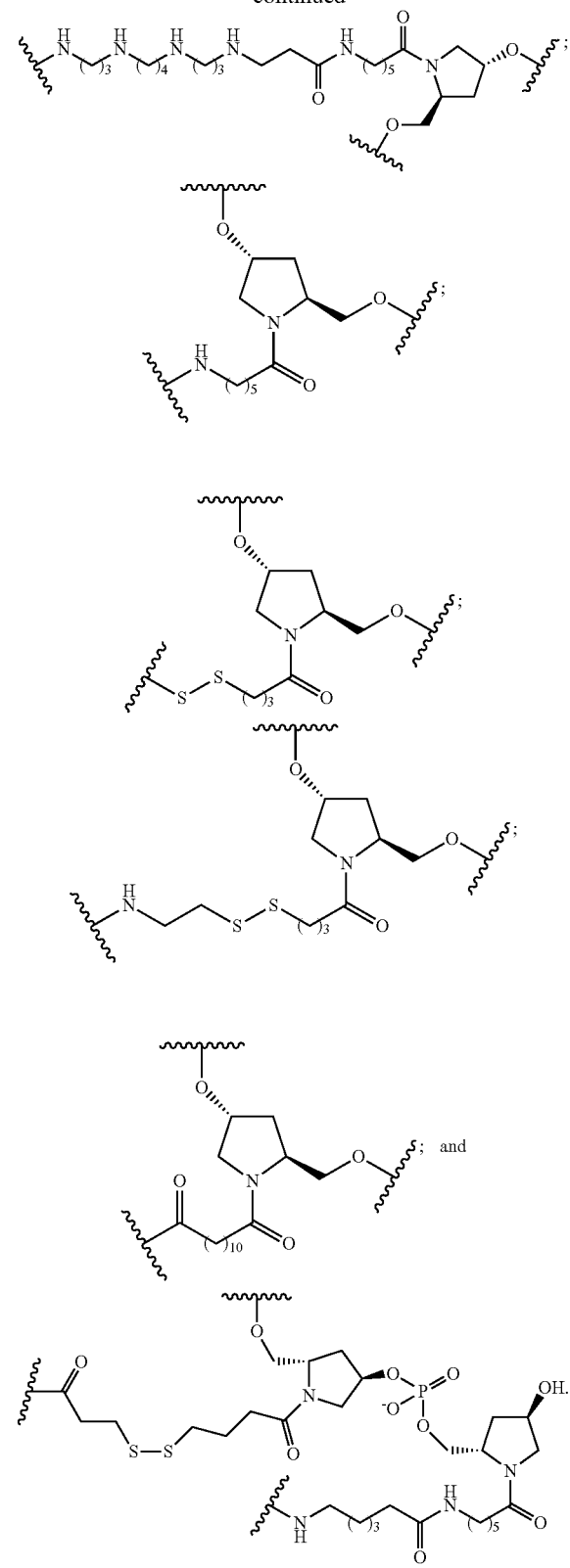
In certain embodiments, a compound comprises an oligonucleotide linked to a GLP-1 receptor ligand conjugate moiety by a conjugate linker selected from the following structures:

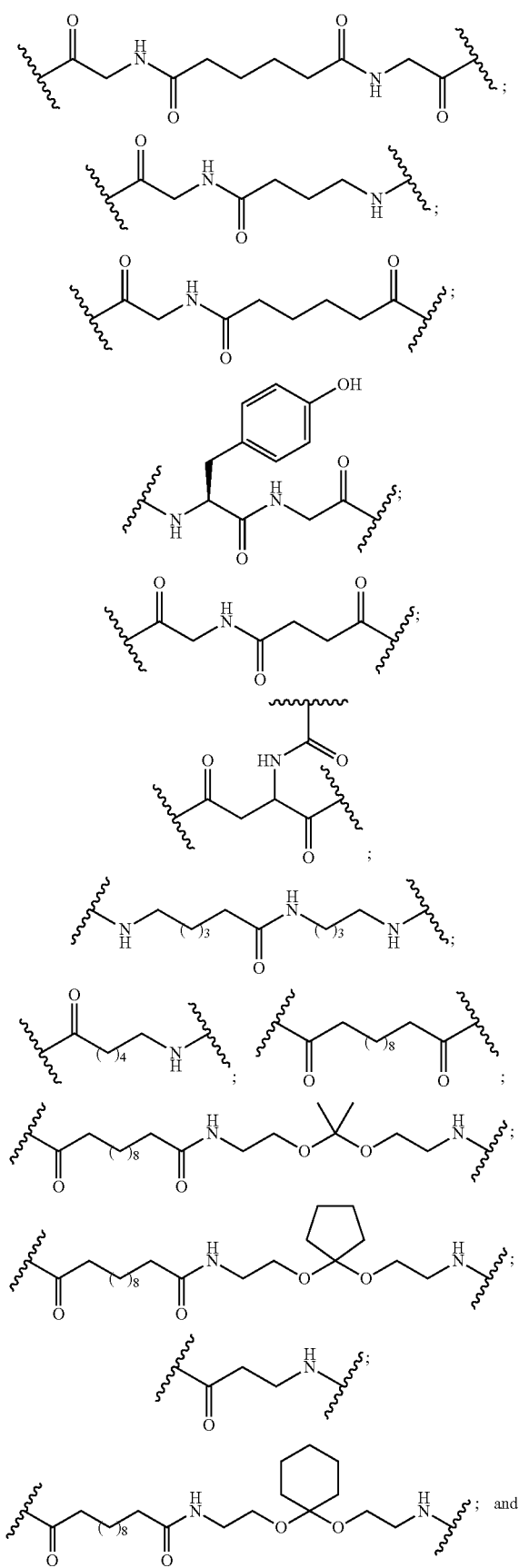

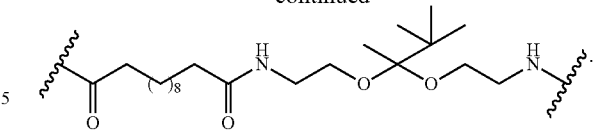

In certain embodiments, a compound comprises an oligonucleotide linked to a GLP-1 receptor ligand conjugate moiety by a conjugate linker selected from the following structures:

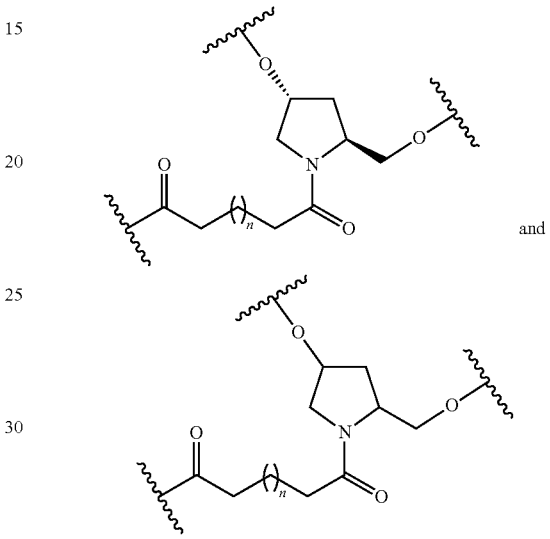

In certain embodiments, a compound comprises an oligonucleotide linked to a GLP-1 receptor ligand conjugate moiety by a conjugate linker having the following structure:

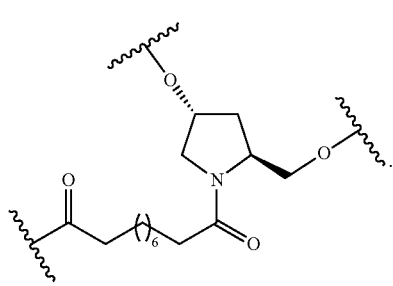

In certain embodiments, a compound comprises an oligonucleotide linked to a GLP-1 receptor ligand conjugate moiety by a conjugate linker having the following structure:

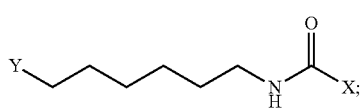

wherein
X directly or indirectly attaches to the GLP-1 receptor ligand conjugate moiety; and
Y directly or indirectly attaches to the modified oligonucleotide.

In certain embodiments, a compound comprises an oligonucleotide linked to a GLP-1 receptor ligand conjugate moiety by any conjugate linker described in WO 2014/179620, which is incorporated by reference herein in its entirety.

2. Certain Alkyl Phosphate Linkers

In certain embodiments, a compound comprises an oligonucleotide linked to a GLP-1 receptor ligand conjugate moiety by a conjugate linker having the following structure:

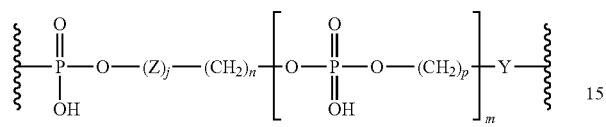

wherein:

the phosphate group is connected to the modified oligonucleotide and Y is connected to the conjugate group;

Y is a phosphodiester or amino (—NH—) group;

Z is a pyrrolidinyl group having the formula:

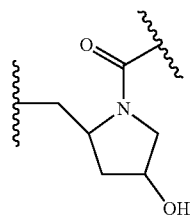 [SMILES: *CC1CC(O)CN1C(*)=O]

j is 0 or 1;

n is from about 1 to about 10;

p is from 1 to about 10;

m is 0 or from 1 to 4; and when Y is amino then m is 1.

In certain embodiments, Y is amino (—NH—). In certain embodiments, Y is a phosphodiester group. In certain embodiments, n is 3 and p is 3. In certain embodiments, n is 6 and p is 6. In certain embodiments, n is from 2 to 10 and p is from 2 to 10. In certain embodiments, n and p are different. In certain embodiments, n and p are the same. In certain embodiments, m is 0. In certain embodiments, m is 1. In certain embodiments, j is 0. In certain embodiments, j is 1 and Z has the formula:

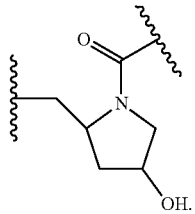 [SMILES: *CC1CC(O)CN1C(*)=O]

In certain embodiments, wherein n is 2 and p is 3. In certain embodiments, n is 5 and p is 6.

In certain embodiments, a compound comprises an oligonucleotide linked to a GLP-1 receptor ligand conjugate moiety by a conjugate linker having the following structure:

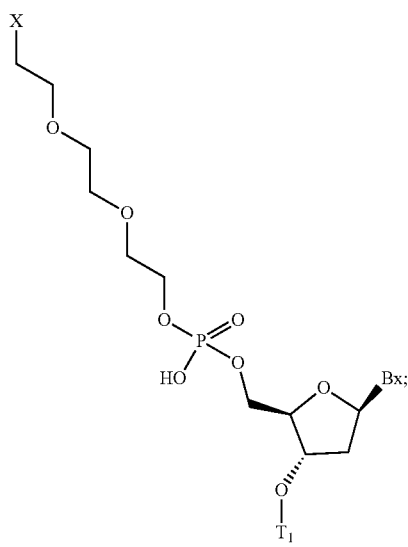

wherein X directly or indirectly attaches to the GLP-1 receptor ligand conjugate moiety; and wherein $T_1$ comprises the modified oligonucleotide; and Bx is a modified or unmodified nucleobase.

3. Certain Click Chemistry Linkers

In certain embodiments, a compound comprises an oligonucleotide linked to a GLP-1 receptor ligand conjugate moiety by a conjugate linker, wherein the conjugate linker is prepared using Click chemistry known in the art. Compounds have been prepared using Click chemistry wherein alkynyl phosphonate internucleoside linkages on an oligomeric compound attached to a solid support are converted into the 1,2,3-triazolylphosphonate internucleoside linkages and then cleaved from the solid support (Krishna et al., *J. Am. Chem. Soc.* 2012, 134(28), 11618-11631), which is incorporated by reference herein in its entirety. Additional linkers suitable for use in several embodiments can be prepared by Click chemistry described in "Click Chemistry for Biotechnology and Materials Science" Ed. Joerg Laham, Wiley 2009, which is incorporated by reference herein in its entirety.

In certain embodiments, a Click reaction can be used to link a GLP-1 receptor ligand conjugate moiety and an oligonucleotide by reacting:

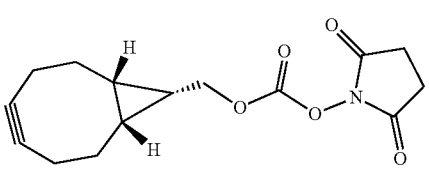 [SMILES: O=C(OC[C@@H]1[C@@H]2CCC#CCC[C@@H]21)ON1C(=O)CCC1=O]

with an oligonucleotide having a terminal amine, including but not limited to the following compound:

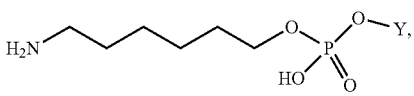

wherein Y is directly or indirectly attached to the oligonucleotide, to yield:

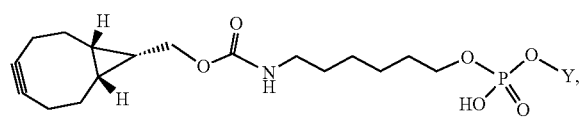

which can be reacted with a GLP-1 receptor ligand conjugate moiety having an azide to yield:

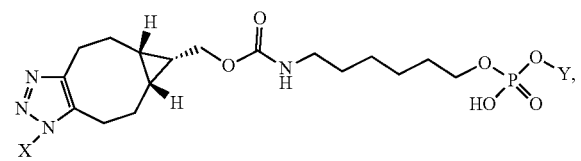

wherein N—N=N represents an azido group of the GLP-1 receptor ligand conjugate moiety and X is directly or indirectly attached to the remainder of the GLP-1 receptor ligand conjugate moiety.

In certain embodiments, a compound comprises an oligonucleotide linked to a GLP-1 receptor ligand conjugate moiety by a conjugate linker, wherein the conjugate linker is prepared from the following compound:

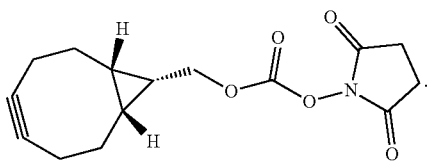 [SMILES: O=C(OC[C@@H]1[C@@H]2CCC#CCC[C@@H]21)ON1C(=O)CCC1=O]

In certain embodiments, a compound comprises an oligonucleotide linked to a GLP-1 receptor ligand conjugate moiety by a conjugate linker, wherein the conjugate linker comprises:

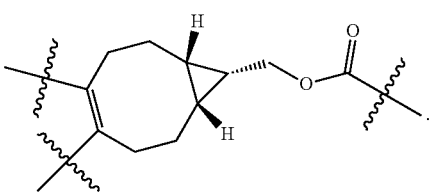 [SMILES: *C(=O)OC[C@@H]1[C@@H]2CC/C(*)=C(/*)CC[C@@H]21]

In certain embodiments, a compound comprises an oligonucleotide linked to a GLP-1 receptor ligand conjugate moiety by a conjugate linker, wherein the conjugate linker comprises:

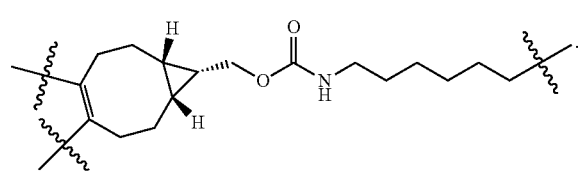 [SMILES: *CCCCCCNC(=O)OC[C@@H]1[C@@H]2CC/C(*)=C(/*)CC[C@@H]21]

In certain embodiments, a compound comprises an oligonucleotide linked to a GLP-1 receptor ligand conjugate moiety by a conjugate linker, wherein the compound comprises:

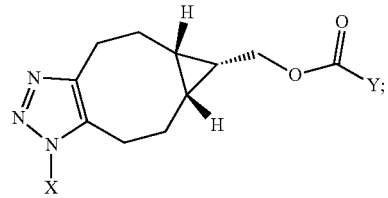

wherein N—N=N represents an azido group of the GLP-1 receptor ligand conjugate moiety and X directly or indirectly attaches to the remainder of the GLP-1 receptor ligand conjugate moiety; and Y directly or indirectly attaches to the oligonucleotide.

In certain embodiments, a compound comprises an oligonucleotide linked to a GLP-1 receptor ligand conjugate moiety by a conjugate linker, wherein the compound comprises:

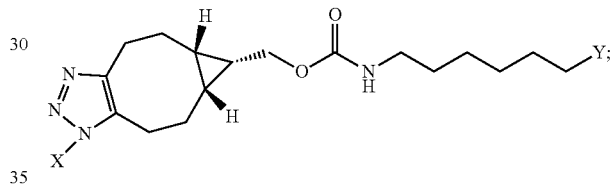

wherein N—N=N represents an azido group of the GLP-1 receptor ligand conjugate moiety and X directly or indirectly attaches to the remainder of the GLP-1 receptor ligand conjugate moiety; and Y directly or indirectly attaches to the oligonucleotide.

In certain embodiments, a compound comprises an oligonucleotide linked to a GLP-1 receptor ligand conjugate moiety by a conjugate linker, wherein the compound comprises:

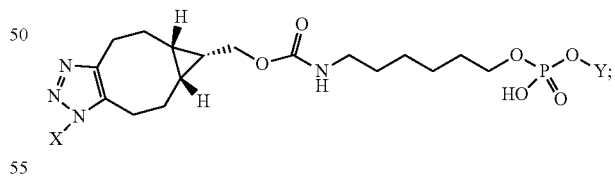

wherein N—N=N represents an azido group of the GLP-1 receptor ligand conjugate moiety and X directly or indirectly attaches to the remainder of the GLP-1 receptor ligand conjugate moiety; and Y directly or indirectly attaches to the oligonucleotide.

4. Certain Maleimide Linkers

In certain embodiments, a compound comprises an oligonucleotide linked to a GLP-1 receptor ligand conjugate moiety by a conjugate linker, wherein the conjugate linker comprises:

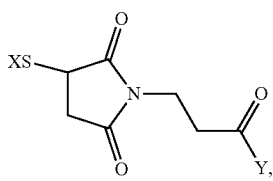

X directly or indirectly attaches to the GLP-1 receptor ligand conjugate moiety; and Y directly or indirectly attaches to the oligonucleotide.

In certain embodiments, the above conjugate linker can link a peptide to an oligonucleotide. In certain embodiments, a compound comprises an oligonucleotide linked to a peptide by a conjugate linker, wherein the conjugate linker comprises:

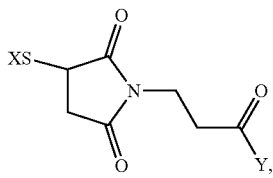

X directly or indirectly attaches to the peptide; and
Y directly or indirectly attaches to the oligonucleotide.

5. Certain Disulfide Linkages

In certain embodiments, a compound comprises an oligonucleotide linked to a GLP-1 receptor ligand conjugate moiety by a conjugate linker, wherein the conjugate linker comprises a disulfide linkage. In certain embodiments, oligonucleotides comprise activated disulfides which form a disulfide linkage with a GLP-1 peptide conjugate moiety. In certain embodiments, a compound comprises an oligonucleotide comprising an activated disulfide moiety capable of forming a cleavable or reversible bond with a GLP-1 peptide conjugate moiety. In certain embodiments, a compound comprises an oligonucleotide directly attached to a GLP-1 peptide conjugate moiety by a disulfide bond without a conjugate linker.

In certain embodiments, a compound comprises a linker between an oligonucleotide and activated disulfide moiety. In another embodiment, the activated disulfide moiety has the formula —S—S(O)2-substituted or unsubstituted C1-C12 alkyl or —S—S—C(O)O-substituted or unsubstituted $C_1$-$C_{12}$ alkyl. Preferred activated disulfide moieties are methane thiosulfonate and dithiocarbomethoxy. In further embodiments, the activated disulfide is substituted or unsubstituted dithiopyridyl, substituted or unsubstituted dithiobenzothiazolyl, or substituted or unsubstituted dithiotetrazolyl. Preferred activated disulfides are 2-dithiopyridyl, 2-dithio-3-nitropyridyl, 2-dithio-5-nitropyridyl, 2-dithiobenzothiazolyl, N—($C_1$-$C_{12}$ alkyl)-2-dithiopyridyl, 2-dithiopyridyl-N-oxide, or 2-dithio-1-methyl-1H-tetrazolyl.

In some embodiments, the activated disulfide moiety has the formula —S—S(O)$_n$—R$_1$, wherein
  n is 0, 1, or 2; and
  R$_1$ is selected from substituted or unsubstituted heterocyclic, substituted or unsubstituted aliphatic, or —C(O)O—R$_2$, wherein R$_2$ is substituted or unsubstituted aliphatic.

In another embodiment, the activated disulfide moiety has the formula —S—S(O)$_2$-substituted or unsubstituted $C_1$-$C_{12}$ alkyl or —S—S—C(O)O-substituted or unsubstituted $C_1$-$C_{12}$ alkyl. In certain embodiments, activated disulfide moieties include methane thiosulfonate and dithiocarbomethoxy. In further embodiments, the activated disulfide can be substituted or unsubstituted dithiopyridyl, substituted or unsubstituted dithiobenzothiazolyl, or substituted or unsubstituted dithiotetrazolyl. Further examples of activated disulfides include but are not limited to 2-dithiopyridyl, 2-dithio-3-nitropyridyl, 2-dithio-5-nitropyridyl, 2-dithiobenzothiazolyl, N—($C_1$-$C_{12}$ alkyl)-2-dithiopyridyl, 2-dithiopyridyl-N-oxide, and 2-dithio-1-methyl-1H-tetrazolyl.

In some embodiments, the bivalent linking group is a bivalent substituted or unsubstituted aliphatic group. In another embodiment, the bivalent linking group has the formula -Q$_1$-G-Q$_2$-, wherein
  Q$_1$ and Q$_2$ are independently absent or selected from substituted or unsubstituted $C_1$-$C_{12}$ alkylene, substituted or unsubstituted alkarylene or —(CH$_2$)$_m$—O—(CH$_2$)$_p$—, wherein
  each m and p are, independently, an integer from 1 to about 10;
  G is —NH—C(O)—, —C(O)—NH—, —NH—C(O)—NH—, —NH—C(S)—NH—, —NH—O—, NH—C(O)—O—, or —O—CH$_2$—C(O)—NH—.

Examples of bivalent linking groups include but are not limited to:

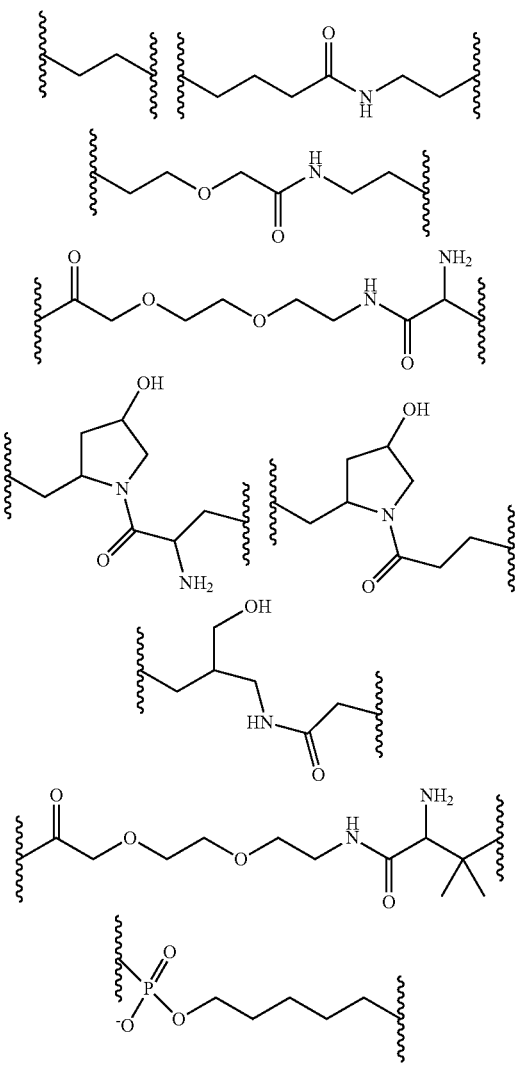

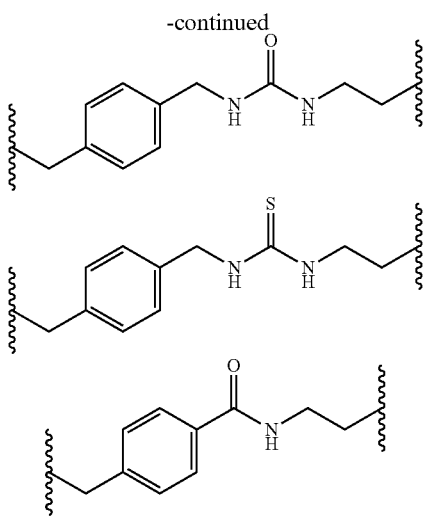

In certain embodiments, a compound comprises an oligonucleotide linked to a GLP-1 peptide conjugate moiety by a disulfide linkage described in U.S. Pat. No. 7,713,944, which is incorporated by reference herein in its entirety. In certain embodiments, a compound comprises an oligonucleotide linked to a GLP-1 peptide conjugate moiety wherein the oligonucleotide comprises an activated disulfide described in U.S. Pat. No. 7,713,944, which is incorporated by reference herein in its entirety.

In certain embodiments, any of the above compounds comprising an oligonucleotide linked to a GLP-1 peptide conjugate moiety by a disulfide linkage, whether directly or by a conjugate linker described herein, can comprise a disulfide linkage between a cysteine, penicillamine, homocysteine, mercaptopropionic acid, or β-Mercapto-β,β,-cyclopentamethylene propionic acid moiety of the GLP-1 peptide conjugate moiety and the oligonucleotide or conjugate linker. In certain embodiments, a compound comprises an oligonucleotide directly linked to a GLP-1 peptide conjugate moiety by a disulfide linkage. In certain embodiments a compound comprises an oligonucleotide directly linked to a GLP-1 peptide conjugate moiety by a disulfide linkage, wherein the disulfide linkage is between the oligonucleotide and a a cysteine, penicillamine, homocysteine, mercaptopropionic acid, or β-Mercapto-β,β,-cyclopentamethylene propionic acid moiety of the GLP-1 peptide conjugate moiety. In certain embodiments, a compound comprises an oligonucleotide, conjugate linker, and GLP-1 peptide conjugate moiety wherein a disulfide linkage links the conjugate linker and the GLP-1 peptide conjugate moiety, and the oligonucleotide is attached to the conjugate linker. In certain embodiments, a compound comprises an oligonucleotide, conjugate linker, and GLP-1 peptide conjugate moiety wherein a disulfide linkage links the conjugate linker to a cysteine, penicillamine, homocysteine, mercaptopropionic acid, or β-Mercapto-β,β,-cyclopentamethylene propionic acid moiety of the GLP-1 peptide conjugate moiety, and the oligonucleotide is attached to the conjugate linker. In certain embodiments, the cysteine, penicillamine, homocysteine, mercaptopropionic acid, or β-Mercapto-β,β,-cyclopentamethylene propionic acid moiety is at the N-terminus, C-terminus, side chain, or internal amino acid position of the GLP-1 peptide conjugate moiety.

6. Certain Enzyme Cleavable Linkages

In certain embodiments, a compound comprises an oligonucleotide linked to a GLP-1 receptor ligand conjugate moiety by a conjugate linker, wherein the conjugate linker comprises an enzyme cleavable moiety. In certain embodiments, the GLP-1 receptor ligand conjugate moiety is a GLP-1 peptide conjugate moiety. In certain embodiments, the enzyme cleavable moiety is a peptide, such as a dipeptide.

Enzymes known in the art for use in activating prodrugs can be used to cleave an enzyme cleavable moiety provided in certain embodiments. In certain embodiments, an enzyme cleavable moiety can be cleaved by DT diaphorase, plasmin, carboxypeptidase G2, thymidine kinase (viral), cytosine deaminase, glucose oxidase, xanthine oxidase, carboxypeptidase A, α-galactosidase, β-glucosidase, azoreductase, γ-glutamyltransferase, β-glucuronidase, β-lactamase, alkaline phosphatase, aminopeptidase, penicillin amidase or nitroreductase.

In certain embodiments, the enzyme cleavable moiety is cleavable by a protease or peptidase. In certain embodiments, the enzyme cleavable moiety is cleavable by a protease or peptidase selected from: gastricsin, memapsin-2, chymosin, renin, renin-2, cathepsin D, cathepsin E, penicillopepsin, rhizopuspepsin, mucorpepsin, barrierpepsin, aspergillopepsin I, endothiapepsin, saccharopepsin, phytepsin, plasmepsin-1, plasmepsin-2, yapsin-1, yapsin-2, nepenthesin, memapsin-1, napsin A, HIV-1 retropepsin, HIV-2 retropepsin, simian immunodeficiency virus retropepsin, equine infectious anaemia virus retropepsin, feline immunodeficiency virus retropepsin, murine leukemia virus-type retropepsin, Mason-Pfizer leukemia virus retropepsin, human endogenous retrovirus K retropepsin, retropepsin (human T-cell leukemia virus), bovine leukemia virus retropepsin, Rous sarcoma virus retropepsin, scytalidoglutamic peptidase, aspergilloglutamic peptidase, thermopsin, signal peptidase II, spumapepsin, type 4 prepilin peptidase 1, omptin, plasminogen activator Pla, papain, chymopapain, caricain, glycyl endopeptidase, stem bromelain, ficain, actinidain, cathepsin V, vignain, cathepsin X, zingipain, cathepsin F, ananain, fruit bromelain, cathepsin L, cathepsin L1 (*Fasciola* sp.), cathepsin S, cathepsin K, cathepsin H, aleurain, histolysain, cathepsin B, dipeptidyl-peptidase I, peptidase 1 (mite), CPB peptidase, cruzipain, V-cath peptidase, bleomycin hydrolase (animal), bleomycin hydrolase (yeast), aminopeptidase C, CPC peptidase, calpain-1, calpain-2, calpain-3, Tpr peptidase (*Porphyromonas gingivalis*), poliovirus-type picornain 3C, hepatitis A virus-type picornain 3C, human rhinovirus 2-type picornain 3C, foot-and-mouth disease virus picornain 3C, enterovirus picornain 2A, rhinovirus picornain 2A, nuclear-inclusion-a peptidase (plum pox virus), tobacco etch virus NIa peptidase, adenain, potato virus Y-type helper component peptidase, sindbis virus-type nsP2 peptidase, streptopain, clostripain, ubiquitinyl hydrolase-L1, ubiquitinyl hydrolase-L3, legumain (plant beta form), legumain, animal-type, caspase-1, caspase-3, caspase-7, caspase-6, caspase-8, caspase-9, pyroglutamyl-peptidase I (prokaryote), pyroglutamyl-peptidase I (chordate), murine hepatitis coronavirus papain-like peptidase 1, ubiquitin-specific peptidase 5, tymovirus peptidase, rabbit hemorrhagic disease virus 3C-like peptidase, gingipain RgpA, gingipain Kgp, gamma-glutamyl hydrolase, foot-and-mouth disease virus L-peptidase, porcine transmissible gastroenteritis virus-type main peptidase, calicivirin, staphopain A, Ulp1 peptidase, separase (yeast-type), YopJ protein, Pfpl peptidase, sortase A (*Staphylococcus*-type), aminopeptidase N, lysyl aminopeptidase (bacteria), aminopeptidase A, leukotriene A4 hydrolase, pyroglutamyl-peptidase II, cytosol alanyl aminopeptidase, cystinyl aminopeptidase, aminopeptidase B, aminopeptidase Ey, angiotensin-converting enzyme peptidase unit 1, peptidyl-dipeptidase Acer, angiotensin-converting enzyme peptidase unit 2, angiotensin-converting enzyme-2, thimet oligopeptidase, neurolysin, saccharolysin, oligopeptidase A, peptidyl-dipeptidase Dcp, mitochondrial intermediate peptidase, oligopeptidase F, thermolysin, vibriolysin, pseudolysin, coccolysin, aureolysin, stearolysin, mycolysin, snapalysin, leishmanolysin, bacterial collagenase V, bacterial collagenase G/A, matrix metallopeptidase-1, matrix metallopeptidase-8, matrix metallopeptidase-2, matrix metallopeptidase-9, matrix metallopeptidase-3, matrix metallopeptidase-10 (*Homo sapiens*-type), matrix metallopeptidase-11, matrix metallopeptidase-7, matrix metallopeptidase-12, envelysin, matrix metallopeptidase-13, membrane-type matrix metallopeptidase-1, membrane-type matrix metallopeptidase-2, matrix metallopeptidase-20, fragilysin, matrix metallopeptidase-26, serralysin, aeruginolysin, gametolysin, astacin, meprin alpha subunit, procollagen C-peptidase, choriolysin L, choriolysin H, flavastacin, fibrolase, jararhagin, adamalysin, atrolysin A, atrolysin B, atrolysin C, atrolysin E, atroxase, russellysin, ADAM1 peptidase, ADAM9 peptidase, ADAM10 peptidase, Kuzbanian peptidase (non-mammalian), ADAM12 peptidase, ADAM17 peptidase, ADAMTS4 peptidase, ADAMTS1 peptidase, ADAMTS5 peptidase, ADAMTS13 peptidase, procollagen I N-peptidase, neprilysin, endothelin-converting enzyme 1, oligopeptidase O1, neprilysin-2, PHEX peptidase, carboxypeptidase A1, carboxypeptidase A2, carboxypeptidase B, carboxypeptidase N, carboxypeptidase E, carboxypeptidase M, carboxypeptidase T, carboxypeptidase B2, carboxypeptidase A3, metallocarboxypeptidase D peptidase unit 1, metallocarboxypeptidase D peptidase unit 2, zinc D-Ala-D-Ala carboxypeptidase (*Streptomyces*-type), vanY D-Ala-D-Ala carboxypeptidase, vanX D-Ala-D-Ala dipeptidase, pitrilysin, insulysin, mitochondrial processing peptidase beta-subunit, nardilysin, leucine aminopeptidase 3, leucyl aminopeptidase (plant-type), aminopeptidase I, aspartyl aminopeptidase, membrane dipeptidase, glutamate carboxypeptidase, peptidase T, carboxypeptidase Ss1, beta-lytic metallopeptidase, staphylolysin, lysostaphin, methionyl aminopeptidase 1 (*Escherichia*-type), methionyl aminopeptidase 2, Xaa-Pro dipeptidase (bacteria-type), aminopeptidase P (bacteria), aminopeptidase P2, Xaa-Pro dipeptidase (eukaryote), TgA1-specific metallopeptidase, tentoxilysin, bontoxilysin, aminopeptidase Y, aminopeptidase Ap1, aminopeptidase S (*Streptomyces*-type), glutamate carboxypeptidase II, carboxypeptidase Taq, anthrax lethal factor, deuterolysin, peptidyl-Lys metallopeptidase, FtsH peptidase, m-AAA peptidase, i-AAA peptidase, AtFtsH2 peptidase, pappalysin-1, Ste24 peptidase, dipeptidyl-peptidase III, site 2 peptidase, sporulation factor SpoIVFB, HybD peptidase, gpr peptidase, chymotrypsin A (cattle-type), granzyme B (*Homo sapiens*-type), factor VII-activating peptidase, trypsin (*Streptomyces griseus*-type), hypodermin C, elastase-2, cathepsin G, myeloblastin, granzyme A, granzyme M, chymase (*Homo sapiens*-type), mast cell peptidase 1 (*Rattus*-type), duodenase, tryptase alpha, granzyme K, mast cell peptidase 5 (mouse numbering), trypsin 1, chymotrypsin B, elastase-1, pancreatic endopeptidase E, pancreatic elastase II, enteropeptidase, chymotrypsin C, prostasin, kallikrein 1, kallikrein-related peptidase 2, kallikrein-related peptidase 3, kallikrein 1 (*Mus musculus*), kallikrein 1-related peptidase b3, kallikrein 1-related peptidase c2 (*Rattus norvegicus*), kallikrein 13 (*Mus musculus*), ancrod, bothrombin, complement factor D, complement component activated C1r, complement component activated C1s, complement factor Bb, mannan-binding lectin-associated serine peptidase 1, complement factor I, coagulation factor XIIa, plasma kallikrein, coagulation factor XIa, coagulation factor IXa, coagulation factor VIIa, coagulation factor Xa, thrombin, protein C (activated), coagulation factor C (*Limulus, Tachypleus*), activated, coagulation factor B (*Limulus, Tachypleus*), activated, clotting enzyme (*Tachypleus*-type), acrosin, hepsin, mannan-binding lectin-associated serine peptidase 2, urokinase-type plasminogen activator, t-plasminogen activator, plasmin, kallikrein-related peptidase 6, plasminogen activator (*Desmodus*-type), kallikrein-related peptidase 8, kallikrein-related peptidase 4, streptogrisin A, streptogrisin B, streptogrisin E, alpha-lytic endopeptidase, glutamyl peptidase I, DegP peptidase, HtrA2 peptidase, lysyl endopeptidase (bacteria), kallikrein-related peptidase 7, matriptase, togavirin, IgA1-specific serine peptidase (*Neisseria*-type), flavivirin, subtilisin Carlsberg, subtilisin lentus, thermitase, subtilisin Ak1, lactocepin I, C5a peptidase, dentilisin, subtilisin BPN', subtilisin E, aqualysin 1, cerevisin, oryzin, endopeptidase K, thermomycolin, site-1 peptidase, kexin, furin, PCSK1 peptidase, PCSK2 peptidase, PCSK4 peptidase, PCSK6 peptidase, PCSK5 peptidase, PCSK7 peptidase, tripeptidyl-peptidase II, cucumisin, prolyl oligopeptidase, dipeptidyl-peptidase IV (eukaryote), acylaminoacyl-peptidase, fibroblast activation protein alpha subunit, oligopeptidase B, carboxypeptidase Y, serine carboxypeptidase A, serine carboxypeptidase C, serine carboxypeptidase D, kex carboxypeptidase, D-Ala-D-Ala carboxypeptidase A, K15-type DD-transpeptidase, D-Ala-D-Ala carboxypeptidase B, aminopeptidase DmpB, D-Ala-D-Ala peptidase C, peptidase Clp (type 1), Xaa-Pro dipeptidyl-peptidase, Lon-A peptidase, PIM1 peptidase, assemblin, cytomegalovirus assemblin, herpesvirus 8-type assemblin, repressor LexA, UmuD protein, signal peptidase 1, mitochondrial inner membrane peptidase 1, signal peptidase SipS, signalase (animal) 21 kDa component, lysosomal Pro-Xaa carboxypeptidase, dipeptidyl-peptidase II, hepacivirin, potyvirus P1 peptidase, pestivirus NS3 polyprotein peptidase, equine arteritis virus serine peptidase, prolyl aminopeptidase, C-terminal processing peptidase-1, C-terminal processing peptidase-2, tricorn core peptidase (archaea), signal peptide peptidase A, infectious pancreatic necrosis birnavirus Vp4 peptidase, dipeptidase E, sedolisin, sedolisin-B, tripeptidyl-peptidase I, kumamolisin, physarolisin, SpoIVB peptidase, archaean proteasome, beta component, bacterial proteasome, beta component, HslV component of HslUV peptidase, constitutive proteasome catalytic subunit 1, constitutive proteasome catalytic subunit 2, constitutive proteasome catalytic subunit 3, gamma-glutamyl-transferase 1 (bacterial-type), murein tetrapeptidase LD-carboxypeptidase (*Escherichia*-type), PepA aminopeptidase, presenilin 1, polyporopepsin, canditropsin, candidapepsin SAP2, caspase-2, caspase DRONC (*Drosophila melanogaster*)-type peptidase, ubiquitin-specific peptidase 7, human coronavirus 229E main peptidase, SARS coronavirus picornain 3C-like peptidase, AvrPphB peptidase, sortase B, psychrophilic alkaline metallopeptidase (*Pseudomonas* sp.), acutolysin A, aminopeptidase S (*Staphylococcus*-type), carboxypeptidase Pfu, isoaspartyl dipeptidase (metallo-type), D-aminopeptidase DppA, and murein endopeptidase. In certain embodiments, the enzyme cleavable moiety is cleavable by a cathepsin protease or peptidase.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. In certain embodiments, a pharmaceutical composition comprises a compound described herein and a pharmaceutically acceptable diluent or carrier. In certain embodiments, a pharmaceutical composition comprises a sterile saline solution and one or more compound described herein. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound described herein and sterile water. In certain embodiments, a pharmaceutical composition consists of one compound described herein and sterile water. In certain embodiments, the sterile water is pharmaceutical grade water. In certain embodiments, a pharmaceutical composition comprises one or more compound described herein and phosphate-buffered saline (PBS). In certain embodiments, a pharmaceutical composition consists of one or more compound described herein and sterile PBS. In certain embodiments, the sterile PBS is pharmaceutical grade PBS.

Pharmaceutical compositions comprising compounds described herein encompass any pharmaceutically acceptable salts, esters, or salts of such esters, or any other oligonucleotide which, upon administration to an animal, including a human, is capable of providing (directly or indirectly) the biologically active metabolite or residue thereof. Certain embodiments are drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

Non-Limiting Disclosure and Incorporation by Reference

While certain compounds, compositions and methods described herein have been described with specificity in accordance with certain embodiments, the following examples serve only to illustrate the compounds described herein and are not intended to limit the same.

Each reference recited herein, including but not limited to scientific literature, patent publications, GenBank accession numbers, and the like is incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "ATmCGAUCG," wherein mC indicates a cytosine base comprising a methyl group at the 5-position.

Compounds described herein include (R) or (S), as α or β such as for sugar anomers, or as (D) or (L) such as for amino acids etc. Included in the compounds provided herein are all such possible isomers, including their racemic and optically pure forms, unless specified otherwise. Likewise, all cis- and trans-isomers and tautomeric forms are also included. Compounds described herein include chirally pure or enriched mixtures as well as racemic mixtures. For example, oligonucleotides having a plurality of phosphorothioate internucleoside linkages include such compounds in which chirality of the phosphorothioate internucleoside linkages is controlled or is random.

Unless otherwise indicated, any compound, including oligomeric compounds, described herein includes a pharmaceutically acceptable salt thereof.

Compounds described herein include variations in which one or more atoms are replaced with a non-radioactive isotope or radioactive isotope of the indicated element. For example, compounds herein that comprise hydrogen atoms encompass all possible deuterium substitutions for each of the $^1H$ hydrogen atoms. Isotopic substitutions encompassed by the compounds herein include but are not limited to: $^2H$ or $^3H$ in place of $^1H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$.

EXAMPLES

Example 1: Preparation of Antisense Oligonucleotide (ASO) Targeted to MALAT1 Conjugated with GLP-1 Peptide Method for the preparation of conjugated modified oligonucleotides comprising GLP-1 at the 5' position conjugated via a 3-mercaptopropionate linker.

Unless otherwise stated, all reagents and solutions used for the synthesis of oligomeric compounds are purchased from commercial sources. Standard phosphoramidite building blocks and solid support are used for incorporation of nucleoside residues which include for example T, A, G, and mC residues. A 0.1 M solution of phosphoramidite in anhydrous acetonitrile was used for 2'-deoxyribonucleoside, cEt BNA nucleosides, and suitably protected 6-amino-hexanol.

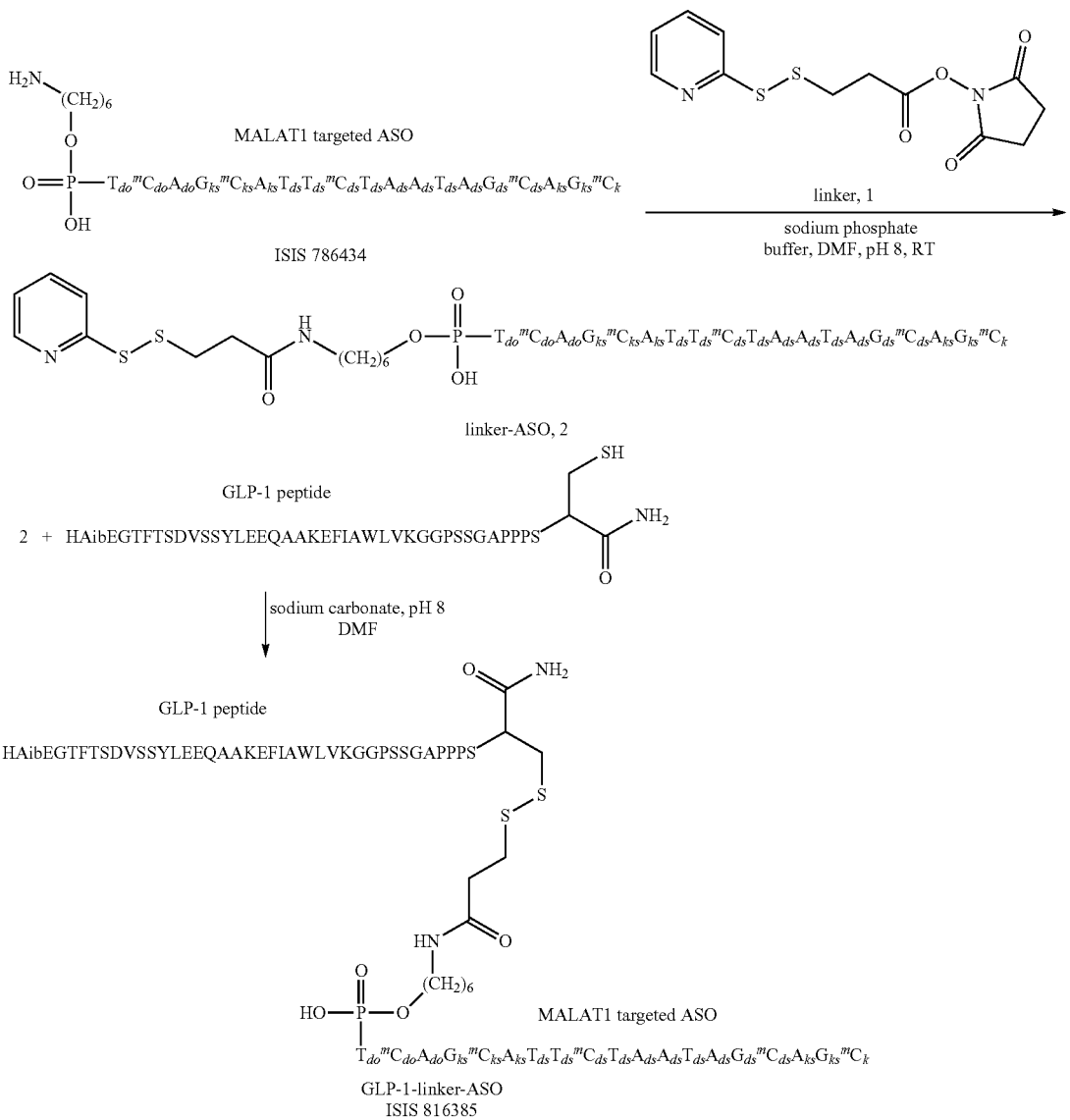

A 5'-hexylamino modified oligonucleotide (ISIS 786434) (nucleobase sequence: TCAGCATTCTAATAGCAGC (SEQ ID NO: 38) was synthesized and purified using standard solid-phase oligonucleotide procedures. The 5' end of the modified oligonucleotide comprises a hexamethylene linker and a terminal amine. Compound 1 (3-(2-Pyridyldithio propionic acid N-hydroxysuccinimide ester) was obtained from Chem-Impex (cat #11566). Modified oligonucleotide (~6 μmol) was dissolved in 125 μL sodium phosphate buffer, pH 8 and 12 μmol of compound 1 was dissolved in DMF. The solution of compound 1 was added dropwise to the modified oligonucleotide solution and allowed to react at room temperature. Reaction was complete after 2-3 hours and the product 2 was purified by HPLC on source 30Q resin with buffer A 100 mM NH4OAc/30% ACN/H2O and buffer B 100 mM NH4OAc/30% ACN/H2O+1.5M NaBr, and desalted by HPLC on a reverse phase column. Product fractions were concentrated and stored at −20° C.

Compound 2 was used as the starting material for reaction with the GLP-1 peptide HisAibGluGlyThrPheThrSerAspValSerSerTyrLeuGluGluGlnAlaAlaLysGluPheIleAlaTrpLeuValLysGlyG lyProSerSerAlaProProProSerCys-NH$_2$ (SEQ ID NO: 22), which was synthesized via standard solid phase peptide synthesis. Aib is 2-aminoisobutyric acid. Compound 2 was dissolved in degassed water and 0.1M NaHCO$_3$ was added to adjust the pH to ~8.0. GLP-1 peptide was dissolved in 50/50 0.1 M NaHCO$_3$ (pH 8):DMF (dimethylformamide). Peptide solution was added to compound 2 in small portions (30% of total volume each time) in 5 min intervals. After ~1 hr, the reaction mixture was diluted with water (5 fold of reaction solution volume V/V) and products were purified by HPLC on source 30Q resin with buffer A 100 mM NH$_4$OAc/30% ACN/H$_2$O and buffer B 100 mM NH$_4$OAc/30% ACN/H$_2$O+1.5M NaBr. Product fractions were desalted by HPLC on a reverse phase column to yield ISIS 816385.

Example 2: Preparation of Antisense Oligonucleotide (ASO) Targeted to MALAT1 Conjugated with GLP-1 Peptide Method for the preparation of conjugated modified oligonucleotides comprising GLP-1 at the 5' position conjugated via a 3-mercaptopropionate linker to C-terminal penicillamine.

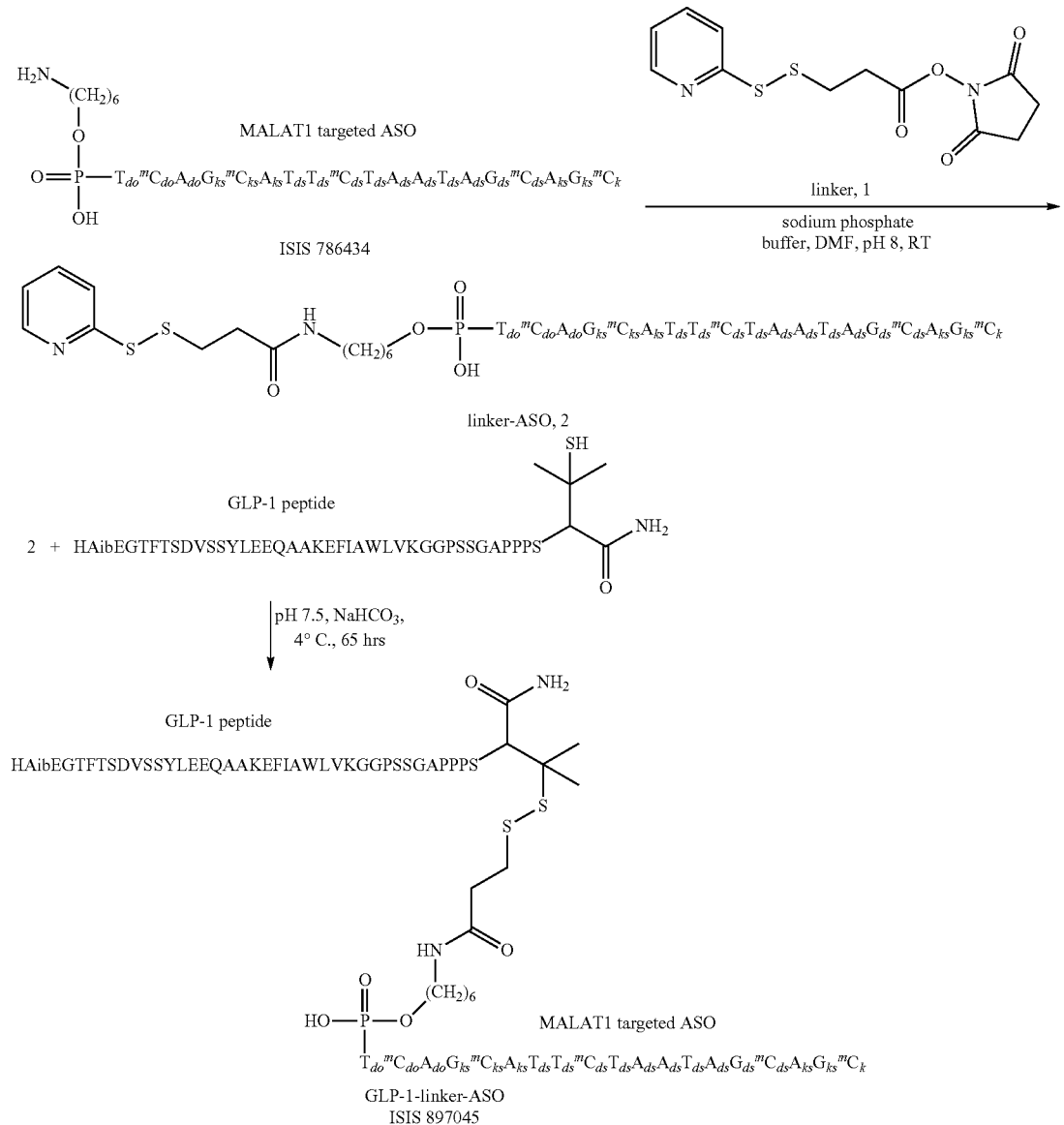

Compound 2 was synthesized as in Example 1 and was used as the starting material for reaction with the GLP-1 peptide: HisAibGluGlyThrPheThrSerAspValSerSerTyrLeuGluGluGlnAlaAlaLysGluPheIleAlaTrpLeuValLysGlyG lyProSerSerAlaProProProSerPen-NH2 (SEQ ID NO: 23), which was synthesized via standard solid phase peptide synthesis. Aib is 2-aminoisobutyric acid and Pen is penicillamine. Compound 2 was dissolved in degassed water and 0.1M NaHCO₃ was added to adjust the pH to ~8.0. GLP-1 peptide was dissolved in degassed water. The solution of compound 2 and the peptide solution were mixed with gentle vortexing and pH was checked. 0.1M NaHCO₃ was added to adjust the pH to ~7.5. After ~2 hr, additional peptide was added and NaHCO₃ was added to adjust the pH up. Reaction was transferred to 4° C. for ~65 hours and the product was purified by HPLC as described in Example 1.

Example 3: Preparation of Antisense Oligonucleotide (ASO) Targeted to FOXO1 Conjugated with GLP-1 Peptide Method for the preparation of conjugated modified oligonucleotides comprising GLP-1 at the 5' position conjugated via a 3-mercaptopropionate linker.

ION 913193, a 5'-GLP-1 peptide conjugated ASO targeted to FOXO1, was prepared according to the procedure of Example 1 starting with a 5'-hexylamino modified oligonucleotide (ION 913192) (nucleobase sequence: TCATCTTCTTAAAATACCC (SEQ ID NO: 59) having the chemical modifications: Tdo mCdo Ado Tks mCks Tds Tds mCds Tds Tds Ads Ads Ads Aks Tes Aks mCes mCks mCk (k=cEt; d=2'-deoxy; e=2'-MOE; mC=5-methylcytosine; o=phosphodiester; and s=phosphorothioate).

ION 913195, a control 5'-GLP-1 peptide conjugated ASO having a nucleobase sequence mismatched to FOXO1, was prepared according to the procedure of Example 1 starting with a 5'-hexylamino modified oligonucleotide (ION 913194) (nucleobase sequence: TCAGGC-CAATACGCCGTCA (SEQ ID NO: 60) having the chemical modifications: Tdo mCdo Ado Gks Gks mCks mCds Ads Ads Tds Ads mCds Gds mCds mCds Gds Tks mCks Ak (k=cEt; d=2'-deoxy; e=2'-MOE; mC=5-methylcytosine; o=phosphodiester; and s=phosphorothioate).

Example 4: Preparation of Antisense Oligonucleotide (ASO) Targeted to Insulin Conjugated with GLP-1 Peptide Method for the preparation of conjugated modified oligonucleotides comprising GLP-1 at the 5' position conjugated via a mercaptoproprionate linker.

ION 919553, a 5'-GLP-1 peptide conjugated ASO targeted to insulin, was prepared according to the procedure of Example 1 starting with a 5'-hexylamino modified oligonucleotide (ION 919553) (nucleobase sequence: TCAGC-CAAGGTCTGAAGGTCACC (SEQ ID NO: 61) having the chemical modifications: Tdo mCdo Ado Ges mCes mCes Aes Aes Gds Gds Tds mCds Tds Gds Ads Ads Gds Gds Tes mCes Aes mCes mCe (k=cEt; d=2'-deoxy; e=2'-MOE; mC=5-methylcytosine; o=phosphodiester; and s=phosphorothioate).

Example 5: Preparation of Antisense Oligonucleotide (ASO) Duplex Targeted to MALAT1 Conjugated with GLP-1 Peptide ION 951976 (nucleobase sequence: GCTGCTATT-AGAATGC (SEQ ID NO: 62) having the chemical modifications: Ges mCeo Tdo Gdo mCdo Tdo Ado Tdo Tdo Ado Gdo Ado Ado Tds Ges mCe (d=2'-deoxy; e=2'-MOE; mC=5-methylcytosine; o=phosphodiester; and s=phosphorothioate), was synthesized and purified using standard solid-phase oligonucleotide procedures. ISIS 816385 described in Example 1 was hybridized with ION 951976, generating a duplex of the two oligonucleotides.

Example 6: Specific Targeting of Pancreatic Beta Islet Cells In Vivo by GLP-1 Peptide Conjugated ASOs Study 1
To determine if conjugation of GLP-1 peptide to ASO increases ASO delivery to the pancreas, male $C_{57}BL/6$ mice fed a chow diet received 2 intravenous injections of either a 3-10-3 cEt ASO targeting murine MALAT1 (ISIS 556089) (nucleobase sequence: GCATTCTAATAGCAGC) (SEQ ID NO: 63) or a GLP-1 conjugated MALAT1 ASO (ISIS 816385) described in Example 1 at concentrations of 1.8, 0.6, or 0.2 µmol/kg. Tissues were collected 72 hours after the final injection to assess delivery and potency of the compounds.

MALAT1 expression was detected using the QuantiGene ViewRNA tissue assay (Affymetrix, cat. No. QVT0011). Species-specific MALAT1 probes were purchased from Affymetrix (cat. No. VB-11110-01/mouse; VF1-13963/monkey). In brief, mouse tissues were fixed in 10% neutral-buffered formalin and embedded into paraffin and sectioned into 4-mm sections. After deparaffinization, the tissue slides were boiled in Affymetrix pretreatment solution for 10-30 minutes followed by treatment with protease at 40° C. for 10 to 40 minutes depending on tissue. The MALAT1 RNA probe was used at a 1:40 dilution and was incubated with sample at 40° C. for 120 minutes. After washing, the MALAT1 RNA/probe complex was hybridized with preamplifier, amplifier, and AP-oligonucleotides at 40° C. for 25, 15, and 15 minutes, respectively. After removal of free AP oligonucleotide by washing in PBS, the slide was incubated with Fast Red substrate at room temperature for 30 minutes. The tissue images were acquired using an Aperio scanner. Hung et al., 2013 *Nuc Acid Ther.* 369-78.

In situ hybridization analysis indicated that GLP-1 peptide conjugation reduced MALAT1 staining in beta islet cells, but not acinar cells, of the pancreas. ASO staining of pancreatic sections demonstrated the GLP-1 conjugate improved potency by increasing ASO delivery to the tissue. Mice treated with GLP-1 conjugated MALAT1 ASO (ISIS 816385), but not mice treated with unconjugated MALAT1 ASO (ISIS 556089), exhibited reduced MALAT1 expression in pancreatic beta islet cells. Mice treated with various doses of ISIS 816385 exhibited reduced MALAT1 expression in pancreatic beta islet cells. Mice treated with GLP-1 conjugated MALAT1 ASO (ISIS 816385), but not mice treated with unconjugated MALAT1 ASO (ISIS 556089), exhibited ASO accumulation in pancreatic beta islet cells. GLP-1 conjugated MALAT1 ASO (ISIS 816385) accumulated in a dose dependent manner in pancreatic beta islet cells of treated mice.

Study 2
To determine a dose response of a GLP-1 conjugated MALAT1 ASO (ISIS 816385) described in Example 1 on pancreatic MALAT1 expression, male C57BL/6 mice fed a chow diet received a single intravenous injection of ISIS 816385 or an unconjugated MALAT1 ASO (ISIS 556089) described above at concentrations of 0.2, 0.06, and 0.02 µmol/kg.

MALAT1 expression was detected using the QuantiGene ViewRNA tissue assay described above.

In situ hybridization analysis indicated that GLP-1 peptide conjugation reduced MALAT1 staining in beta islet cells of the pancreas at the 0.2 µmol/kg dose and 0.06 µmol/kg dose. No observable effect of ISIS 816385 or ISIS 556089 was observed in liver for any of the doses.

Example 7: Antisense Inhibition of MALAT1 and FOXO1 with GLP-1 Peptide Conjugated Antisense Oligonucleotides in HEK293 Cells Overexpressing the Human GLP-1 Receptor Antisense oligonucleotides designed to target MALAT1 and FOXO1 were conjugated to a Glucagon Like Peptide 1 receptor peptide agonist (GLP-1 peptide) and tested for their effect on human target gene expression using a HEK293 cell line with stable constitutive expression of the human GLP-1 receptor (hGLP1R-HEK).

The hGLP1R-HEK cell line was generated by expressing hGLP1R in Flp-IN™ 293 cells. Cultured hGLP1R-HEK cells were seeded at a density 30,000 cells per well in 96 well plates and saline, 100 nM or 10 µM of unconjugated parent antisense oligonucleotide ISIS 556089 targeted to MALAT1 described above or ISIS 776102 (nucleobase sequence: TCTTCTTAAAATACCC) (SEQ ID NO: 64) targeted to FOXO1, or corresponding GLP-1 peptide conjugated antisense oligonucleotides (ISIS 816385 targeted to MALAT1 described above or ION 913193 targeted to FOXO1 described above) for approximately 24 hrs. After the treatment period, cells were harvested, the mRNA isolated and adjusted to total RNA content as measured by nanadrop UV-Vis spectrophotometer. MALAT1 or FOXO1 mRNA levels were measured by quantitative real-time PCR and normalized to the mRNA levels of the house keeping gene (RPLP0) in the same samples. Human MALAT1 mRNA levels were measured using gene expression assays HS00273907 and FOXO1 mRNA levels were measured using assay Hs01054576 (Applied Biosystems). The mRNA level of the house keeping gene RPLP0 was measured using a primer probe set with forward sequence CCATTCTAT-CATCAACGGGTACAA (SEQ ID NO: 66), reverse sequence AGCAAGTGGGAAGGTGTAATCC (SEQ ID NO: 67).

Figure 1B:
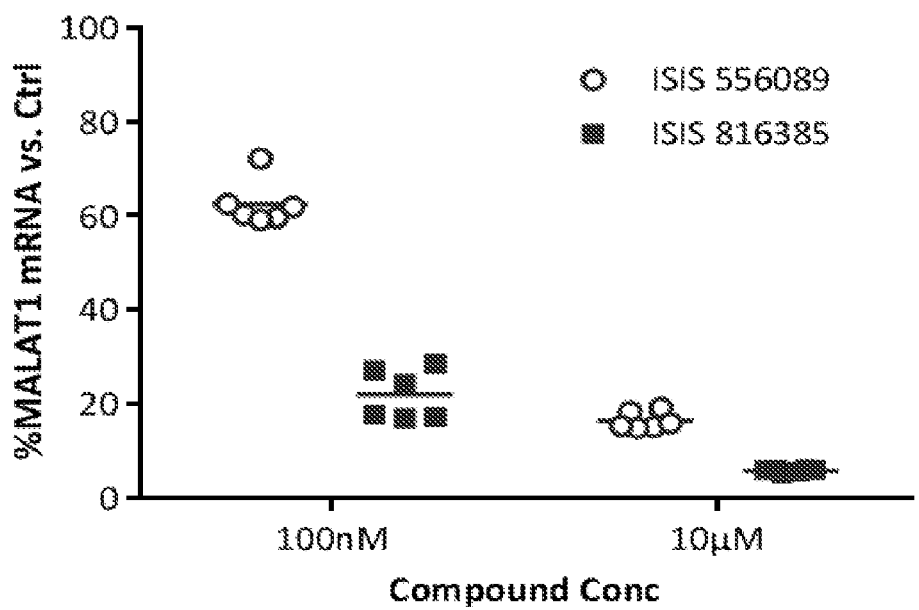

Data is presented as percent inhibition of MALAT1 or FOXO1 mRNA relative to untreated control cells. Open symbols represent treatment with parent antisense oligonucleotides whereas closed symbols represent treatment with antisense nucleotides conjugated to a GLP-1 peptide. As illustrated in FIG. 1, in the hGLP1R-HEK cell line antisense oligonucleotides were more potent inhibiting MALAT1 or FOXO1 mRNA when conjugated to GLP-1 peptide compared to parent antisense oligonucleotides.

Example 8: Dose Dependent Antisense Inhibition of MALAT1 Following Treatment with Unconjugated Parent or GLP-1 Peptide Conjugated Antisense Oligonucleotides in Wild Type, and HEK293 Cells Overexpressing Human GPR40 or GLP-1 Receptors The MALAT1 antisense oligonucleotides from Example 7 were further tested at various concentrations in wild type, hGPR40 and hGLP1R-HEK cells.

Figure 2A:
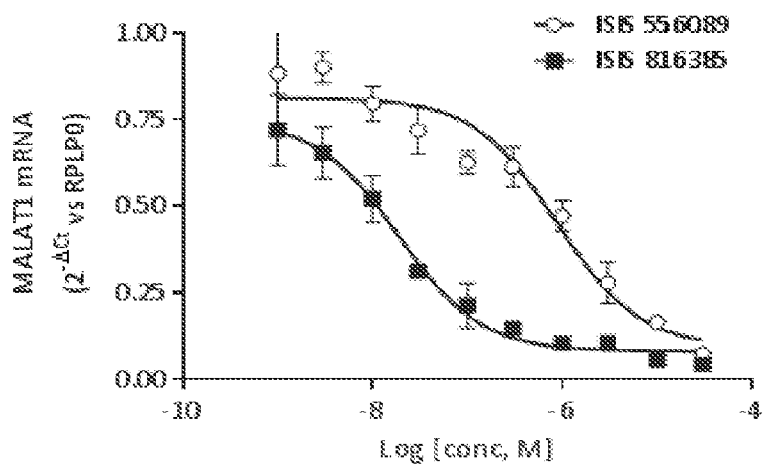
FIG. 2 is a graph showing MALAT1 mRNA levels relative to antisense oligonucleotide (ASO) concentration in GLP1 receptor overexpressing HEK293 cells (FIG. 2A), wild type HEK293 cells (FIG. 2B), or GRP40 overexpressing HEK293 cells (FIG. 2C) treated with unconjugated parent MALAT1 ASO (ISIS 556089) or GLP1-conjugated MALAT1 ASO (ISIS 816385).
Figure 2B:
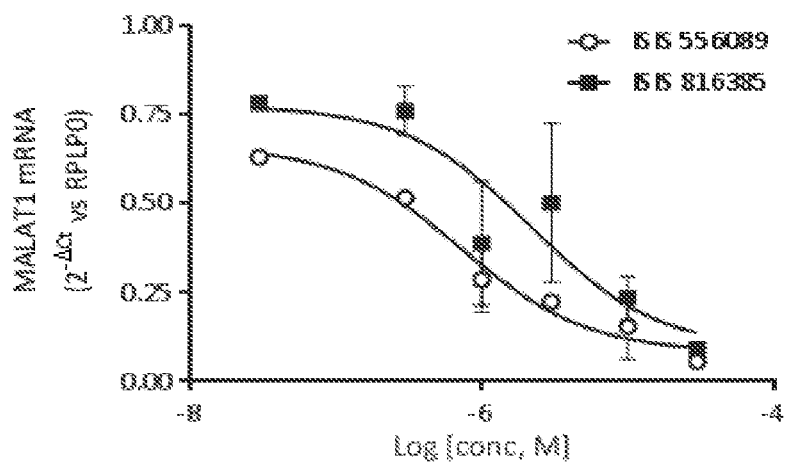

Cultured hGLP1R-HEK, wild type HEK293 (WT HEK293) cells or cells expressing hGPR40 receptor were seeded at a density 30,000 cells per well in 96 well plates and treated with 0.001, 0.003, 0.01, 0.03, 0.1, 0.3, 1, 3, 10 or 30 µM of antisense oligonucleotide, concentrations as indicated in FIG. 2, for approximately 24 hrs. After the treatment period cells were harvested, mRNA isolated and MALAT1 mRNA levels measured by quantitative real-time PCR using the primer probe set as described herein (Example 7). Data is presented as MALAT1 mRNA levels normalized relative to a house keeping gene (RPLP0). Open symbols represent treatment with parent antisense oligonucleotide targeting MALAT1 (ISIS 556089) whereas closed symbols represent treatment with the same antisense nucleotide conjugated to a GLP-1 peptide (ISIS 816385).

The half maximal inhibitory concentration (IC50) of each oligonucleotide is presented in the table below.

TABLE 1

| Treatment | hGLP1R-HEK cells | WT HEK293 cells |
|---|---|---|
| ISIS 556089 | IC50 = 0.87 µM | IC50 = 0.74 µM |
| ISIS 816385 | IC50 = 0.02 µM | IC50 = 2.21 µM |

Figure 2C:
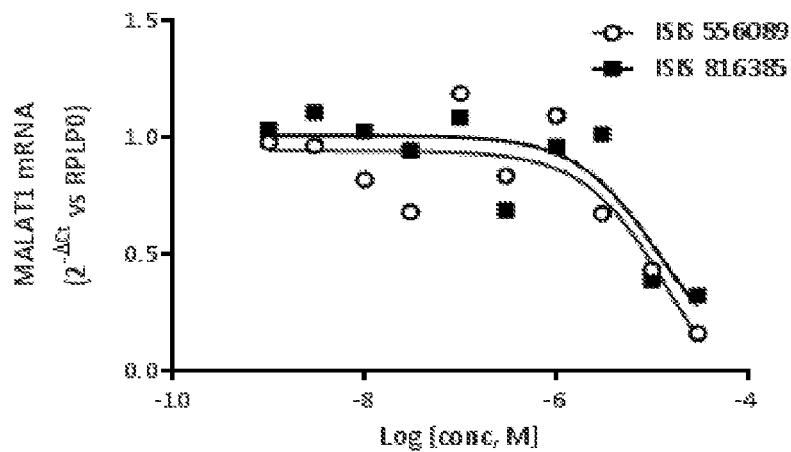

The antisense oligonucleotide was 40 times more potent inhibiting MALAT1 gene expression when conjugated to GLP-1 peptide agonist in the hGLP1R-HEK cell line (FIG. 2A) and not WT HEK293 (FIG. 2B) or hGPR40-HEK cell lines (FIG. 2C).

Example 9: Antisense Inhibition of MALAT1 and FOXO1 in Mouse Primary Islets of Langerhans Following Treatment with Unconjugated Parent or GLP-1 Peptide Conjugated Antisense Oligonucleotides Antisense oligonucleotides targeting MALAT1 and FOXO1 were further tested in mouse primary islets of Langerhans for ability to reduce gene expression.

Pancreatic islets were isolated by collagenase digestion from pancreas collected from exsanguinated 12 to 15 weeks old female C57BL/6Crl mice. Islets were maintained in tissue culture until use. Islet were dissociated into single cells by shaking in media containing a low extracellular calcium concentration. 10 to 20 intact or dissociated islets were plated on plastic Petri Dishes and treated with 10 µM of antisense oligonucleotides for approximately 24 hrs. After the treatment period cells were harvested, RNA isolated, adjusted to total RNA content, as measured by RIBOGREEN®. MALAT1 or FOXO1 mRNA levels measured by quantitative real-time PCR. Mouse Malat1 mRNA levels was measured using gene expression assay Mm01227912_s1 from Applied Biosystems, whereas mouse FOXO1 mRNA levels was measured using a primer probe set with forward sequence CAGTCACATACGGCCAATCC (SEQ ID NO: 68), reverse sequence CGTAACTTGAT-TTGCTGTCCTGAA (SEQ ID NO: 69) and probe sequence TGAGCCCTTTGCCCCAGATGCCTAT (SEQ ID NO: 70). All data was normalized to the mRNA level of the house keeping gene (RPLP0) in the same sample, measured using a primer probe set with forward sequence GAGGAATCA-GATGAGGATATGGGA (SEQ ID NO: 71), reverse sequence AAGCAGGCTGACTTGGTTGC (SEQ ID NO: 72) and probe sequence TCGGTCTCTTCGACTAATCCCGCCAA (SEQ ID NO: 73).

Figure 3A:
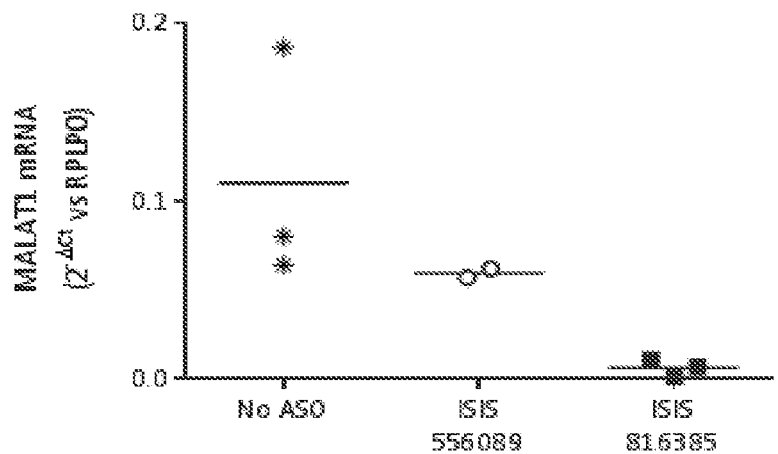
FIG. 3 is a graph showing MALAT1 mRNA levels in dispersed mouse islets treated with no ASO, unconjugated parent MALAT1 ASO (ISIS 556089), or GLP1-conjugated MALAT1 ASO (ISIS 816385) (FIG. 3A); MALAT1 mRNA levels in intact mouse islets treated with no ASO, unconjugated parent MALAT1 ASO (ISIS 556089), or GLP1-conjugated MALAT1 ASO (ISIS 816385) (FIG. 3B); and FOXO1 mRNA levels in intact mouse islets treated with no ASO, unconjugated parent FOXO1 ASO (ISIS 776102), GLP1-conjugated scrambled FOXO1 ASO (ION 913195), or GLP1-conjugated FOXO1 ASO (ION 913193) (FIG. 3C).
Figure 3B:
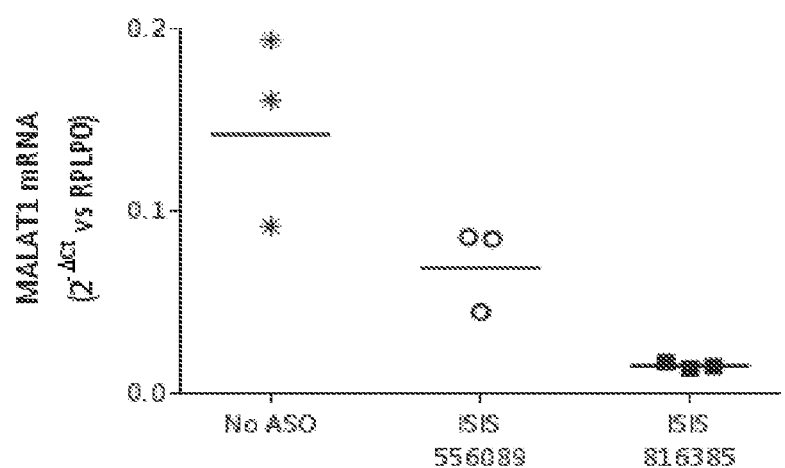
Figure 3C:
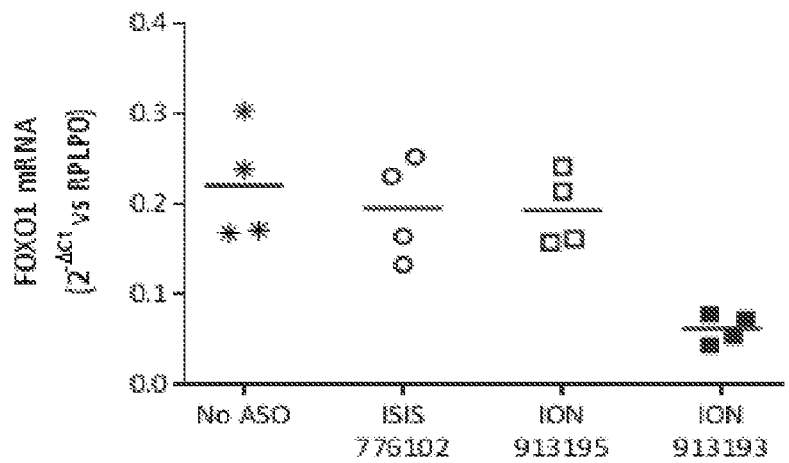

Data is presented in FIG. 3 as levels of MALAT1 or FOXO1 mRNA relative to the house keeping gene (RPLP0). Star symbols represents no treatment, open circles treatment with parent unconjugated antisense oligonucleotides (ISIS 556089 targeted to MALAT1 or ISIS 776102 targeted to FOXO1), open square treatment with scrambled FOXO1 antisense oligonucleotide sequence conjugated to the GLP1 peptide (ION 913195), whereas closed symbols represent treatment with GLP1 peptide conjugated antisense oligonucleotides against MALAT1 (ISIS 816385) or FOXO1 (ISIS 919193).

Example 10: Antisense Inhibition of FOXO1 and Reduction in Foxo1 Protein in Mouse Primary Islets of Langerhans Following Treatment with Unconjugated Parent and GLP-1 Peptide Conjugated Antisense Oligonucleotides Antisense oligonucleotides targeting FOXO1 were tested in mouse primary islets of Langerhans for ability to reduce protein levels.

Pancreatic islets were isolated by collagenase digestion from pancreas collected from euthanized 12 to 15 weeks old female B6.Cg-Lepob/J mice and maintained in tissue culture until use. 150 intact islets were placed in plastic Petri Dishes and treated with 1 µM of antisense oligonucleotides for 3 hrs every 24 hrs and harvested after approximately 24 hrs, 48 hrs or 96 hrs total treatment time respectively. After the treatment period, islets were harvested, and half of the islets were used to measure FOXO1 mRNA levels as described herein (Example 9). Half of the islets were homogenized in M-PER protein extraction reagent (Thermo Scientific) containing a protease inhibitor cocktail (Complete Mini and phosphoSTOP, Roche Diagnostics). The protein content of lysates were quantitated using BCA Assay Reagent (Pierce). FoxO1 protein was detected by Western Blot analysis using the primary antibodies C29H4 against FoxO1 (Cell Signalling, #2880). α-tubulin was measured as a control for sample loading on gel, using a primary antibody from Sigma (#T6074). For the anti-FoxO1 antibody, the secondary antibody was HRP-conjugated polyclonal goat anti-Rabbit P0448 (DAKO) and for the anti-α-tubulin antibody, the secondary antibody was HRP-conjugated polyclonal goat anti-mouse P0447 (DAKO). Enhanced chemiluminescence reagents (Pierce) were used for detection.

Inhibition of FOXO1 mRNA is presented as FOXO1 mRNA relative to the house keeping gene, expressed as percent of untreated cells in the table below and shows a marginal reduction in mRNA with unconjugated antisense oligonucleotide (ISIS 776102) and more than 70% reduction with GLP-1 conjugated antisense oligonucleotide (ION 913193).

TABLE 2

| Islet FOXO1 mRNA levels relative to control (RPLP0) | | | |
|---|---|---|---|
| Treatment | 24 hours | 48 hours | 96 hours |
| Vehicle | 100% | 100% | 100% |
| ISIS 776102 | 82% | 86% | 92% |
| ION 913193 | 31% | 30% | 25% |

The Western Blot showed a reduction in FoxO1 protein levels measured in islets treated with vehicle or antisense oligonucleotide for 96 hours. Protein levels were quantified by measuring the intensity of the bands on the gel normalized to the intensity of α-tubulin, and expressed as percent of vehicle treated islets. FoxO1 protein levels were set to 100% in vehicle treated islets. By contrast, FoxO1 protein levels were 5% in GLP-1-FOXO1 ASO treated islets.

Example 11: Uptake of Antisense Oligonucleotides in Islet of Langerhans In Situ in Pancreas after Administration of Unconjugated Parent or GLP-1 Peptide Conjugated Antisense Oligonucleotides Targeting MALAT1 to C57BL/6Crl Mice Unconjugated parent and GLP-1 peptide conjugated antisense oligonucleotides targeted to MALAT1 were further tested in vivo to evaluate the uptake of antisense oligonucleotides in pancreatic islets after either intravenous or subcutaneous administration of treatments.

Female C57BL/6Crl mice were assigned to five treatment groups. Two groups received either vehicle (saline) or 2 µmol/kg GLP-1 conjugated antisense oligonucleotide (ISIS 816385) by tail vein injection. Three groups received either saline, 2 µmol/kg unconjugated parent antisense oligonucleotide (ISIS 556089) or 2 µmol/kg GLP-1 conjugated antisense oligonucleotide (ISIS 816385) by subcutaneous administration twice a week for two weeks. All animals were sacrificed approximately 72 hrs after last dose, and pancreas harvested for ex vivo analysis of uptake of antisense oligonucleotides by immunohistochemistry.

All tissues were fixed in 10% neutral buffered formalin for 32 hours at room temperature. After fixation samples were dehydrated using standard ethanol series followed by xylene and embedded in paraffin. Tissue sections were cut at 4 µm thickness and mounted on Superfrost®Plus slides, then baked in a dry oven for 1 hour at 60° C. Immunohistochemistry for detection of antisense oligonucleotide was carried out in the Ventana Discovery XT immunostainer (Ventana Medical System, Inc) according to manufactures recommendation and all reagents were Ventana products (Roche Diagnostics, Basel, Switzerland). Protease 1 was used as enzyme antigen retrieval, with incubation for 8 minutes. Antibody blocker was added for reduction of background for 4 minutes, followed by addition of rabbit Anti-ASO 2.5 for 1 hour at 37° C. (dilution 1:5000, Ionis Pharmaceuticals). For secondary detection, OmiMap anti-rabbit HRP was incubated for 16 minutes, followed by chromogenic detection with DISCOVERY ChromoMap DAB Kit (RUO). Slides were counterstained with hematoxylin for 4 minutes followed with bluing for 4 minutes. Stained slides were analyzed under a standard bright-field microscope.

Antisense oligonucleotide was detected in the pancreatic islet of Langerhans from animals treated with ISIS 816385, dosed by either subcutaneous or intravenous administration. No antisense oligonucleotide was detected in the islets of Langerhans in animals treated subcutaneously with ISIS 556089.

Example 12: Antisense Inhibition of MALAT1 in Islet of Langerhans In Situ in Pancreas after Administration of Unconjugated Parent or GLP-1 Peptide Conjugated Antisense Oligonucleotides in C57BL/6Crl Mice Unconjugated parent and GLP-1 peptide conjugated antisense oligonucleotides against MALAT1 were further tested in vivo to evaluate the antisense inhibition of MALAT1 in pancreas after intravenous or subcutaneous administration of treatments.

Female C57BL/6Crl mice were assigned to five treatment groups as described herein (Example 11) All animals were sacrificed approximately 72 hrs after last dose, and pancreas harvested for ex vivo analysis of MALAT1 expression by in situ hybridization.

Tissues were prepared as described herein, Example 11. The in situ mRNA amplification and labelling process was performed on the Ventana Discovery ULTRA, an Automated ISH platform (Ventana Medical System, Inc) using the RNAscope® VS Assay based on Advanced Cell Diagnostics (ACD). Customized probes were obtained from ACD for the detection of MALAT1 mRNA, and various parameters were tested to optimize the novel RNAscope method for ISH. The signal was amplified using multiple steps, followed by labeled probes and detected using the RNAscope® 2.5 VS Reagent Kit-RED. Stained slides were analyzed under a standard bright-field microscope.

MALAT1 expression was reduced in the pancreatic islet of Langerhans but not in the exocrine tissue from animals subcutaneously or intravenously treated with GLP-1 peptide conjugated antisense oligonucleotide (ISIS 816385). MALAT1 expression was not reduced in animals treated subcutaneously with unconjugated parent antisense oligonucleotide (ISIS 556089).

Example 13: Uptake of Antisense Oligonucleotides in Liver 72 after Administration of Unconjugated Parent or GLP-1 Peptide Conjugated Antisense Oligonucleotides Targeting MALAT1 to C57BL/6Crl Mice Unconjugated parent and GLP-1 peptide conjugated antisense oligonucleotides against MALAT1 were further tested in vivo to evaluate the uptake of antisense oligonucleotides in liver by either intravenous or subcutaneous route of administration.

Animals were assigned to treatment as described herein, Example 11. All animals were sacrificed approximately 72 hrs after last dose, and liver harvested for ex vivo analysis of uptake of antisense oligonucleotides by immunohistochemistry.

Tissues were prepared and immunohistochemistry performed as described herein, Example 12.

Antisense oligonucleotide was detected in hepatocytes and Kupffer cells in the liver from animals treated with both ISIS 816385 and ISIS 556089, dosed by either subcutaneous or intravenous administration as indicated.

Example 14: Antisense Inhibition of MALAT1 in Liver after Administration of Unconjugated Parent or GLP-1 Peptide Conjugated Antisense Oligonucleotides in C57BL/6Crl Mice Unconjugated parent (ISIS 556089) and GLP-1 peptide conjugated antisense oligonucleotides against MALAT1 were further tested in vivo to evaluate the antisense inhibition of MALAT1 in liver by intravenous and subcutaneous route of administration.

Female C57BL/6Crl mice were assigned to five treatment groups as described herein (Example 13). All animals were sacrificed approximately 72 hrs after last, and liver harvested for ex vivo analysis of MALAT1 expression by in situ hybridization.

Tissues were prepared, and in situ hybridization performed, as described herein, Example 12.

Liver MALAT1 expression was reduced in hepatocytes of animals treated with ISIS 816385 to a greater extent than in hepatocytes of animals treated with ISIS 556089 dosed by subcutanous administration. Liver MALAT1 was also reduced compared to vehicle control in animals dosed with ISIS 816385 by intravenous administration.

Example 15: Dose Dependent Antisense Inhibition of MALAT1 in Isolated Islet of Langerhans and Liver 72 Hrs after Administration of a Single Dose of Unconjugated Parent and GLP-1 Peptide Conjugated Antisense Oligonucleotides in C57BL/6Crl Mice Unconjugated parent and GLP-1 peptide conjugated antisense oligonucleotides were further tested in vivo to evaluate the potency of antisense inhibition of MALAT1 in isolated pancreatic islets of Langerhans relative to liver 72 hours after single subcutaneous administration.

Female C57BL/6Crl mice were assigned to eight treatment groups, receiving a single subcutaneous injection of either vehicle, 0.01 µmol/kg, 0.03 µmol/kg, 0.1 µmol/kg or 1 µmol/kg ISIS 816385, another three treatment groups received 0.01 µmol/kg, 0.1 µmol/kg or 1 µmol/kg ISIS 556089. All animals were sacrificed 72 hrs after last dose. Liver samples were collected and pancreatic islets isolated, as described herein (Example 9), for mRNA analysis. MALAT1 mRNA levels were quantified as described herein (Example 9) and expressed as percentage of vehicle treated animals (control).

No significant antisense inhibition of MALAT1 was observed in the liver in any of the treatment groups, or in islet of Langerhans from animals treated with parent antisense oligonucleotide (ISIS 556089). The GLP-1 peptide conjugated antisense oligonucleotide dose dependently inhibited MALAT1 mRNA levels with an estimated ED50 of 0.07 µmol/kg.

Example 16: Dose Dependent Antisense Inhibition of FOXO1 in Isolated Islet of Langerhans and Liver 72 Hrs after Administration of a Single Dose of Unconjugated Parent and GLP-1 Peptide Conjugated Antisense Oligonucleotides in C57BL/6Crl Mice Unconjugated parent and GLP-1 peptide conjugated antisense oligonucleotides were further tested in vivo to evaluate the potency of antisense inhibition of FOXO1 in isolated pancreatic islets of Langerhans relative to liver 72 hours after subcutaneous administration of a single dose.

Female C57BL/6Crl mice were assigned to seven treatment groups, receiving a single subcutaneous injection of either vehicle, 0.01 µmol/kg, 0.03 µmol/kg, 0.1 µmol/kg or 1 µmol/kg ION 913193, with two treatment groups receiving 0.01 µmol/kg or 1 µmol/kg ISIS 776102. All animals were sacrificed 72 hrs after last dose. Liver samples were collected and pancreatic islets isolated, as described herein (Example 9), for mRNA analysis. FOXO1 mRNA levels were quantified as described herein (Example 9) and expressed as percentage of vehicle treated animals (control).

No significant antisense inhibition of FOXO1 was observed in the liver in any of the treatment groups, or in islet of Langerhans treated with parent antisense oligonucleotide (ISIS 776102). The GLP-1 peptide conjugated antisense oligonucleotide dose dependently inhibited FOXO1 mRNA levels with an estimated ED50 of 0.04 µmol/kg.

Example 17: Antisense Inhibition of FOXO1 in Isolated Islet of Langerhans and Liver after 6 Weeks Repeated Administration of Unconjugated Parent or GLP-1 Peptide Conjugated Antisense Oligonucleotides to Ob/Ob Mice Unconjugated parent and GLP-1 peptide conjugated antisense oligonucleotides were further tested in vivo to evaluate the potency of antisense inhibition of FOXO1 in isolated pancreatic islets of Langerhans relative to liver after 6 weeks of treatment.

Male ob/ob mice (B6.V-Lepob/OlaHsd, Harlan) were assigned to five treatment groups receiving either vehicle, 0.1 µmol/kg ISIS 776102, 0.1 µmol/kg ION 913195, 0.03 ION 913193 or 1 µmol/kg ION 913193. All animals were treated once weekly for 6 weeks. Approximately 120 hrs after last dose all animals were sacrificed, liver samples collected and pancreatic islets isolated, as described herein (Example 9), for mRNA analysis. FOXO1 mRNA levels were quantified as described herein (Example 9) and mRNA levels expressed relative to housekeeping gene in each sample (RPLP0).

No significant antisense inhibition of FOXO1 in the liver in any of the treatment groups, or in islet of Langerhans treated with parent antisense oligonucleotide (ISIS 776102) or scrambled FOXO1 antisense oligonucleotides sequence conjugated to GLP-1 peptide was observed (ION 913195).

The GLP-1 peptide conjugated antisense oligonucleotide (ION 913193) treated animals had reduced FOXO1 mRNA levels in isolated islets of Langerhans at both dose levels tested (42% average FOXO1 mRNA reduction at 0.03 mol/kg and 72% average FOXO1 mRNA reduction at 0.1 µmol/kg), indicating that GLP-1 peptide conjugation enhances antisense inhibition in pancreatic islets of Langerhans in vivo.

Example 18: Reduction of FoxO1 Protein Levels in Islets of Langerhans Isolated from Ob/Ob Mice Treated for 6 Weeks with Unconjugated Parent or GLP-1 Peptide Conjugated Antisense Oligonucleotide Unconjugated parent and GLP-1 peptide conjugated antisense oligonucleotides were further tested for the ability to reduce FoxO1 protein levels in pancreatic mouse islets of Langerhans isolated from ob/ob mice treated for 6 weeks.

Male ob/ob mice were assigned to five treatment groups as described herein (Example 17) Approximately 120 hrs after last dose all animals were sacrificed and pancreatic islets isolated for FoxO1 protein analysis as described herein (Example 10). Random samples were selected from each treatment group and loaded on each gel such that at least one sample from each treatment group was analysed on the same gels. FoxO1 protein levels were measured by quantifying the intensity and normalized against the α-tublin levels in the same sample. All samples within individual gels were expressed as percentage of the levels measured in islets of animals receiving ION 913195.

Foxo1 protein levels were reduced in animals treated with ION 913193; relative to ION 913195 by 57% and 81% in animals receiving 0.03 µmol/kg and 0.1 µmol/kg respectively, and 64% and 36% relative to animals treated with 0.1 µmol/kg ISIS 776102.

Example 19: Preparation of GLP-1 Peptide Conjugated Antisense Oligonucleotide Targeted to MALAT1

ION 962963, a 5'-GLP-1 peptide conjugated ASO targeted to MALAT1, was prepared according to the procedure of Example 1 starting with a 5'-hexylamino modified oligonucleotide (ISIS 722061) (nucleobase sequence: GCATTCTAATAGCAGC (SEQ ID NO: 65) having the chemical modifications Gks mCks Aks Tds Tds mCds Tds Ads Ads Tds Ads Gds mCds Aks Gks mCk (k=cEt; d=2'-deoxy; e=2'-MOE; mC=5-methylcytosine; o=phosphodiester; and s=phosphorothioate).

Example 20: Preparation of Antisense Oligonucleotide Targeted to MALAT1 Conjugated to GLP-1 Peptide Via a Click Linker Method for the preparation of conjugated modified oligonucleotides comprising GLP-1 at the 5' position conjugated via a click linker.

Preparation of 5'-BCN MALAT-1 Targeted Oligonucleotide ISIS 791173:

A 5'-hexylamino modified oligonucleotide (ISIS 786434) (nucleobase sequence: TCAGCATTCTAATAGCAGC (SEQ ID NO: 58) was synthesized and purified using standard solid-phase oligonucleotide procedures. The 5' end of the modified oligonucleotide comprises a hexamethylene linker and a terminal amine. BCN—NHS ester (Mol. Wt 291.11 g/mol, 7441R,8S,9s)-Bicyclo(6.1.0)non-4-yn-9-ylmethyl N-succinimidyl carbonate) was obtained from Aldrich. Modified oligonucleotide (~1 g) was dissolved in 5 mL sodium tetraborate buffer, pH 8.5. 13.4 mg of BCN—NHS ester was dissolved in 10 mL DMSO, added to the ASO solution, and stirred at room temperature for 4 hours. Reaction mixture was diluted with 1 M NaCl solution and desalted by HPLC on a reverse phase column.

Preparation of GLP-1 Click-Conjugated ASO (ION 1071996)

12 mg modified oligonucleotide ISIS 791173 was dissolved in 1 mL of 0.1M sodium tetraborate, pH 8.5 (ASO solution), and 12 mg of N-terminal azido-GLP-1 peptide was dissolved in 400 µL DMF (peptide solution). The peptide solution was added to the ASO solution and stirred at RT for 18 hr. At 18 hr, a precipitate was observed and 1 mL of additional DMF was added. The reaction was allowed to proceed for an additional 5 hr. The product was purified by HPLC on a SAX column with buffer A 100 mM NH₄OAc/30% ACN/H₂O and buffer B 1.5M NaBr/NH₄OAc/30% ACN/H₂O, and desalted by HPLC on a reverse phase column. Product fractions were collected and lypohylized to yield expected conjugated ASO, ION 1071996.

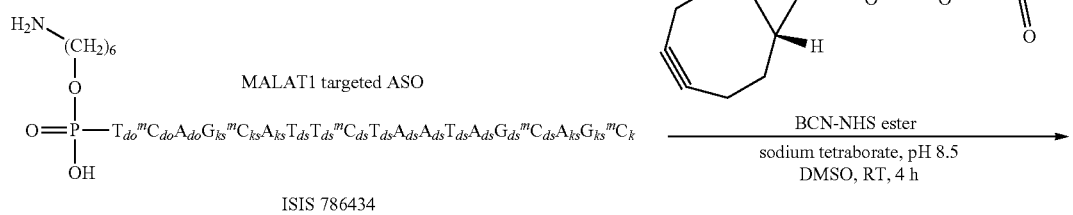

-continued

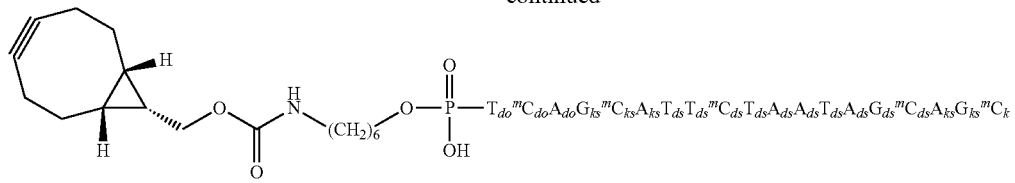

5'-BCN-carbamate-C6 MALAT1 ASO, ISIS 791173

+

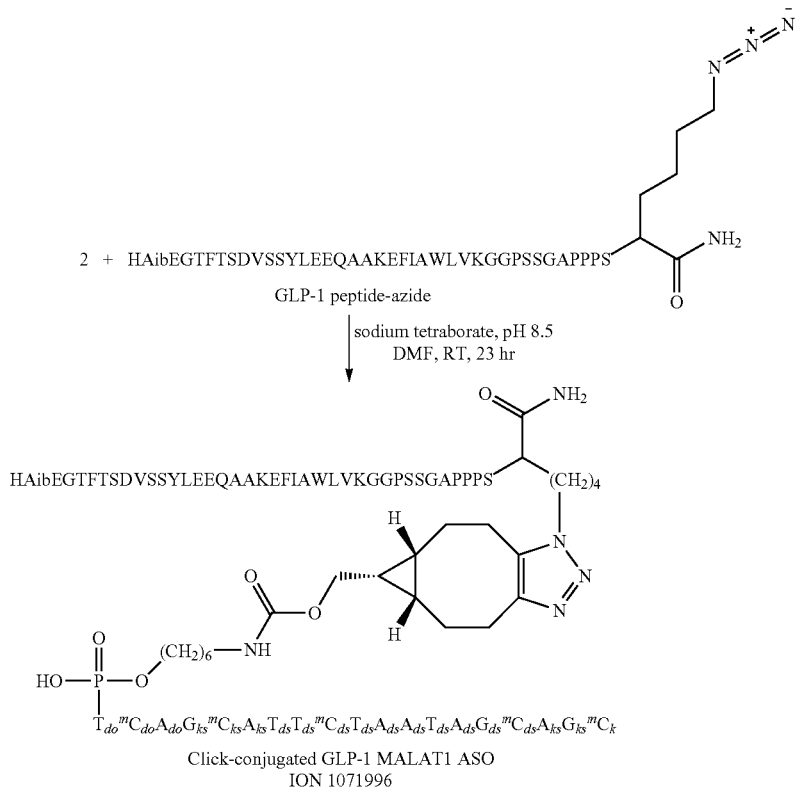

2 + HAibEGTFTSDVSSYLEEQAAKEFIAWLVKGGPSSGAPPPS

GLP-1 peptide-azide sodium tetraborate, pH 8.5
DMF, RT, 23 hr

HAibEGTFTSDVSSYLEEQAAKEFIAWLVKGGPSSGAPPPS

Click-conjugated GLP-1 MALAT1 ASO
ION 1071996

Example 21: Antisense Inhibition of MALAT1 in Mouse Primary Islets of Langerhans Following Treatment with Unconjugated Parent or GLP-1 Peptide-Conjugated ASO with Various Linkers To determine if the chemistry of conjucation of GLP-1 peptide to ASO affects ASO delivery into the pancreas, male C57BL/6 mice received an intravenous injection of 0.6 µmol/kg/week once a week for three weeks of vehicle (saline), ISIS 556089 (parent unconjugated ASO), ISIS 816395 (GLP-1 conjugated ASO with a disulfide linker and 5' TCA linker), ION 962963 (GLP-1 conjugated ASO with a disulfide linker and no 5' nucleotide spacer), or ION 1071996 (GLP-1 conjugated ASO conjugated via a click linker). Tissues were collected 72 hours after the final injection to assess delivery and potency of the compounds.

MALAT1 expression was detected as in Example 6. In situ hybridization analysis indicated that MALAT1 expression in beta islet cells was reduced in mice treated with GLP-1 conjugated ASOs (ISIS 816385, ION 962963, and ION 1071996) compared to saline control, but not in mice treated with the unconjugated parent ASO (ISIS 556089).

Example 22: Dose-Dependent Reduction of MALAT-1 Expression in LVX-GLP1R Cells HEK cells stably expressing FLAG-tagged GLP1R were generated by infecting HEK 293 cells with FLAG-tagged GLP1R containing lentivirus produced by transfection of 293T cells with pLVX-IRES-Puro (Clontech Laboratories Inc., Mountainview, CA) harboring the FLAG-GLPIR insert. Infected cells were selected with puromycin (2 µg/ml) and then analyzed for receptor expression by western blot and immunofluorescence. Cultured GLPIR cells were plated at a density of 10,000 cells per well and treated with 0.3, 1, 3, 9, 27, 82, 247, 741, 2,222, 6,667, and 20,000 nM modified oligonucleotide for approximately 24 hours. After the treatment period, total RNA was prepared using an RNeasy mini kit (Qiagen, Valencia, CA, USA) and qRT-PCR was performed using the primer probe set RTS2739 (forward sequence: AGGCGTTGTGCGTAGAGGAT (SEQ ID NO: 74), reverse sequence: AAAGGTTACCAT-AAGTAAGTTCCAGAAAA (SEQ ID NO: 75), probe sequence: AGTGGTTGGTAAAAATCCGTGAGGTCGGX (SEQ ID NO: 76). Briefly, ~50 ng total RNA in 5 µl water was mixed with 0.3 µl primer probe sets containing forward and reverse primers (10 µM of each) and fluorescently labeled probe (3 µM), 0.3 µl RT enzyme mix (Qiagen), 4.4 µl RNase-free water, and 10 µl of 2×PCR reaction buffer in a 20 µl reaction. Reverse transcription was performed at 48° C. for 10 min, 40 cycles of PCR were conducted at 94° C. for 20 s, and 60° C. for 20 s within each cycle, using StepOne Plus RT-PCR system (Applied Biosystems, Phoenix, AZ, USA). The mRNA levels were normalized to the amount of total RNA present in each reaction as determined by Ribogreen assay (Life Technologies) and normalized to the saline control (100% expression). Results are shown in the table below and indicate increased dose-dependent inhibition of MALAT-1 with GLP-1 complexed ASOs with (816385) or without (962963) a TCA linker.

TABLE 3

Percent Inhibition of MALAT-1 expression in GLP1R HEK cells

| [ASO] (nM) | ISIS 556089 | ISIS 816385 | ION 962963 |
| --- | --- | --- | --- |
| 0.3 | 102 | 102 | 94 |
| 1 | 98 | 102 | 106 |
| 3 | 94 | 97 | 85 |
| 9 | 103 | 86 | 87 |
| 27 | 88 | 74 | 74 |
| 82 | 85 | 64 | 71 |
| 247 | 79 | 48 | 56 |
| 741 | 65 | 36 | 47 |
| 2222 | 65 | 28 | 30 |
| 6667 | 45 | 15 | 10 |
| 20000 | 27 | 7.7 | 0.7 |
| IC50 (µM) | 3.97 | 0.26 | 0.35 |

Example 23: Effect of Peptide Length and Conjugation Position on In Vitro Activity of GLP-1 Conjugated ASO Targeting MALAT1

In order to evaluate the effect of exact peptide sequence, peptide length, and conjugation position on the in vitro activity of a GLP-1 conjugated ASO complementary to MALAT1, a series of modified oligonucleotides were synthesized via click chemistry with variations in the peptide sequence. All peptides represent the C-terminal amide. ION 1083582 was synthesized from ION 791173 via a click reaction with a 5-azidopentanoic acid-modified lysine residue (X), as shown below. The other compounds were synthesized from ION 791173 via a click reaction with a C-terminal azidonorleucine (Z) as shown in Example 20 above.

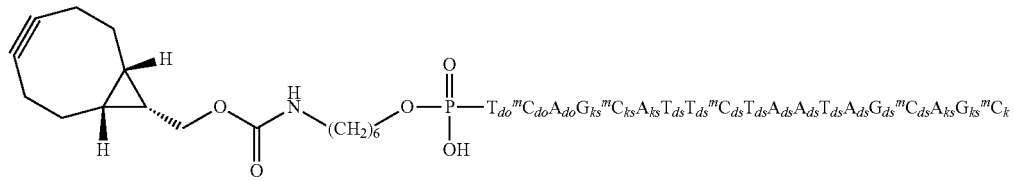

5'-BCN-carbamate-C6 MALAT1 ASO, ISIS 791173

+

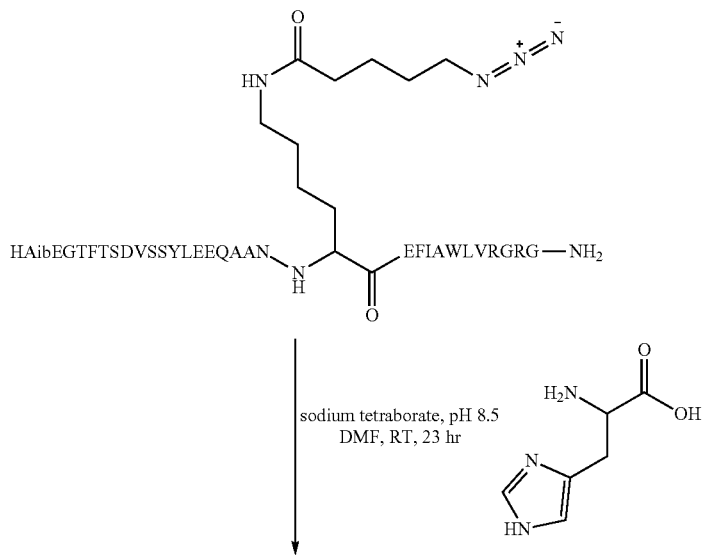

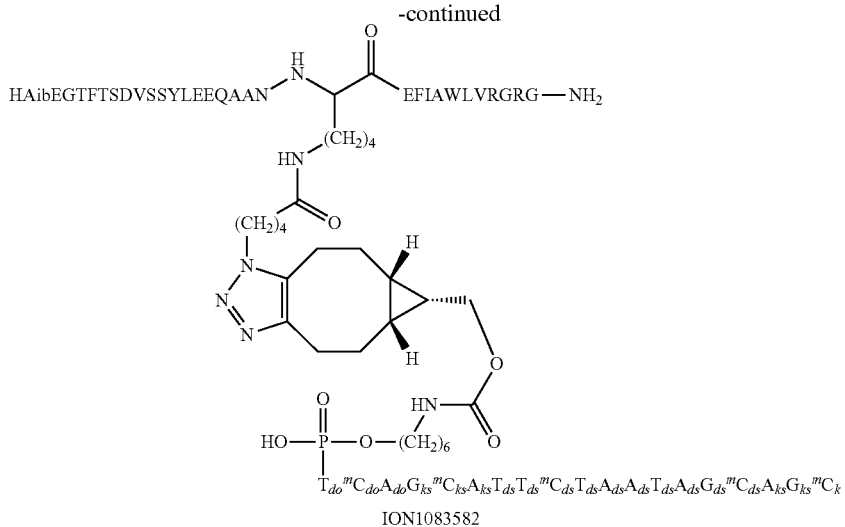

ION1083582

LVX-GLP1R cells (as described in Example 22) were plated at a density of 10,000 cells/well and incubated with 7 doses of peptide-conjugated ASOs in a 4-fold dilution series. After the treatment period, total RNA was prepared and analyzed as in Example 22 above. IC50s are shown in the table below.

TABLE 4

Effect of peptide composition and attachment point on peptide-conjugated ASO activity

| ION # | Peptide Sequence | IC50 | Attachment site |
|---|---|---|---|
| 556089 | n/a | 3.82 | n/a |
| 816385 | HAibEGTFTSDVSSYLEEQAAKEFIAWLVKGGPSSGAPPPSC | 0.35 | C-terminal C |
| 1083540 | HGEGTFTSDLSKQMEEEAVRLFIEWLKNGGPSSGAPPPSZ | 4.60 | C-terminal Z |
| 1083541 | HAibEGTFTSDVSSYLEGQAAKEFIAWLVRGRGZ | 0.75 | C-terminal Z |
| 1083542 | HAibEGTFTSDVSSYLEGQAAKEFIAWLVK(Aib)RZ | 0.29 | C-terminal Z |
| 1083569 | HSEGTFTSDVSSYLEGQAAKEFIAWLVKGRZ | 2.02 | C-terminal Z |
| 1085429 | HAibEGTFTSDVSSYLEEQAAKEFIAWLVKGGPSSGAPPZ | 2.34 | C-terminal Z |
| 1085430 | HAibEGTFTSDVSSYLEEQAAKEFIAWLVKGGPSSZ | 1.24 | C-terminal Z |
| 1085431 | HAibEGTFTSDVSSYLEEQAAKEFIAWLVKZ | 0.97 | C-terminal Z |
| 1085432 | HAibEGTFTSDVSSYLEEQAAKEFIAWLVZ | 0.25 | C-terminal Z |
| 1085433 | HAibEGTFTSDVSSYLEEQAAKEFIAWLZ | 0.38 | C-terminal Z |
| 1085435 | HAibEGTFTSDVSSYLEEQAAKEFIAWZ | 1.35 | C-terminal Z |
| 1085441 | HAibEGTFTSDVSSYLEEQAAZ | 2.63 | C-terminal Z |
| 1085470 | HGEGTFTSDLSKQMEEEAVRLFIEWLKNGZ | 4.08 | C-terminal Z |
| 1085471 | HGEGTFTSDLSKQMEEEAVRLFIEWLKNZ | 2.37 | C-terminal Z |
| 1085472 | HGEGTFTSDLSKQMEEEAVRLFIEWLKZ | 1.34 | C-terminal Z |
| 1085473 | HGEGTFTSDLSKQMEEEAVRLFIEWLZ | 1.26 | C-terminal Z |
| 1085478 | HGEGTFTSDLSKQMEEEAVRLFIEWZ | 6.08 | C-terminal Z |
| 1083582 | HAibEGTFTSDVSSYLEGQAANXEFIAWLVRGRG | 1.20 | Sidechain X |

Example 24: Preparation of a GLP-1 Conjugated siRNA Targeted to PTEN

Method for the Preparation of siRNA Nucleotide Duplexes Targeted to PTEN

ISIS 522247 (nucleobase sequence TTATCTATAAT-GATCAGGTAA (SEQ ID NO: 77) having the chemical modifications Txs Ufs Amo Ufs Cmo Ufs Amo Ufs Amo Afs Umo Gfs Amo Ufs Cms Afs Gins Gfs Ums Aes Ae (Tx=5'-(E)-vinylP-2'-O-methoxyethyl-thymine, f=2'-α-fluoro-2'-deoxyribose, m=2'-O-methylribose, e=2'O-methoxyethylribose, o=phosphodiester; and s=phosphorothioate) and ISIS 790973 (nucleobase sequence ACCTGATCATTATAGA-TAA (SEQ ID NO: 78) having the chemical modifications Afs Cms Cfo Umo Gfo Amo Ufo Cmo Afo Umo Ufo Amo Ufo Amo Gfo Amo Ufs Ams Af (as above)) were synthesized and purified using standard solid-phase oligonucleotide procedures.

GLP-1 conjugated ION 1055394 was prepared according to the procedure of Example 1 starting with a 5'-hexylamino modified oligonucleotide (ION 1055395) (nucleobase sequence ACCTGATCATTATAGATAA (SEQ ID NO: 78) having the chemical modifications Afs Cms Cfo Umo Gfo Amo Ufo Cmo Afo Umo Ufo Amo Ufo Amo Gfo Amo Ufs Ams Af (as above)) conjugated to a GLP-1 peptide with the sequence HisAibGluGlyThrPheThrSerAspValSerSerTyr-LeuGluGluGlnAlaAlaLysGluPheIleAlaTrpLeuValLysGlyG lyProSerSerGlyAlaProProProSerCys comprising a free N-terminal amine and a C-terminal amide. ISIS 522247 was hybridized with 790973, generating a duplex of the two oligonucleotides. ISIS 522247 was hybridized with 1055394, generating a duplex of the two oligonucleotides.

Example 25: Preparation of a GLP-1 Antagonist Conjugated Oligonucleotide

Method for the synthesis of GLP-1 antagonist conjugated oligonucleotide, DLSKQMEEEAVRLFIEW-LKNGGPSSGAPPPSC-S—S-Propionoyl-HA-o-TdomC-doAdoGksmCksAks TdsTdsmCdsTdsAdsAdsTd-sAdsGdsmCdsAksGksmCk (ION 998975).

38 mg of linker-ISIS 786434 (compound 2) described in Example 1 was dissolved 1.5 mL H$_2$O and 0.5 mL of 0.1M NaHCO$_3$/H$_2$O was added to adjust pH to ~7.5-8.0 (ASO solution).

27.7 mg of peptide DLSKQMEEEAVRLFIEW-LKNGGPSSGAPPPSC-NH$_2$ (SEQ ID NO: 79) was dissolved in 2 mL of DMF:0.1M NaHCO$_3$ (1:1) (peptide solution). The peptide solution was added to the ASO solution slowly and stirred at room temperature for 30 minutes. The reaction was monitored by LCMS and the stirring was continued for an additional 1 hour. The major fraction was found to be the expected product. The product was diluted with water and kept at 4° C. until it was purified by HPLC on a strong anion exchange column (Buffer A=100 mM ammonium acetate in 30% aqueous acetonitrile; Buffer B: 1.5 M NaBr in A, 0 to 60% B in 28 column volume). Fractions containing full length ASO were pooled together, diluted to get concentration of acetonitrile to 10%, and desalted by HPLC on a reverse phase column (Buffer A 0.1 M sodium chloride, B=water, C=50% acetonitrile in water). Fractions pooled together and evaporated to yield the expected product confirmed by LCMS.

Example 26: Method for the Preparation of Conjugated Modified Oligonucleotides Comprising GLP-1 at the 5' Position Conjugated Via a Maleimide Linker A 5' hexylamino modified oligonucleotide targeting MALAT1 (ISIS 786434) was synthesized and purified as previously described herein. ISIS 786434 was reacted with 5 eq. of N-Succinimidyl 3-maleimidopropionate (MW 266.21 g/mol) in sodium tetraborate buffer at pH7, RT to yield 5'-(3-Maleimdyl)propionyl-C6 MALAT1 ASO. GLP-1 peptide containing a C-terminal cysteine amide ("GLP-1 peptide-cysteinamide", HAibEGTFTSDVSSYLE-EQAAKEFIAWLVKGGPSSGAPPPSC-NH2) was dissolved in 0.1M sodium phosphate, pH 8.5/DMF and added to a solution of 5'-(3-Maleimdyl)propionyl-C6 MALAT1 ASO with stirring at room temperature. Product (ION 1086699) was formed.

---

What is claimed:

1. A method of modulating the expression of a nucleic acid target in a pancreatic beta-islet cell, wherein the cell expresses GLP-1 receptor on the surface, the method comprising contacting the cell with a compound comprising a modified oligonucleotide, a GLP-1 peptide conjugate moiety capable of binding to the GLP-1 receptor and a conjugate linker linking the modified oligonucleotide to the GLP-1 peptide conjugate moiety, wherein the oligonucleotide has a nucleobase sequence complementary to that of the nucleic acid target, thereby modulating expression of the nucleic acid target in the cell.

2. The method of claim 1, wherein contacting the cell with the compound inhibits expression of the nucleic acid target.

3. The method of claim 1, wherein the nucleic acid target is pre-mRNA, mRNA, non-coding RNA, or miRNA.

4. The method of claim 1, wherein the modified oligonucleotide is 15 to 30 linked nucleosides in length.

5. The method of claim 1, wherein the modified oligonucleotide comprises at least one modified internucleoside linkage, at least one modified sugar, or at least one modified nucleobase.

6. The method of claim 1, wherein the modified oligonucleotide comprises:
   a gap segment consisting of linked deoxynucleosides;
   a 5' wing segment consisting of linked nucleosides; and
   a 3' wing segment consisting of linked nucleosides;
   wherein the gap segment is positioned immediately adjacent to and between the 5' wing segment and the 3' wing segment and wherein each nucleoside of each wing segment comprises a modified sugar.

7. The method of claim 1, wherein the modified oligonucleotide is single-stranded.

8. The method of claim 1, wherein the GLP-1 peptide conjugate moiety is 8 to 50 amino acids in length.

9. The method of claim 1, wherein the conjugate linker comprises a disulfide linkage or group chosen from a cysteine group, a penicillamine group, a hexylamino group, a polyethylene glycol group, a triethylene glycol group, and a phosphate group.

10. The method of claim 1, wherein the conjugate linker comprises:
    (a)

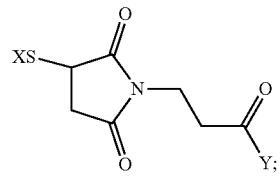

wherein X directly or indirectly attaches to the GLP-1 receptor ligand conjugate moiety; and
    wherein Y directly or indirectly attaches to the oligonucleotide

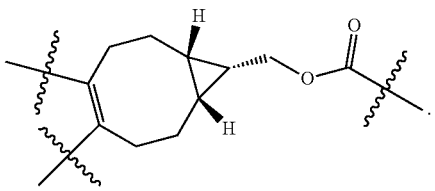 [SMILES: *C(=O)OC[C@@H]1[C@@H]2CC/C(*)=C(/*)CC[C@@H]21]

11. The method of claim 1, wherein the GLP-1 peptide comprises the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Cys (SEQ ID NO: 22), wherein Aib is aminoisobutyric acid.

12. The method of claim 11, wherein the GLP-1 peptide consists of the amino acid sequence: His-Aib-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro-Ser-Ser-Gly-Ala-Pro-Pro-Pro-Ser-Cys (SEQ ID NO: 22), wherein Aib is aminoisobutyric acid.

* * * * *